(12) United States Patent
Gopalakrishnan

(10) Patent No.: US 11,763,665 B2
(45) Date of Patent: Sep. 19, 2023

(54) NON-INVASIVE MULTIFUNCTIONAL TELEMETRY APPARATUS AND REAL-TIME SYSTEM FOR MONITORING CLINICAL SIGNALS AND HEALTH PARAMETERS

(71) Applicant: Muralidharan Gopalakrishnan, Navi Mumbai (IN)

(72) Inventor: Muralidharan Gopalakrishnan, Navi Mumbai (IN)

(73) Assignee: Muralidharan Gopalakrishnan, Maharashtra (IN)

( * ) Notice: Subject to any disclaimer, the term of this patent is extended or adjusted under 35 U.S.C. 154(b) by 417 days.

(21) Appl. No.: 16/645,811

(22) PCT Filed: Nov. 6, 2018

(86) PCT No.: PCT/IB2018/058718
§ 371 (c)(1),
(2) Date: Mar. 10, 2020

(87) PCT Pub. No.: WO2019/049116
PCT Pub. Date: Mar. 14, 2019

(65) Prior Publication Data
US 2020/0335211 A1  Oct. 22, 2020

Related U.S. Application Data

(63) Continuation of application No. 16/127,228, filed on Sep. 11, 2018, now abandoned.
(Continued)

(51) Int. Cl.
*A61B 5/1455* (2006.01)
*G08B 25/01* (2006.01)
(Continued)

(52) U.S. Cl.
CPC .......... *G08B 25/016* (2013.01); *A61B 5/0022* (2013.01); *A61B 5/02055* (2013.01);
(Continued)

(58) Field of Classification Search
CPC .............................. G16H 50/20; G16H 20/70
See application file for complete search history.

(56) References Cited

U.S. PATENT DOCUMENTS

2017/0181678 A1* 6/2017 Newberry .............. A61B 5/743

* cited by examiner

*Primary Examiner* — James M Kish
*Assistant Examiner* — Jessica L Mullins

(57) ABSTRACT

Multifunctional wireless apparatus, spectrometry instruments, real-time computational system and device ergonomic forms for live and telemetry monitoring of clinical parameters, health data and other vital medical information. Clinical parameters and medical information include pulse rate, respiratory rate, continuous blood glucose levels, continuous blood pressure levels, pulse rate variability, oxygen saturation ratio, body temperature, bio-electrical activity, sleep patterns, sleep health and other vital bio-signal data. The telemetry apparatus encompasses electrical and optical spectrometer instruments. The spectrometer designs and its accompanying circuit design ensure that device is bio-safe, lightweight, low-powered and portable. The bio sensor configuration, comprehensive hardware design, computational process and ergonomic design enables the measurement with more accuracy and efficiency, even in movement artefact prone conditions. The system design also assures that the computational process is real-time, faster and low powered. The wireless apparatus keeps track of the user information on daily diet pattern, fluid and water intake, exercise intensity, other essential health data, and provides necessary alerts. The apparatus yields persona-oriented stress levels and helps the user manage stress through guided practices. The health management system functions based
(Continued)

on the user inputs and previously computed parameters. An automated life-support functionality is integrated in the system, that can forecast chronic clinical conditions and health risks like sleep apnea, hypertension, hypoglycemia, hyperglycemia, hypothermia, hyperthermia, CO poisoning, fatigue conditions and more.

39 Claims, 34 Drawing Sheets

Related U.S. Application Data

(60) Provisional application No. 62/638,315, filed on Mar. 5, 2018, provisional application No. 62/557,069, filed on Sep. 11, 2017, provisional application No. 62/557,069, filed on Sep. 11, 2017.

(51) Int. Cl.
| | | |
|---|---|---|
| *G08B 21/02* | (2006.01) | |
| *G06F 1/16* | (2006.01) | |
| *H04W 4/02* | (2018.01) | |
| *H04W 4/029* | (2018.01) | |
| *G16H 10/65* | (2018.01) | |
| *H04W 4/90* | (2018.01) | |
| *G16H 20/30* | (2018.01) | |
| *G16H 40/67* | (2018.01) | |
| *G16H 50/50* | (2018.01) | |
| *G16H 50/30* | (2018.01) | |
| *G16H 50/70* | (2018.01) | |
| *G16H 50/20* | (2018.01) | |
| *G16H 20/10* | (2018.01) | |
| *G16H 20/60* | (2018.01) | |
| *G16H 20/70* | (2018.01) | |
| *G16H 80/00* | (2018.01) | |
| *A61B 5/00* | (2006.01) | |
| *A61B 5/0205* | (2006.01) | |
| *A61B 5/11* | (2006.01) | |
| *A61B 5/145* | (2006.01) | |
| *A61B 5/16* | (2006.01) | |
| *A61M 21/02* | (2006.01) | |
| *G06F 1/329* | (2019.01) | |
| *G06F 8/61* | (2018.01) | |
| *G06Q 10/1093* | (2023.01) | |
| *A61B 5/24* | (2021.01) | |
| *A61B 5/021* | (2006.01) | |
| *A61B 5/022* | (2006.01) | |
| *A61B 5/024* | (2006.01) | |
| *A61B 5/0245* | (2006.01) | |
| *A61B 5/026* | (2006.01) | |
| *A61B 5/0531* | (2021.01) | |
| *A61B 5/08* | (2006.01) | |
| *A61M 21/00* | (2006.01) | |
| *A63B 22/02* | (2006.01) | |
| *A63B 22/06* | (2006.01) | |

(52) U.S. Cl.
CPC ........... *A61B 5/1118* (2013.01); *A61B 5/1123* (2013.01); *A61B 5/1455* (2013.01); *A61B 5/14532* (2013.01); *A61B 5/14546* (2013.01); *A61B 5/14551* (2013.01); *A61B 5/165* (2013.01); *A61B 5/24* (2021.01); *A61B 5/4561* (2013.01); *A61B 5/486* (2013.01); *A61B 5/4809* (2013.01); *A61B 5/4812* (2013.01); *A61B 5/4818* (2013.01); *A61B 5/6802* (2013.01); *A61B 5/6831* (2013.01); *A61B 5/6833* (2013.01); *A61B 5/6895* (2013.01); *A61B 5/725* (2013.01); *A61B 5/7207* (2013.01); *A61B 5/742* (2013.01); *A61B 5/746* (2013.01); *A61B 5/747* (2013.01); *A61M 21/02* (2013.01); *G06F 1/163* (2013.01); *G06F 1/329* (2013.01); *G06F 8/61* (2013.01); *G06Q 10/1093* (2013.01); *G08B 21/0211* (2013.01); *G08B 21/0269* (2013.01); *G08B 21/0277* (2013.01); *G08B 21/0286* (2013.01); *G16H 10/65* (2018.01); *G16H 20/10* (2018.01); *G16H 20/30* (2018.01); *G16H 20/60* (2018.01); *G16H 20/70* (2018.01); *G16H 40/67* (2018.01); *G16H 50/20* (2018.01); *G16H 50/30* (2018.01); *G16H 50/50* (2018.01); *G16H 50/70* (2018.01); *G16H 80/00* (2018.01); *H04W 4/023* (2013.01); *H04W 4/027* (2013.01); *H04W 4/029* (2018.02); *H04W 4/90* (2018.02); *A61B 5/0245* (2013.01); *A61B 5/0261* (2013.01); *A61B 5/02108* (2013.01); *A61B 5/02233* (2013.01); *A61B 5/02405* (2013.01); *A61B 5/02416* (2013.01); *A61B 5/0531* (2013.01); *A61B 5/0816* (2013.01); *A61B 2560/0209* (2013.01); *A61B 2560/0214* (2013.01); *A61B 2560/0223* (2013.01); *A61B 2562/0219* (2013.01); *A61B 2562/16* (2013.01); *A61M 2021/0022* (2013.01); *A61M 2021/0044* (2013.01); *A61M 2205/18* (2013.01); *A61M 2205/505* (2013.01); *A63B 22/02* (2013.01); *A63B 22/0605* (2013.01)

NON-INVASIVE MULTIFUNCTIONAL TELEMETRY APPARATUS AND REAL-TIME SYSTEM FOR MONITORING CLINICAL SIGNALS AND HEALTH PARAMETERS

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

TECHNICAL FIELD

The present invention relates to a telemetry multi-functional medical instrumentation, real-time system and software device for precisely monitoring vital bio-signals. The vital bio-signals include cardiac rate, pulse rate variability, blood volume fluctuations, continuous blood sugar levels, continuous blood pressure levels, respiratory rate, neural activity, stress levels, oxygen saturation, body temperature, sleep patterns, etc. It also illustrates an integrated automated life-support system which forecasts the risk of congestive heart failure (CHF), hypertension, hypothermia, hypoglycemia, hyperglycemia, hyperthermia, sleep apnea (OSA), CO poising, nervous breakdown and other chronic medical conditions. It describes technologies that can work efficiently even in ambulatory and motion artefact prone situations. The processing system and hardware architecture of the device can be broadly classified into clinical system, live clinical diagnostic instrumentation, mobile medical device and telemetry wellness management technology. The overall disclosure presents an invention related to an advanced integrated solution of telemetry multi-functional medical device and general wellness instrument, more specifically a technology involving non-invasive bio-sensing technology.

BACKGROUND OF THE INVENTION

With the evolution of information technology and advanced medical diagnostic tools, it has become easier for medical professionals to diagnose and treat a disorder or life threatening medical condition. Despite this progress and advancement, the clinical centres and hospitals have become overly crowded places. The congested scenario of the clinical centres can be accounted to modern human lifestyle and use of stationary medical instruments. Clinical staff spend significant amount of time on attaching the several complex instrumentations and bulky devices to the patients.

Pulse oximeter devices have been utilized to improve the portability and reduce the complexity of the diagnosis, but these devices suffer limitations in terms of accuracy and deficient of information. Further attempts have been made by scientists and inventors to propose an instrument that could monitor multiple clinical parameters. But, these proposals as well lack proper implementation system and a corrugate technology architecture for non-invasive monitoring of multiple clinical parameters.

What is needed is an integrated solution of:
compact and less complex medical instrumentation with maximized clinical information; accurate telemetry device which can offer complete medical diagnostic solution; and an advanced wellness management technology.

SUMMARY OF THE INVENTION

The object of the invention is to present a precise state-of-art multifunctional telemetry medical device with an integrated well-being management solution for recording and monitoring multitude of vital bio-signals. The device can also be utilized to monitor real-time physiological parameters and other important clinical information even in a portable or remote setting. The invention addresses wireless mobile apparatus, hardware configurations, real-time system and embodiment forms for telemetry clinical monitoring and daily health management. The goal of invention is to present a compact portable solution for remote and live clinical monitoring, and for well-being management.

First Aspect

In the first aspect of the invention, a low-powered and compact hardware architecture of the telemetry apparatus is provided. The hardware architecture enables the measurement of clinical signals and general wellness parameters with more precision and efficiency.

The hardware comprises of electrical spectrometer and optical spectrometer. The optical spectrometer contains signal probe set of Green LED, Red LED, Infrared(IR) LED and Near-Infrared (Near-IR), which are operated by a single gain programmable LED frontend. The intensity and trigger of the input signals are adjusted through the circuit line of LED frontend and central microprocessor. A multiple pole switch set (or) a set of switches enables the operation of the multiple LED signal probes by a single frontend, which makes it low powered and more compact. The LED frontend contains an op-amp based bio-safety circuit that ensures the optical signal probes emit low powered optical signal. The low powered optical response is amplified and focused by an optical amplifier on the photodetector set. The photodetector set records the output optical response and the response is processed by a circuit line of stage 1 amplifier, buffer, power notch filter, stage 2 amplifier and ambient noise cancellation IC. The circuit line of the photodetector amplifies, filters and refines the output signal, and sends the processed output signal to the microprocessor.

The microprocessor is attached to a non-contact MEMs/NEMs temperature biosensor, which logs the body temperature response and thermal feedback. A 9/6 axis MEMs/NEMs accelerometer of the hardware is utilized as a real-time feedback to remove motion noise from bio-signal response. A set of wireless antennae of WLAN, BLE, GSM and GPS are either externally attached to the microprocessor or integrated inside the microprocessor. The set of wireless antennae communicates the data between the telemetry apparatus, and the set of external storage and computing devices like accessorial mobile devices, server, etc. The set of wireless antennae along with the accelerometer is used for tracking the real-time location and movement signals like phase, speed, steps taken, etc. The wireless microprocessor with inbuilt memory, is used for communicating commands and feedbacks with the internal electronic components of LED frontend, photodetector frontend, Impedance analyser IC, Accelerometer, temperature biosensors, other sensors, wireless antennas, USB module and other electronics modules. The function of microprocessor also includes computing and storing the required information. A touch display is attached to the hardware for viewing and accessing the real-time medical information, health data and on-device applications. The touch display is also used to operate the instrumentation and embodiment forms of the telemetry apparatus.

The hardware of the telemetry apparatus is powered by a power supply unit, which comprises of a power management IC, supercapacitor-battery set, supercapacitor-renewable energy harvester, USB module and negative voltage converter. The power management IC of power supply unit, attached to the hardware and microprocessor, regulates the current flow and power supply. The USB module and supercapacitor-battery are utilized for powering the electronic circuit. The USB module is also used for communicating the data with the external devices and charging the battery of the internal circuit. A negative voltage converter attached to the power management unit generates the negative voltage reference. The power supply unit includes an alternative and supplementary power supply unit containing renewable energy harvester and supercapacitor.

Apart from the display unit, the hardware of the telemetry device is internally or externally attached to an additional user interaction system of mic, video camera and speaker. The set of user interaction hardware components is utilized by user for interacting with the professional medical and health practitioners for clinical and health analysis. The professionals can send and receive the information, as well supervise the user through the user interaction system. The user interaction unit is also used as the means to perceive the recorded and computed information, and to operate the telemetry device and its in-built applications.

Second Aspect

The second aspect of the invention explains an electrical spectrometer apparatus of the telemetry hardware, which is utilized as the means for measuring electrical and electrodermal bio-signals. Preferably, a set of four electrodes of the electrical spectrometer are placed at equidistant positions in a straight line. An input electrical sensor injects the low power signal, and an electrical sensor drains the signal through the ground. A biosafety circuit, containing operational amplifier with a feedback impedance having lesser value compared to the input impedance, is attached to the input electrical sensor. The biosafety circuit improves operational safety of the electrical spectrometer apparatus.

A set of two response electrical sensors are placed between the signal input electrical sensor and drain electrode. The signal between response electrical sensors are processed, amplified and filtered through a response circuit line of Instrumental amplifier, Gain amplifier circuit, power notch filter, and V-I converter IC. The processed output response passes to the Impedance Analyzer chip. The Impedance Analyzer chip assess and resolves the output electrical response, and communicates the analyzed results to the microprocessor.

Third Aspect

A reflective optical spectrometer technology with adjacent LED-photodiode arrangement is exhibited in the third aspect of the invention. In the optical apparatus, the signal probes of Near-Infrared LED, Infrared LED, Red LED and Green LED, are embedded between their corresponding wavelength response photodetectors and are aligned in blood flow direction. An optical lens or a micro-prism is placed on the Near-IR LED probe to tune the Near-Infrared signal. The reflected responses are recorded by the set of corresponding adjacent photodetector probes, which are assembled at a noise-free recording distance. This adjacent configuration of LED-photodetectors enables simultaneous operation of different signals probes with more accuracy and speed. A non-contact MEMs/NEMs temperature biosensor is positioned at the edge of the sensor board with a minimum distance from heat dissipating surface, that is utilized for record the error-free body temperature and thermal noise feedback. A disposable foam/sponge is placed on the contact surface surrounding the sensors, signal probe and receiver area for reducing the motion errors and increasing the reusability.

Fourth Aspect

A compact and efficient spectrometer apparatus packaging method is proposed in the fourth aspect of the invention disclosure. The packaging design of the spectrometer comprises biosensors of electrical sensors, optical signal and detector probes, and non-contact MEMs/NEMs temperature sensor placed on the top surface (or) contact surface. The 9/6-axis accelerometer is arranged in a fixed reference direction to the biosensor direction, which is utilized as an efficient assembly technique to record the feedback signals and the movement signals. The Analog and Digital frontend plane is placed in a successive vertical plane to the biosensor plane. The third sequential plane is an electronic plane containing microprocessor, power supply unit, computing unit, wireless antennas and other ICs embedded plane. The last layer accommodates the set of battery, energy generation unit and other power unit components such that it does not obstruct the wireless antennas, which is used to reduce noise interruption. The aforementioned packaging technology and sequential packing method is utilized to reduce tracing efforts, curtail electrical noise and increase packaging efficiency. The apparatus packaging around the electronics is perforated with ventilation pores for regulating device heating. A disposable foam/sponge base is placed on the contact surface without obstructing the biosensors, which is used for reducing the motion errors and increasing the multi-use utility.

Fifth Aspect

In the fifth aspect, a ring form for remote and telemetry monitoring is provided. The LED signal probes of Near-Infrared LED, Infrared LED, Red LED and Green LED of the device are placed in an inverted transmission configuration, where LED probes faces the underside of the contact surface. The photodetector set of visible/IR and Near-IR photodetectors are aligned with the corresponding signal probes and are placed on the top response receiving surface. The inverted configuration of LED signal probes and photodetector set minimizes the background optical noise in the response recording. An optical lens is placed before the photodetector set for efficiently capturing and focusing low powered optical response on photodetector set. The NEMs/MEMs non-contact temperature bio sensor is assembled at edge of the ring frame and away from the heat dissipating surface, which is utilized to measure body temperature values and thermal feedback. A set of four electrical biosensors are assembled in a straight line, on the perpendicular contact surface to the optical probes, for extracting electrical and electrodermal bio-signals. A 9/6-axis NEMs/MEMs accelerometer is positioned in a specific direction with reference to the optical and electrical sensing probes, which is used as a sensor assembly method to record the movement feedback more accurately. The device is fabricated in a spiral ring structure with a heating dissipating and expandable casing material. The main ring frame contains sensors, wireless antennae, power supply unit, battery, digital chips, Analog ICs, microprocessor, integrated circuits and other electronic components. A clipper-hinge element protrudes from the main ring frame to form a spiral ring structure, which holds the instrument securely on the sensing spot. The expandable casing with adjustable clipper-hinge element, is utilized as the mechanical method for fastening the instrument in a size-adaptable manner. A reasonable number of pores are vented on the device frame to regulate electronics heating. A disposable foam base is placed on the contact surface surrounding the biosensors, which is utilized to enhance the mechanical gripping, clinical hygiene and reusability efficiency.

Sixth Aspect

A ring embodiment form for telemetry monitoring and daily wellness management is explained in the sixth aspect of the invention. The ring apparatus has an open ring structure for comfortably holding the device on the sensing spot in a size adjustable manner. The ring comprises of sensing components of optical apparatus, electrical spectrometer apparatus and other biosensor components, which are placed at an optical sensing spot. A vibrator is implanted on the contact of the ring to guide the user during mental stress, and to prompt the scheduled alarms calls. The device has an in-built persona-oriented stress management application, which automatically activates and guides the user during the instances of stress or anxiety. Once state of stress or anxiety is recognized, the vibrator module on the contact surface oscillates in a definite remedial pattern according to the real-time physiological condition of the user. During the real-time guided stress management application, the vibrator oscillates with 7.5%-25% higher ON time to indicate breath-out demonstration and 7.5%-25% lower OFF time to indicate breath-in demonstration. The ring apparatus has a button on the outer top surface and a button on the lower bottom edge surface. The button on lower surface is used to operate the functional modes of meeting mode, work mode, fitness mode, sleep mode and others. The button on the top is utilized for operating the telephonic calls, wireless synchronization facilities and other functionalities. A gesture sensor is embedded on the user facing front surface, which is used as an interactive gestural means for accessing and navigating through the presentations and the applications. Additionally, the button inputs are used to access presentations and applications.

Seventh Aspect

The seventh aspect of the invention puts forward a multifunctional medical instrument for limb attachment or forehead telemetry. The electronics components and sensors of the hardware are packaged in a heat regulating case, according to the fourth aspect. The bio sensors are arranged on the contact surface of the case of the telemetry apparatus. A soft stretchable cloth attached to the main packaging case, contains adhesive surface and stickable surface end tail pads. The adhesion action between the adhesive pad and stickable pad, and the stretchable cloth belt are utilized to fasten the apparatus steadily on the sensing spot. The foam base situated on the contact surface and surrounding the biosensors, is utilized as a mechanical means to reduce movement noise in the bio-signal recording. The other utility of the disposable foam includes improvement of the clinical hygiene and reusability efficiency.

Eighth Aspect

The eighth aspect of the invention illustrates an auxiliary wellness management and clinical monitoring device, that can be attached to an exercising machine. The essential sensors and electronics components of the apparatus are packaged in a heat regulating case, as per the fourth aspect. The biosensors are assembled on the contact surface of the case of the telemetry apparatus. The heat regulating case is attached to an expandable machine gripping holder, and this expandable holder is used to attach the device to wellness instrument (like exercise cycle, treadmill, bike etc). The expandable holder grips the exercise machine and the keep the apparatus steady on the sensing spot. A foam base on the contact surface around the bio sensors, is utilized to reduce movement noise in the bio-signal recording.

Ninth Aspect

A bracelet or smart band embodiment for telemetry and general wellness management is presented in the ninth aspect of the invention. The optical apparatus, electrical spectrometer and non-contact temperature sensor are placed on the contact surface of the device. The casing of the device contains the accelerometer, sensors, wireless antennas, power supply unit, battery, digital chips, Analog ICs, microprocessor, integrated circuits and other necessary electronic components. The device has an integrated low-pressure mini-cuff, which automatically inflates to the detect the resonant compression point for blood pressure calibration. A mini-touch display is placed on the top surface of the apparatus, which is used for operating the apparatus, accessing in-built application, and viewing the essential information (such as medical information, health data, bio-signals, general wellness data, etc). A set of Red and Green indicator LEDs are embedded on the top surface near the display. The indicator LEDs automatically blinks to guide the user during the instances of psychological stress or anxiety. During the recognized state of mental stress, the red indicator light flashes at the detected neural activity, and the green indicator light flashes at a definite assisting pattern. The green indicator light blinks with a 7.5%-25% higher ON time to indicate breath-out demonstration, and 7.5%-25% lower OFF time to indicate breath-in demonstration. A mode indicator light denotes different operating modes and other functional status of the apparatus. A trigger button placed on the top surface is used for operating the device, accessing in-built application and utilizing other functionalities. The device has a wireless synchronization button for synchronizing the data and device with accessorial devices.

Tenth Aspect

In the tenth aspect, a live multi-functional telemetry instrumentation is elucidated. The live wireless clinical monitor comprises of a cuff packaged with biosensors and a base station packaged with other essential electronic components. The biosensors of electrical spectrometer, optical spectrometer, accelerometer and non-contact MEMs/NEMs temperature sensor are arranged and packaged inside an inflatable mini-cuff. In the presence of user, the cuff automatically inflates to detect the resonant point for blood pressure calibration. The electrical cord of the instrument is used as the wired method to the attach the base station and the cuff. A slate sized touch display is assembled on the wireless base station for accessing and viewing live medical signals, patient history, patient's physical activities, other clinical information and health data. The touch screen is as well utilized to operate the device and access the in-built application. A wireless synchronization button and a power button is embedded on the wireless base station. The wireless synchronization button is used for synchronizing the clinical recording, patient history, medical information and other important information between the telemetry apparatus and computer server/accessorial mobile apparatus. The power button on the base station is utilized as the means to reset the medical analysis, power on/off the device and access other in-built functionalities.

Eleventh Aspect

According to the eleventh aspect, a smart wearable instrument for medical monitoring and daily wellness management is presented. The smart wearable comprises of a round case or rounded rectangular case, that holds the electronic components and sensors of the telemetry device. The biosensors, aligned in the blood flow direction, are placed on the contact surface, and a mini touch display is embedded on the top surface. The device is operated through the mini-touch display. The clinical information, health data, psychological stress, sleep data, daily diet pattern, fluid intake information, amount of expended energy, active step/stride taken, and other lifestyle management data are displayed on the mini touchscreen. The mini display is also used to view and access real-time medical diagnostic signals, recorded information, therapy techniques, automated cardiac activity guide, wake-up alarm, in-built applications and other important information. Push buttons and potentiometer integrated crown, are embedded on the parallel to side surface and perpendicular to the electronic board. The push buttons and crown are utilized to access different device applications, to calibrate the apparatus and to switch between the different functional modes. The crown integrated with potentiometer is used as the electronic embedded method to navigate through the application in row and columns, and to operate other apparatus functionalities. The rounded corners or round contact surface is used to evade the cuts, that may otherwise occur due to sharp edges.

The home screen of the smart wearable displays daily health management information and a motivational quote. The background motivational quote application is intended to psychologically improve the spirit of the user. The smart wearable apparatus comprises of applications for real-time clinical monitoring, cardiac training, tracking Emotional Index, persona oriented psychological stress management, sleep management and other lifestyle/wellness management information.

During physical training, the cardiac training application automatically tracks training intensity, rest period, training period, cardiac rate, training phase and other important health data. The automated cardiac application also has essential information to guide the user with health improvement and recovery. The push buttons are utilized to trigger begin, pause, un-pause and reset in the cardiac activity training application. The touch display, push buttons and the crown are used to access other functional command in the cardiac activity training application.

The real-time stress information is displayed in the emotional index (EI) meter and in a persona-oriented stress management application. The psychological stress management application displays EI meter, stress threshold information, stress management information and work schedule management features with priority stickies. The EI meter displays persona-oriented stress information, which has been extracted from the previously marked stress data points. The touch display and push buttons are used to mark unwanted stress levels.

The sleep application automatically tracks sleep and displays sleep period, sleep health, motivational wake-up quote and other sleep related information. The sleep application also includes a user configured wake-up alarm.

The medical application shows real-time information and recorded data on pulse rate, oxygen saturation, respiratory rate, body temperature, average pulse rate variability, neural activity balance, blood pressure data and blood glucose levels.

Twelfth Aspect

In the twelfth aspect, a parallel computational network is provided. The parallel computational network enables the computation with much higher speed and efficiency, while keeping the complexity low. The network of parallel computation network comprises of internal microprocessor, external server computers, accessorial mobiles devices, external computers and other connected local devices. The external servers are used for executing computational process, and as well as for remotely storing the information. The accessorial mobile devices and other synchronized devices are also used to compute and store the information. The network of parallel computing devices are accessed through wireless methods of 'WLAN, BLE, GSM' and through other possible modes of communication. Whenever necessary, stored information and computed results are communicated between the telemetry apparatus and network of devices.

Thirteenth Aspect

The thirteenth aspect of the invention presents a real-time medical monitoring and wellness data processing system.

Initially, the recorded bio-signals passes through an accelerometer-based noise filtering process. The real-time feedback of the angle calibrated accelerometer signals are sampled in a normalized form, and the bio-signals are processed through 50/60 Hz digital filter to remove the power line noise disruption. The processed bio-signal and accelerometer signals passes through repetitive adaptive filter and other computational steps. This process removes motion noise from the bio-signal. Then the first order noise free signal further passes through a series of banked filters, low pass filter and correlation computational step for removing the rest of the noise.

The filtered signal is further analyzed through time domain and frequency domain peak processing methods to precisely compute real-time avg. pulse rate, instantaneous heart rate, hr tachogram and neural Activity balance coefficients of σ1, σ2, σ3, σ3/σ1, σ3/σ2, σ2/σ1. The set of computed data and raw signals are sampled at a rate of 7.5 Hz, 15 Hz, 30 Hz, 100 Hz, 125 Hz, 240 Hz, or 1 KHz. The sampled data is processed using a fast response analysis method, and the processed sampled is condensed utilizing a matrix compression method. The sampling and compressed data selection method significantly decreases computational effort needed to analyze the entire waveform. The compression is followed by an analysis to calculate continuous heart rate and average pulse rate. The signal ratio between the oscillating peak and stationary peak of red and Infrared bio sensor, in the form of signal derivate is taken, to determine the oxygen saturation ratio.

The signal is passed through digital filters of High-Frequency(HF), Low-Frequency(LF), Very Low Frequency (VLF), Meyer pass filter and Ultra-low Frequency(ULF) signals. Then, the relative power under each frequency spectrum is calculated to assess neural activity. The derived coefficient of $P_1$, $P_2$, $P_3$ and $P_4$ are evaluated through a set of computational steps to determine the overall health of Autonomous Neural System and cardiac system.

The noise-free signals are further analysed in different spectrums to compute respiratory rate, avg. breathing rate and meyer wave signal. The pulse signal is processed to decouple the noise artefact free signals into different wave signals. The pulse wave is iteratively decoupled to obtain breathing signal, and the derived signal is processed for peaks to determine the respiratory rate. The analysed signal is mathematically operated for computing average breathing rate, continuous respiratory rate and breathing rate. A similar analysis is utilized to decompose the meyer wave signal and its related parameters.

The user calibration input, extremum of optical data with respect to time and recorded data are analyzed for extracting the continuous blood pressure and diastolic pressure values. The dual sensor configuration is utilized to estimate momentum loss in the blood vessel, mean pressure and the systolic pressure. The recorded heart to device reference length is used in the cuff-based apparatus to accurately measure the mean arterial pressure.

An automated method to calibrate the heart to device reference length is as well provided. The value of 9-axis accelerometer sensor signals are recorded at different instructed arm positions of bent arm, fully stretched arm, lifted arm and straightened down stretched arm. Using the recorded sensor data, the forearm and Arm length are calculated, through which average heart to device reference length is generated.

The Near-Infrared bio sensor signals and other optical signals of Green, Infrared and Red signals are processed to compute Blood Sugar Level. Initially, the input on the blood sugar level is taken for sensor calibration. The Green LED, Infrared LED and Red LED response signals are processed to remove the losses in the Near-Infrared signals, due to the blood flow fluctuations, tissue absorption and other coherent errors. The Processed Near-Infrared data is correlated and fitted over various patient's/user's/physician's inputs to calibrate the Near-Infrared biosensor. The continuous blood glucose levels, blood sugar levels, hyperglycemia and hypoglycemia are computed from the calibrated data. In case of chronic medical condition, the system automatically reminds the patient for medication, or alerts the user, user network and the physician network about the diagnosed health condition.

The real-time system further comprises of an automated method to record various stages of the sleep cycle, and to recognize obstructive sleep apnoea. The accelerometer values are initially evaluated for state of sleeping or dormancy, and the real time physiological signals are compared to wake or activity physiological data. After the verification process, the real time physiological signals of avg. breathing rate, systolic blood pressure, diastolic blood pressure and instantaneous Heart Rate signals are processed for tracking the time periods of non-rapid eye movement and rapid eye movement sleep cycles. Then a series of computational steps is applied on the instantaneous pulse rate data, analyzing for beats per minute difference in definite time intervals, for recognizing the sleep apnea condition. Then, the respiratory signal pattern validation step is utilized for verifying the state of sleep apnea and sleep cycle. The sleep apnea condition and its time-period are recorded in the system.

Fourteenth Aspect

The fourteenth aspect of the invention provides a life-support system, which automatically recognizes daily activity, pre-clinical emergencies and records one's state of well-being. The recorded biosensor data, motion sensor data and wireless antennae are processed to evaluate the various postures, user training information, rest period, activity period and state of fatigue. The system further learns and records the various postures, movement data and activities of the user (such as (of sitting, standing, number of steps, number of strides, lap count, speed, training phase, resistance training, cycling, driving and more). The life-support system records subjective psychological stress points and identifies the stress state of the individual based on the computed vital bio-signal and electrical spectrometer signals. If the state of psychological stress is detected, the system automatically guides the user to a breathing stress management technique or other stress management methods. The system consists of automated clinical emergency life support method to detect the risk of CHF attacks, hypoxia, hypothermia, hypoxemia, blood poising, blood loss, hyperthermia, unusual ventricular activity, heat stroke, nervous breakdown and other chronic conditions. If a life threating or chronic condition is recognized, the apparatus alerts the user's network and life support network. The invention also provides an automated power saving method. The real-time system comprises of a low powered method to recognize the presence of the user based on the estimation of the realistic bio-response data and movement data. The recognized user presence is utilized to automatically power on, power off or restart the device.

Fifteenth Aspect

The fifteenth aspect of the invention presents the accessorial software application and accessorial mobile apparatus, that is attached to the telemetry apparatus. The accessorial software application of the accessorial mobile apparatus comprises of components for daily health management, clinical condition management and device application management.

The personal fitness management component of the software application is utilized to log and track personal information, routine health check-up data (like weight, height, basal metabolic index, basal metabolic rate, workout target), physical exercise activities and nutrition intake. The application displays real-time and recorded health data of base heart rate, commuted distance and calories expenditure. A cloud synchronization button on the application is utilized to synchronize the data with the cloud services and share the data with professional practitioners.

The stress management component of the software application comprises of emotional index meter, stress management information, stress management progress meter and guided meditation components. The Emotional Index meter shows persona-oriented stress levels and it oscillates according to the neural balance. The stress management meter reports the progress on the stress management. As the stress meter reaches the threshold, the device directs the user to guided breathing/meditation method or to a social communication interface. A daily work management feature on this interface is used to schedule professional work activity with priority. The work management functionality is included as procrastination is an indirect counterpart cause of mental stress.

The sleep management component of the accessorial software application tracks sleep cycles, sleep period, NREM-REM cycle length and other sleep trends. The user can view and access the computed data and recorded log. On recognizing sleep disorders, a warning message regarding the disorder symptom appears on the user screen. The user can connect with physicians and health professionals through the sleep management interface.

The accessoral mobile device further comprises of an interface to monitor real-time information on pulse rate, oxygen saturation, pulse rate variability, neutral activity, breathing rate, body temperature, blood pressure levels and blood glucose levels. The computed real-time and recorded results are displayed on the screen along with access to the individual physiological signal wave form. The user can connect with medical and health professional through this interface. The medication tracker and reminder feature records the medication pattern and medication reminder. The device automatically alerts the user at the correct time for medication. The data on this interface can be shared on online platforms and with medical and health professionals through the data synchronization button.

Health network interface of the software application enables professional medical practitioners, dieticians, fitness instructors and other health professionals to interact with the patient/user. The health network is used by the professionals to guide the user with health and therapy practices. The health blogs, articles and classes can be accessed by the user through this component of the software application.

A daily health management component displays information on the number of active steps taken, sleep health, heart rate with oxygen saturation ratio and emotional index matrix. The background information on daily well-being can be accessed through the daily health management component. The progress and history of the user can be accessed by clicking on the history trend button of this interface. The work schedule can also be organized through this interface.

The ease of lifestyle organization interface of the accessorial software application has the functionalities to synchronize, install and manage $3^{rd}$ party and native applications on the telemetry mobile apparatus.

BRIEF DESCRIPTION OF THE ARTWORK

Figures 16A, 16B:
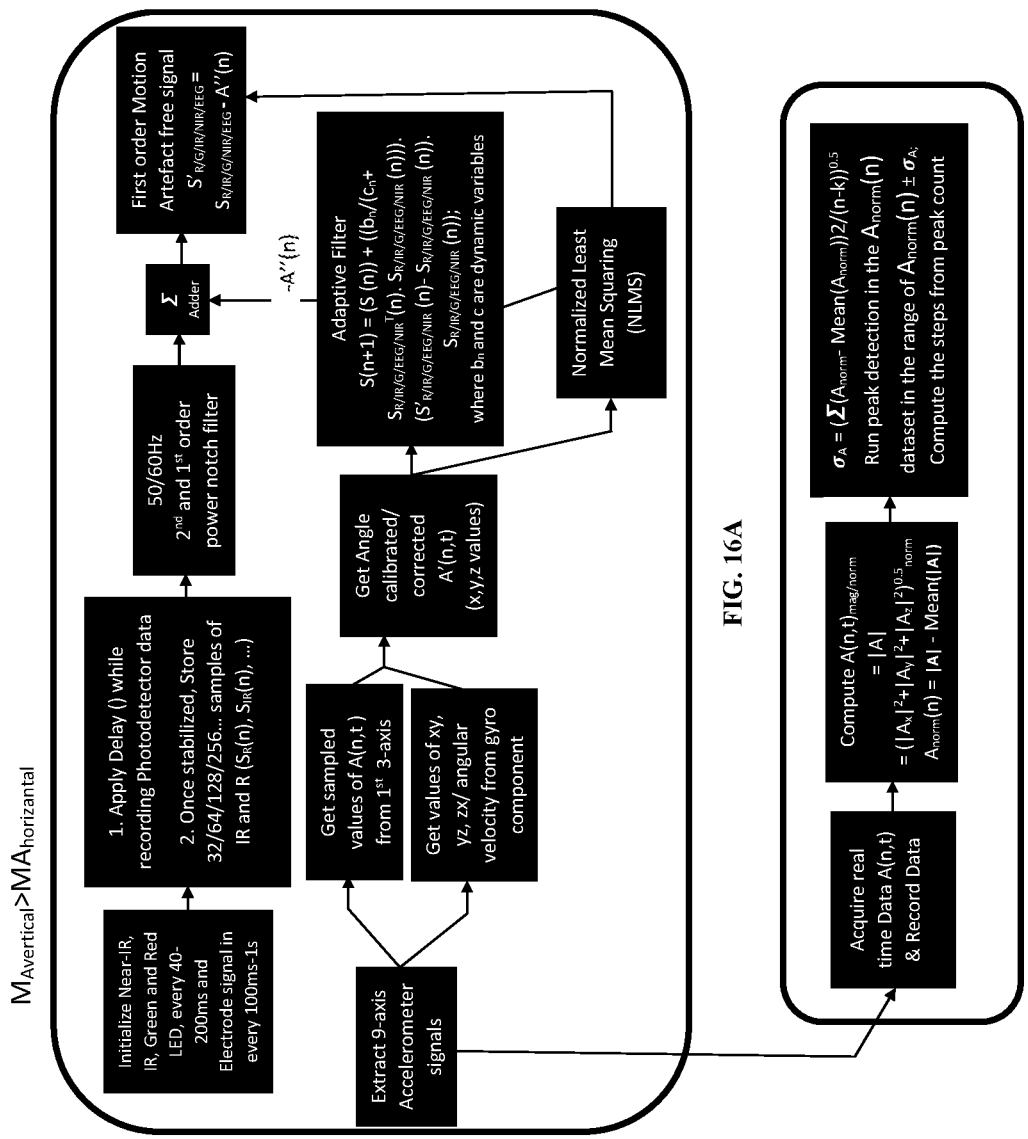
Figure 17:
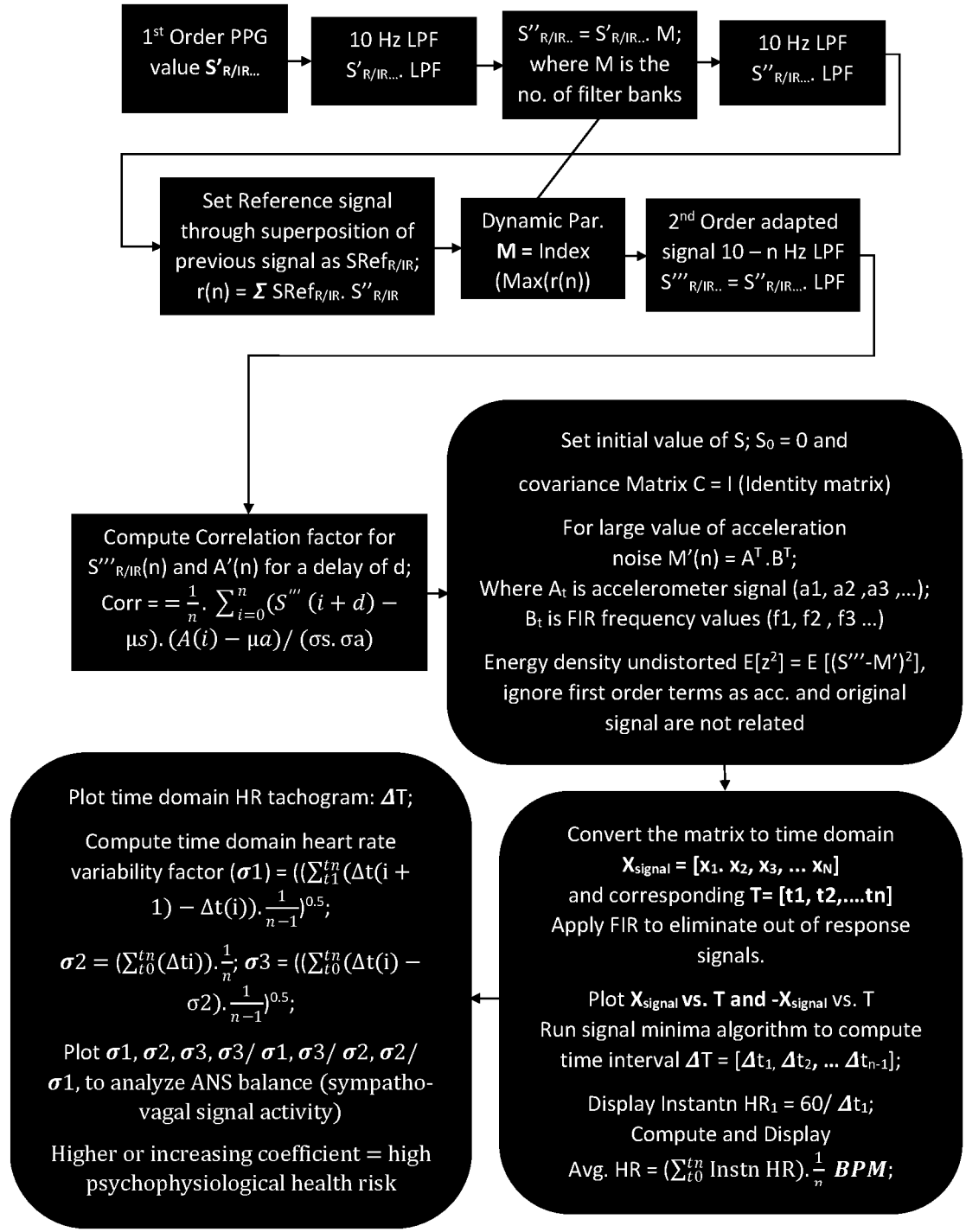
Figure 18:
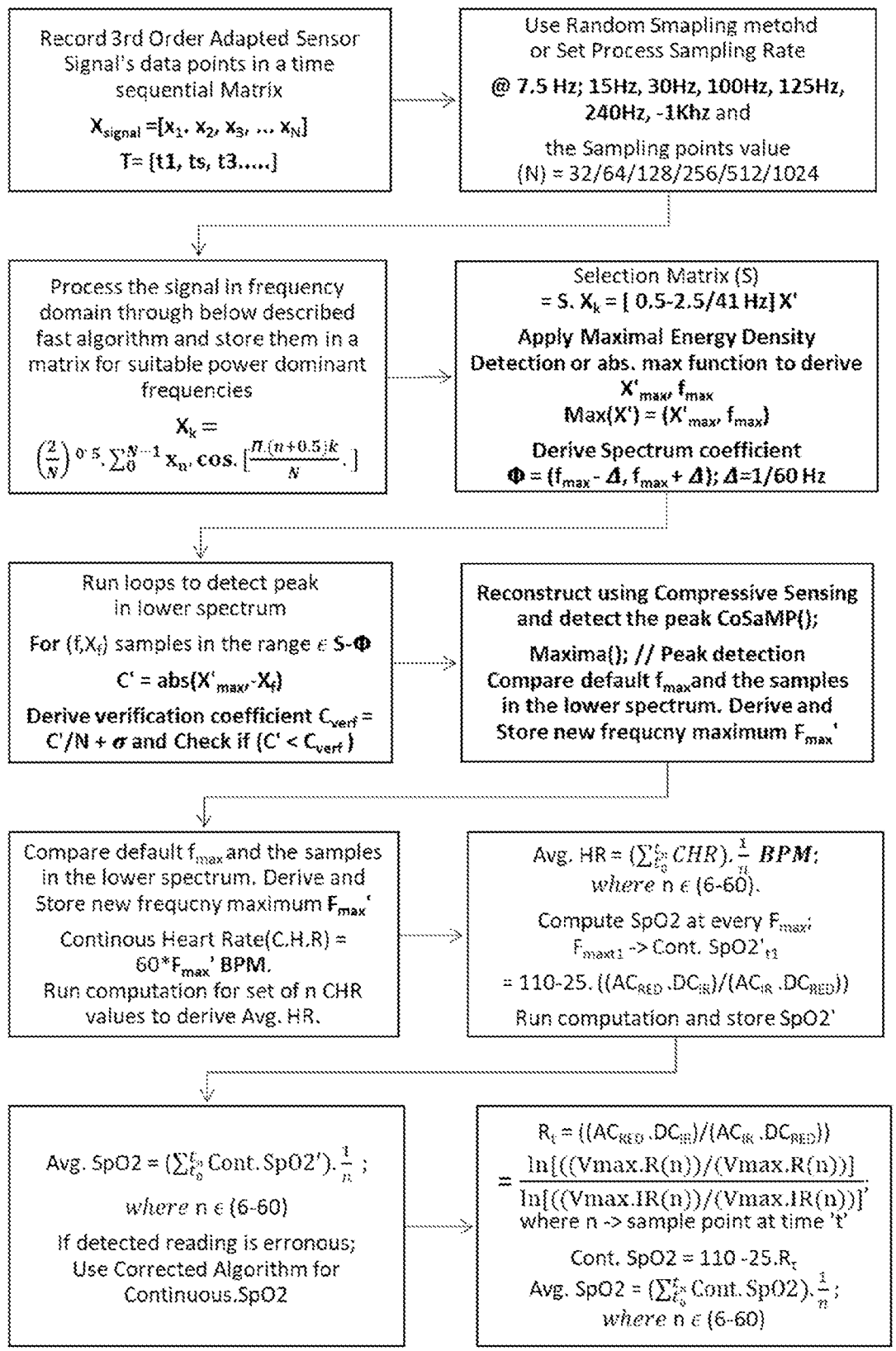
Figure 19:
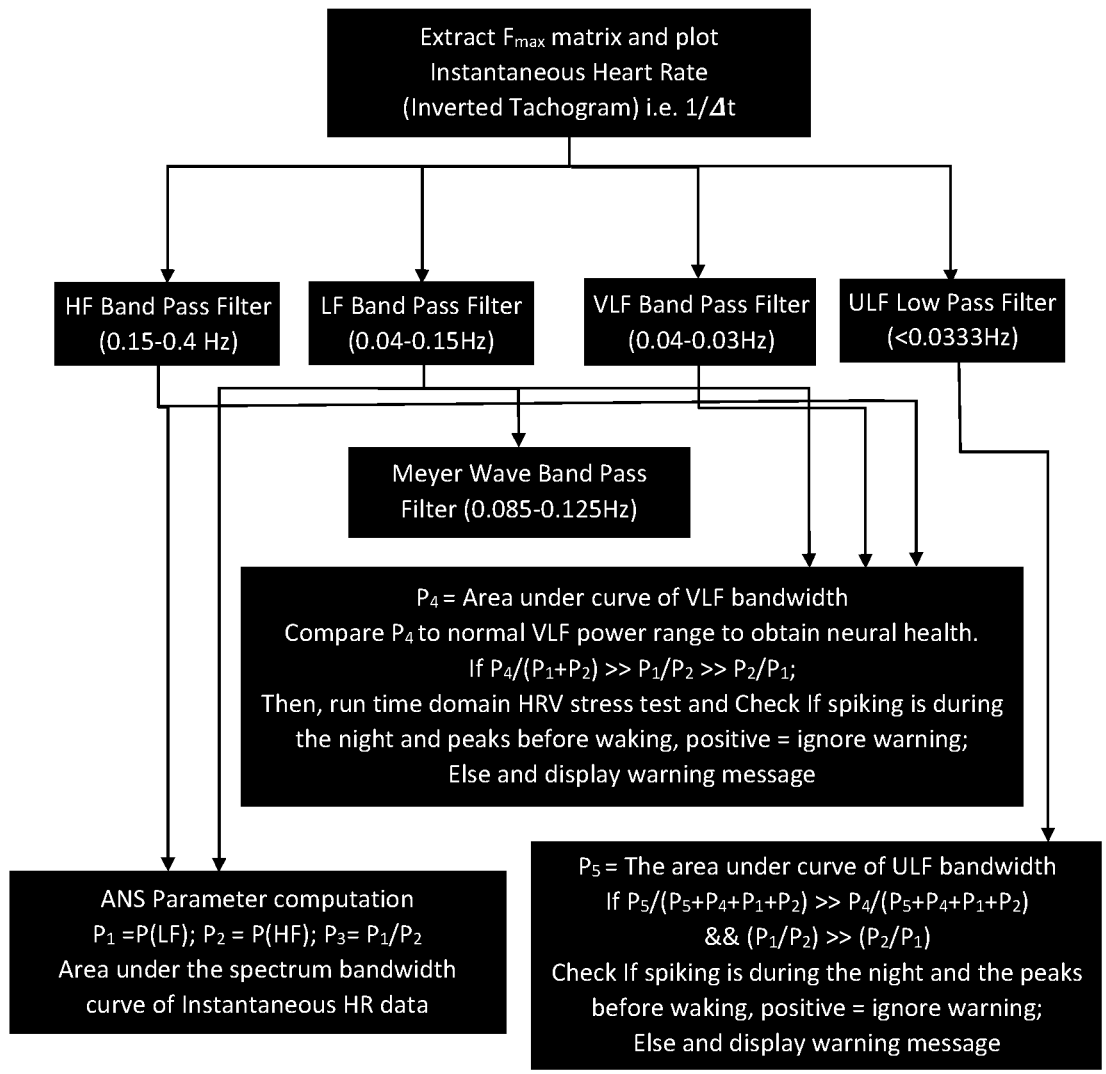
Figure 20:
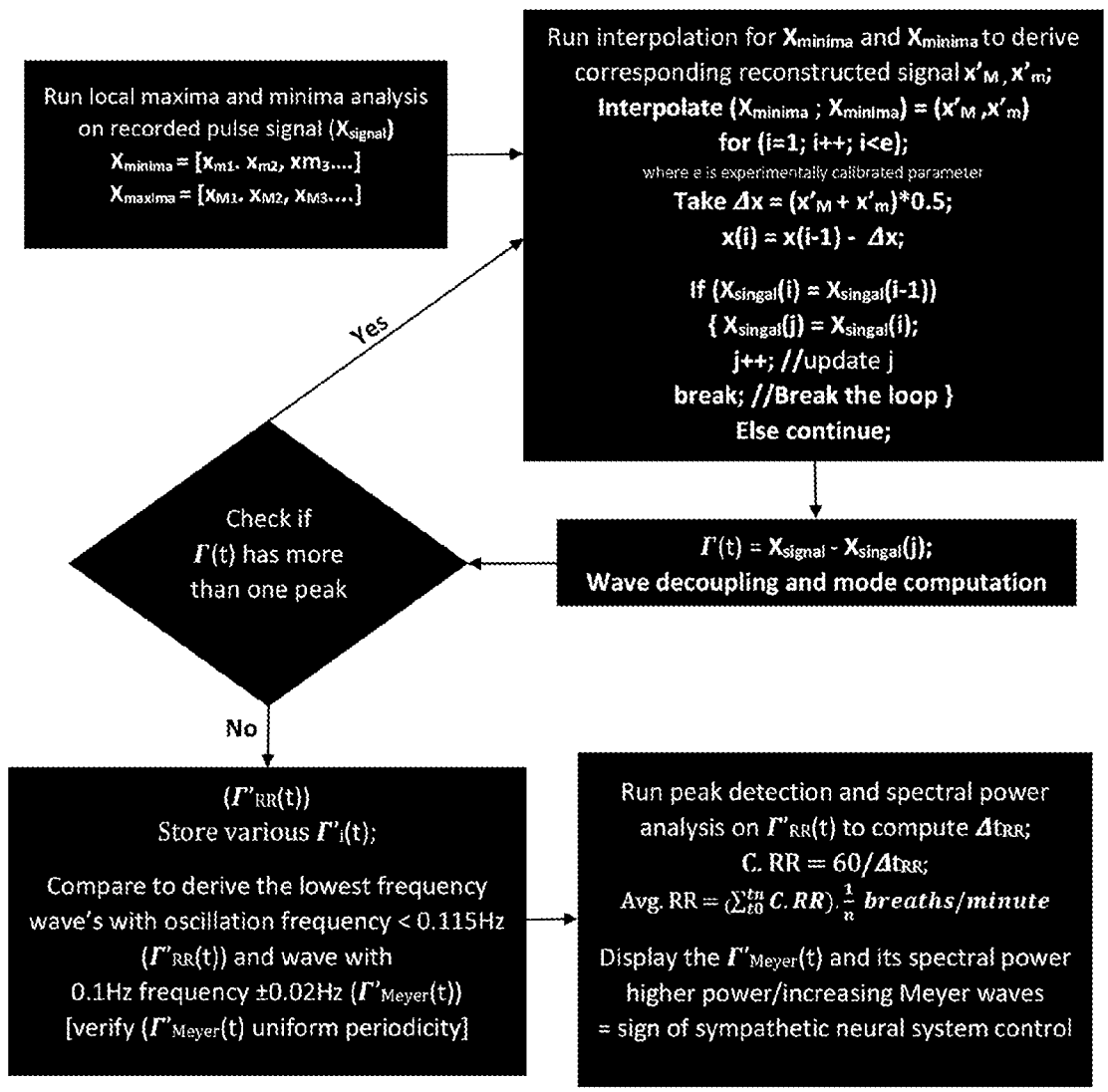
Figure 21:
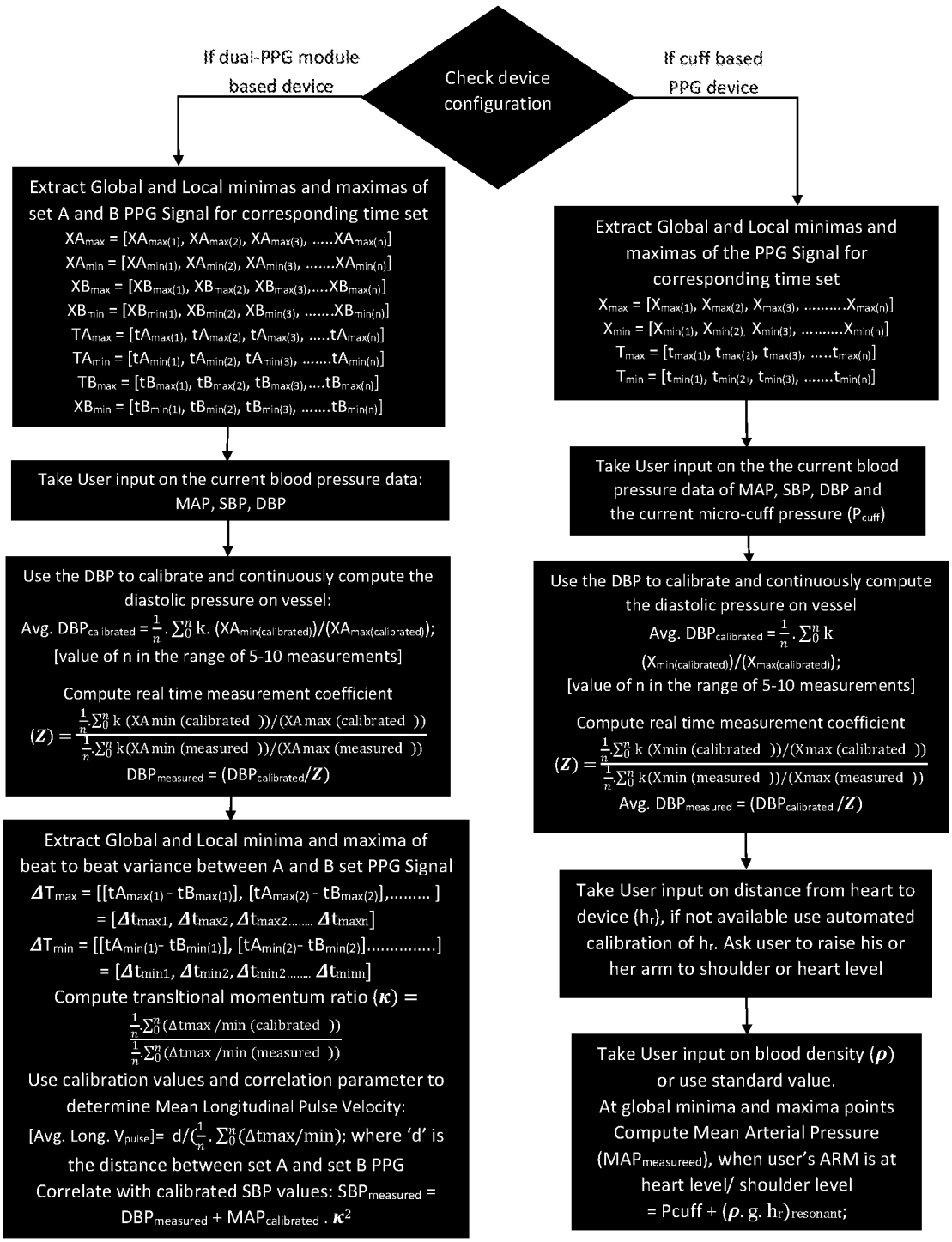
Figure 22:
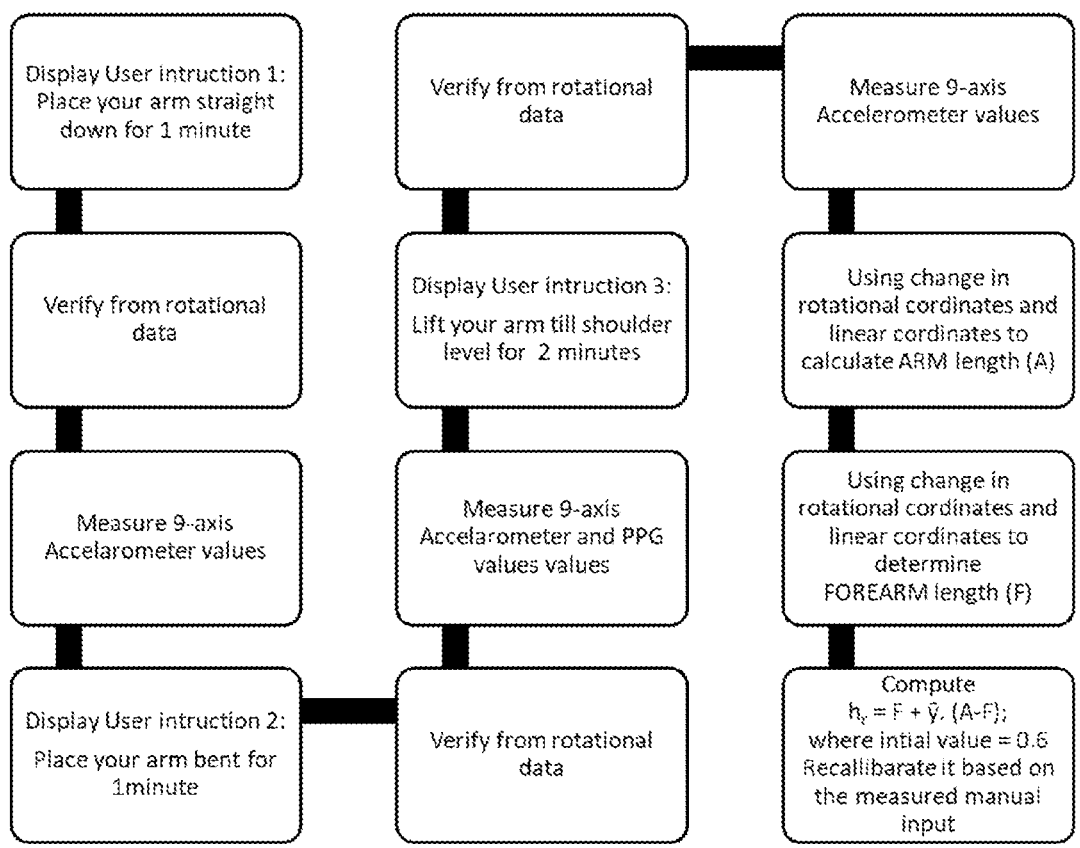
Figure 23:
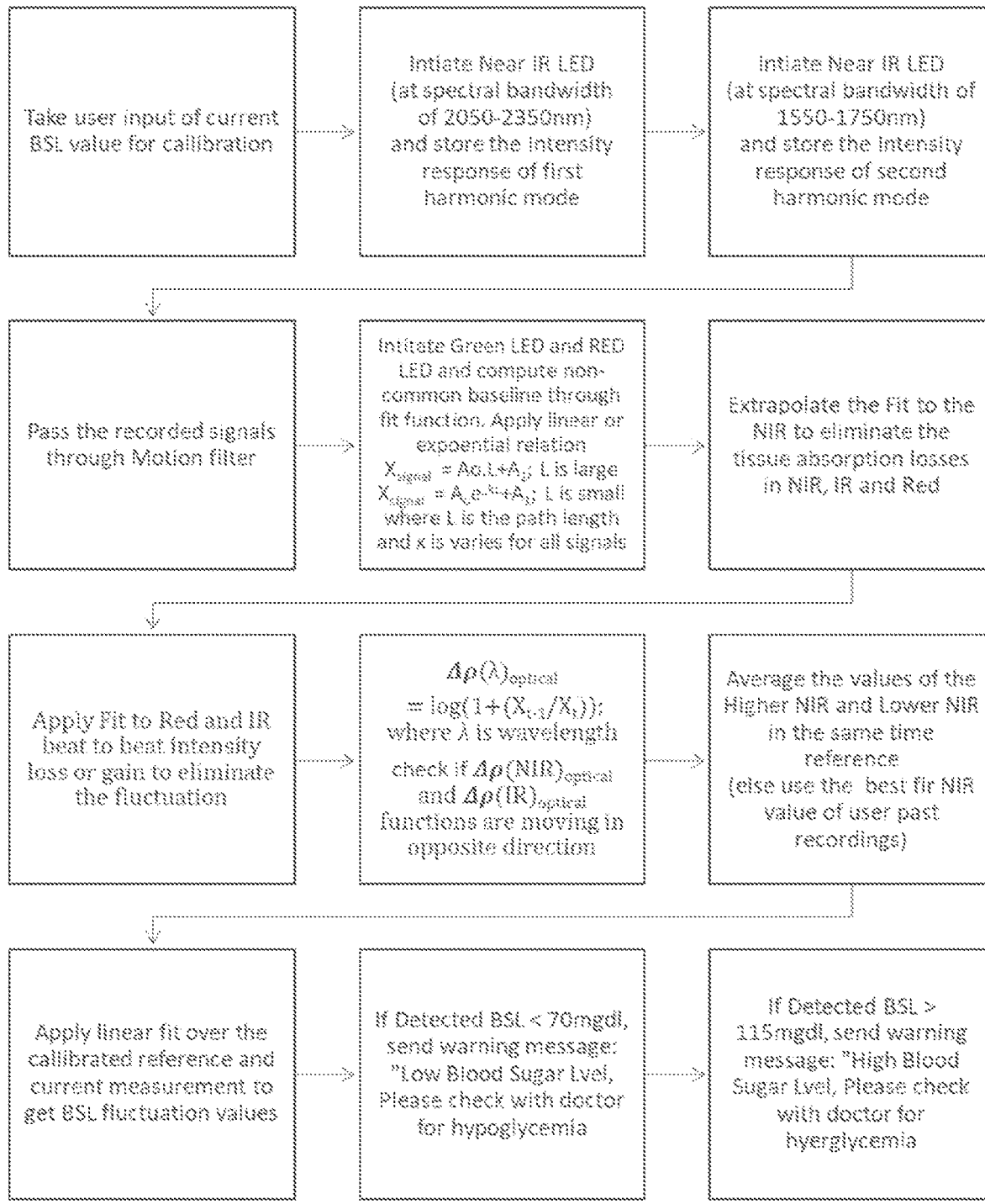
Figure 24:
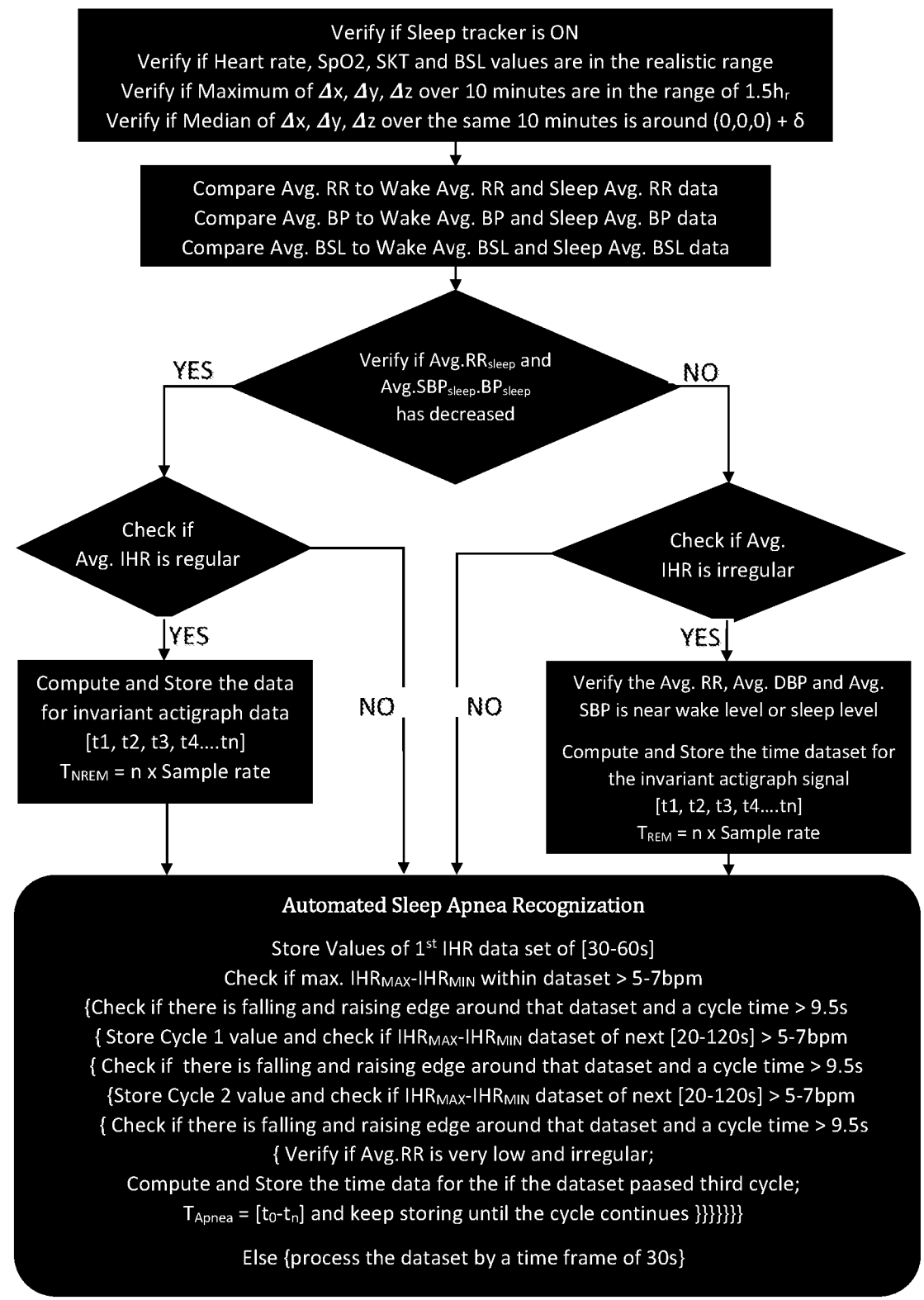
Figure 25:
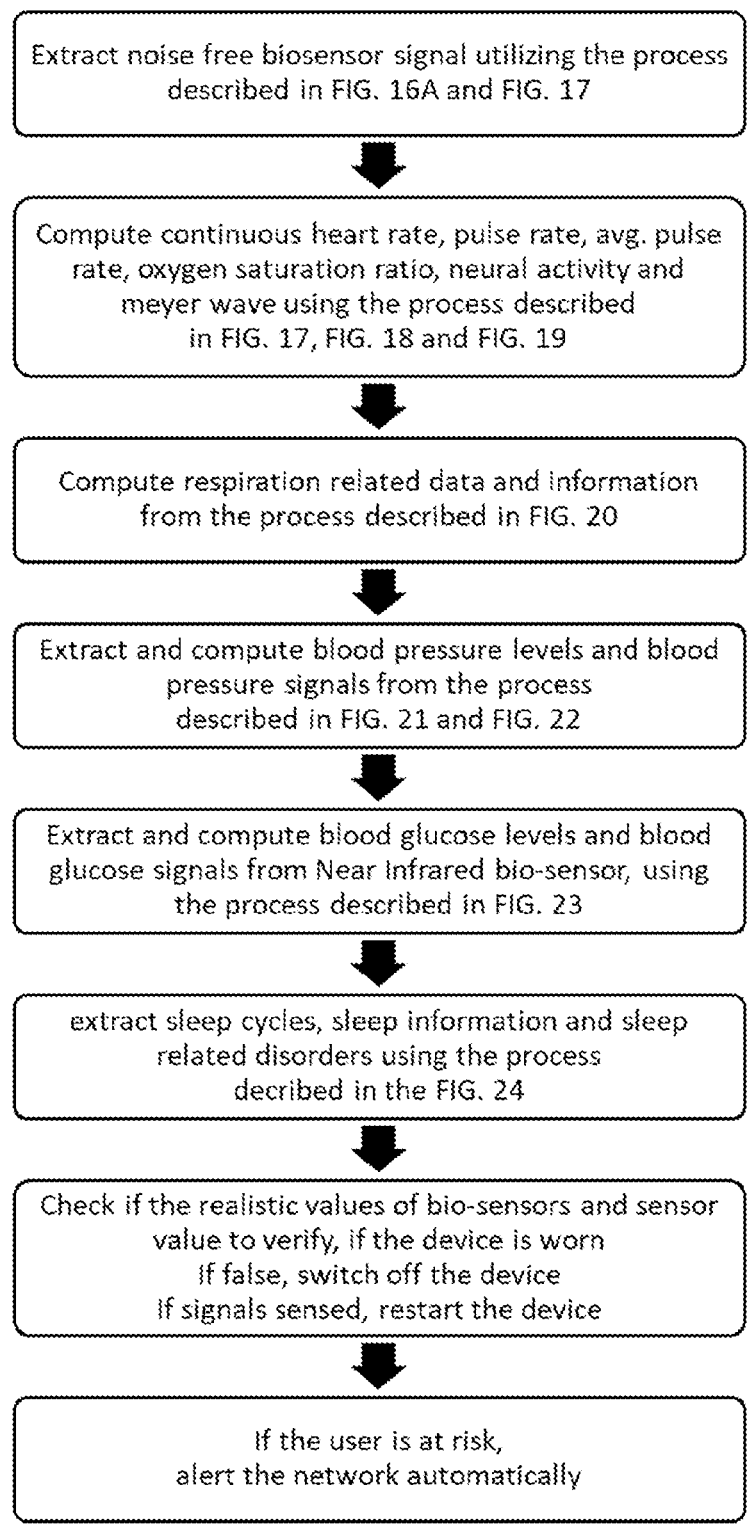
Figure 26A:
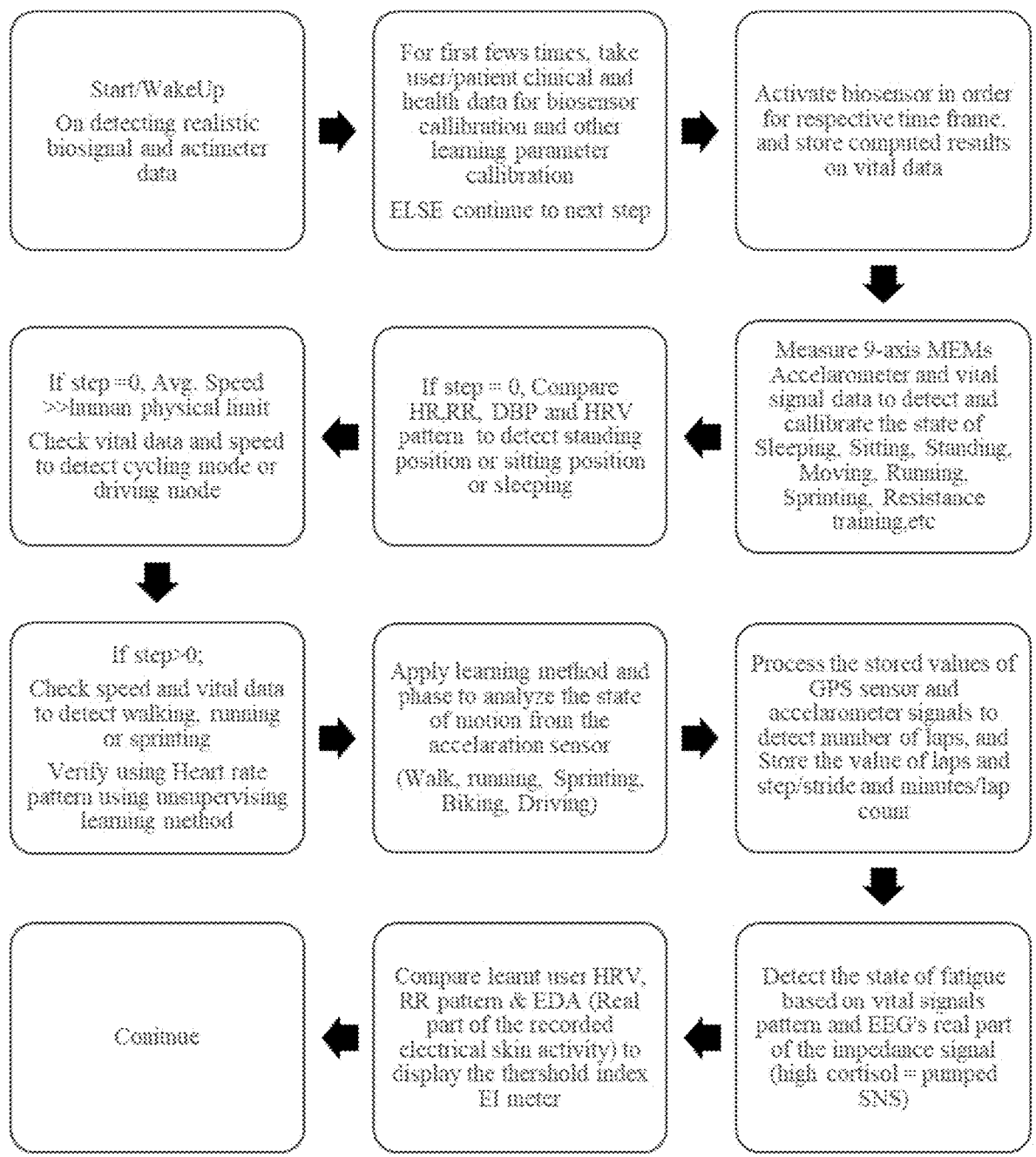
Figure 26B:
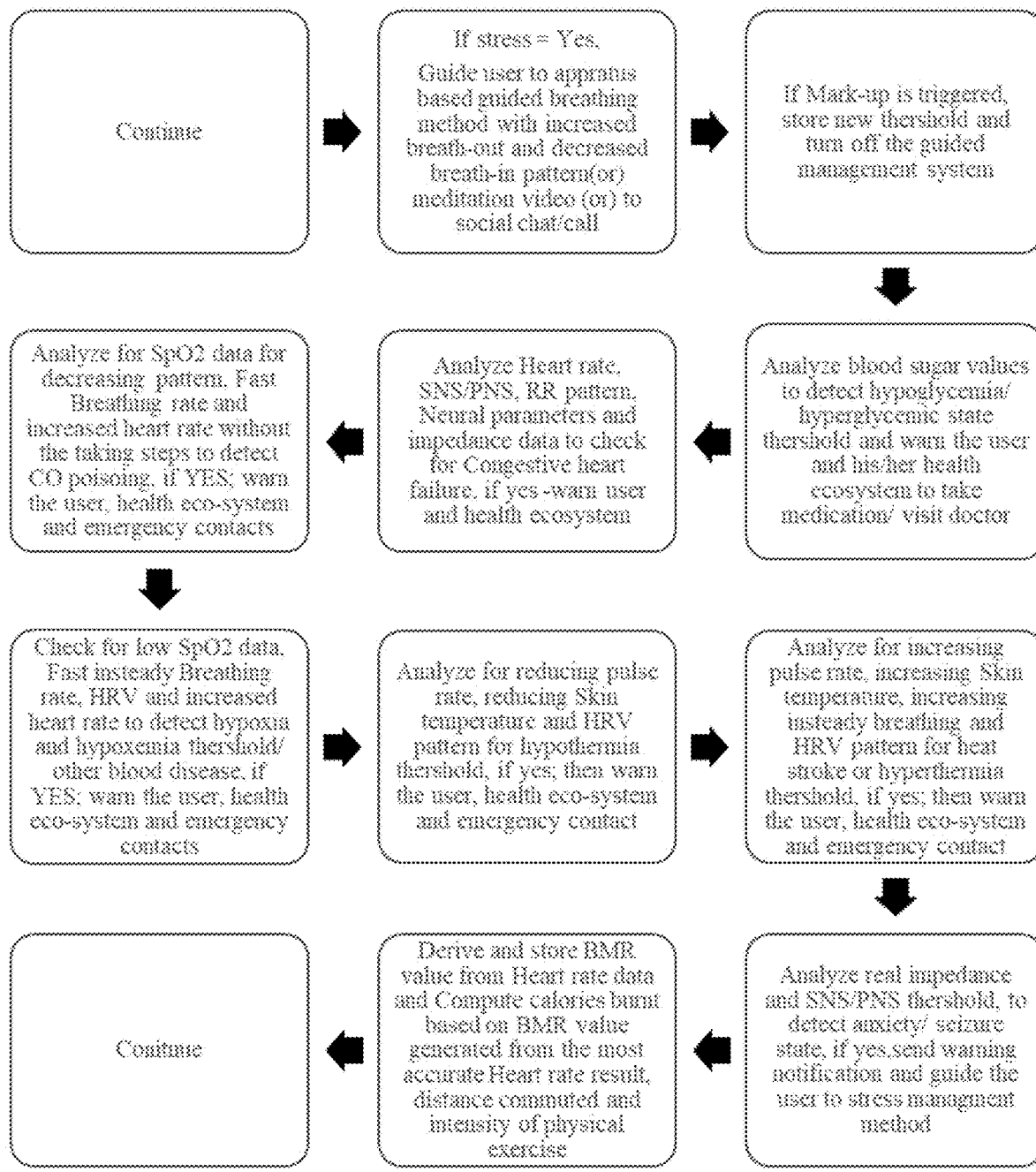
Figure 26C:
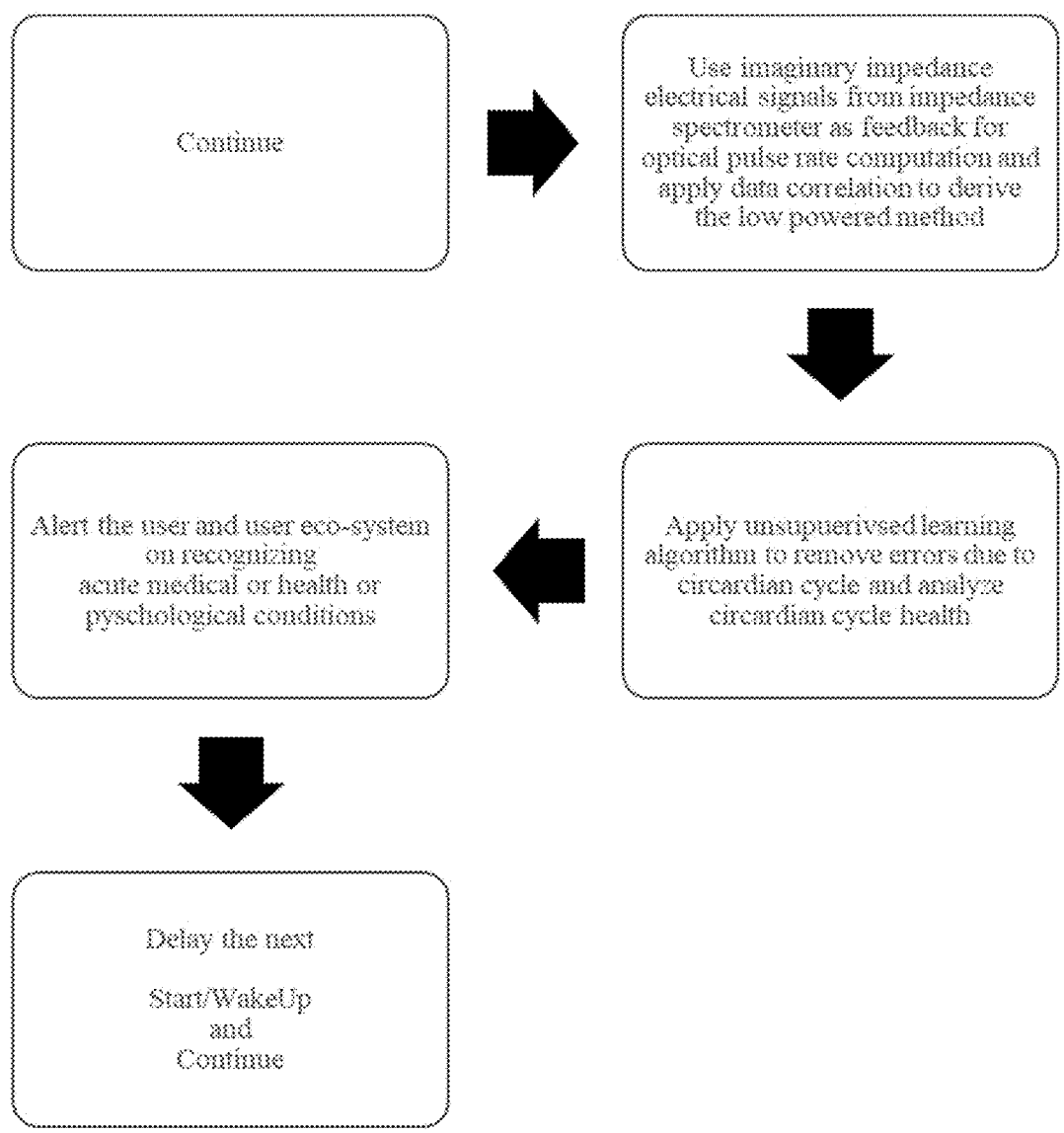
Figure 27A:
Figure 27B:
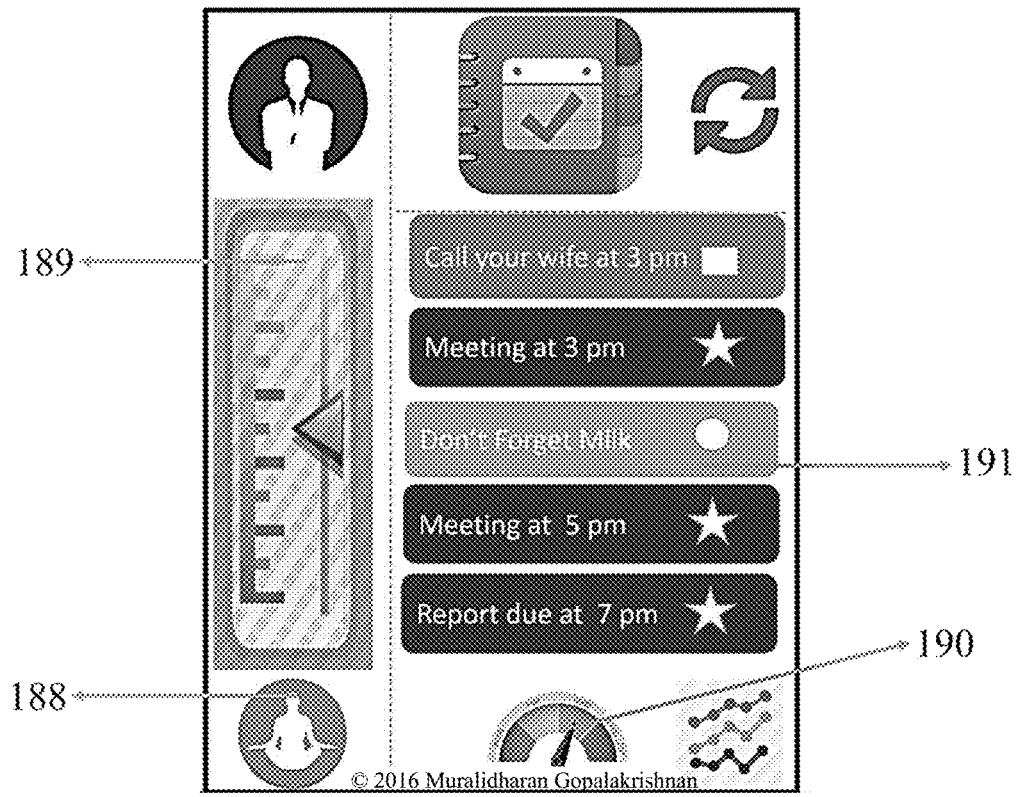
Figure 27C:
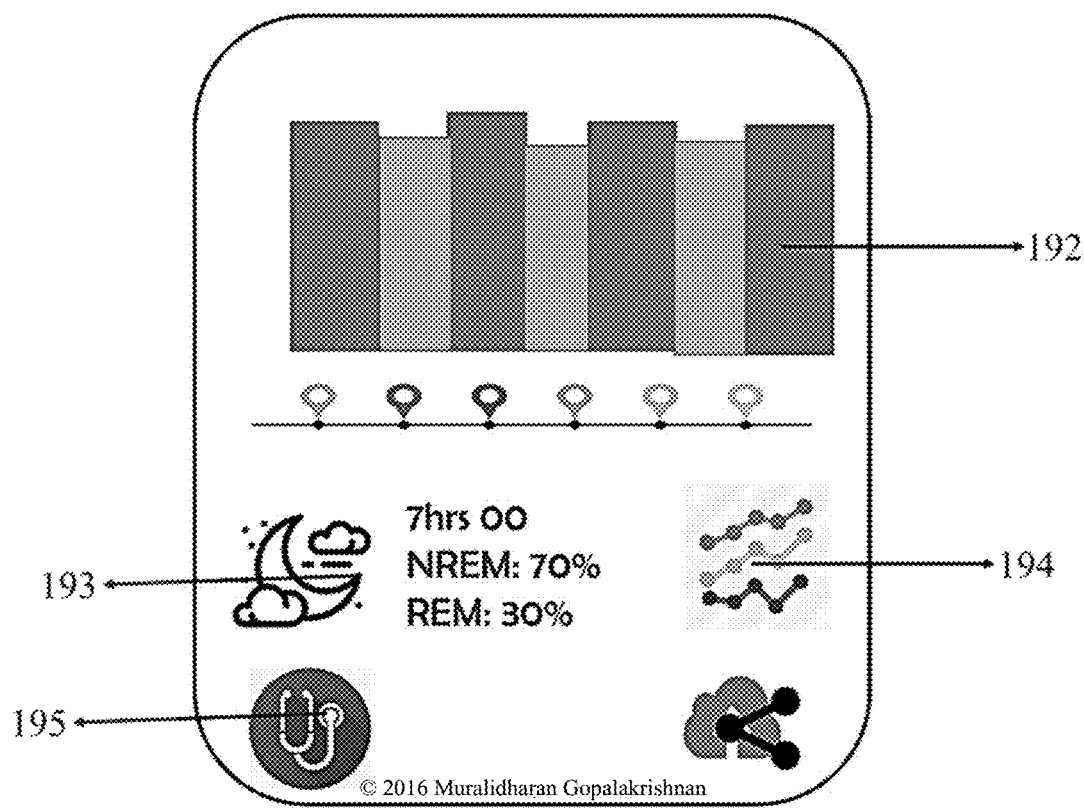
Figure 27D:
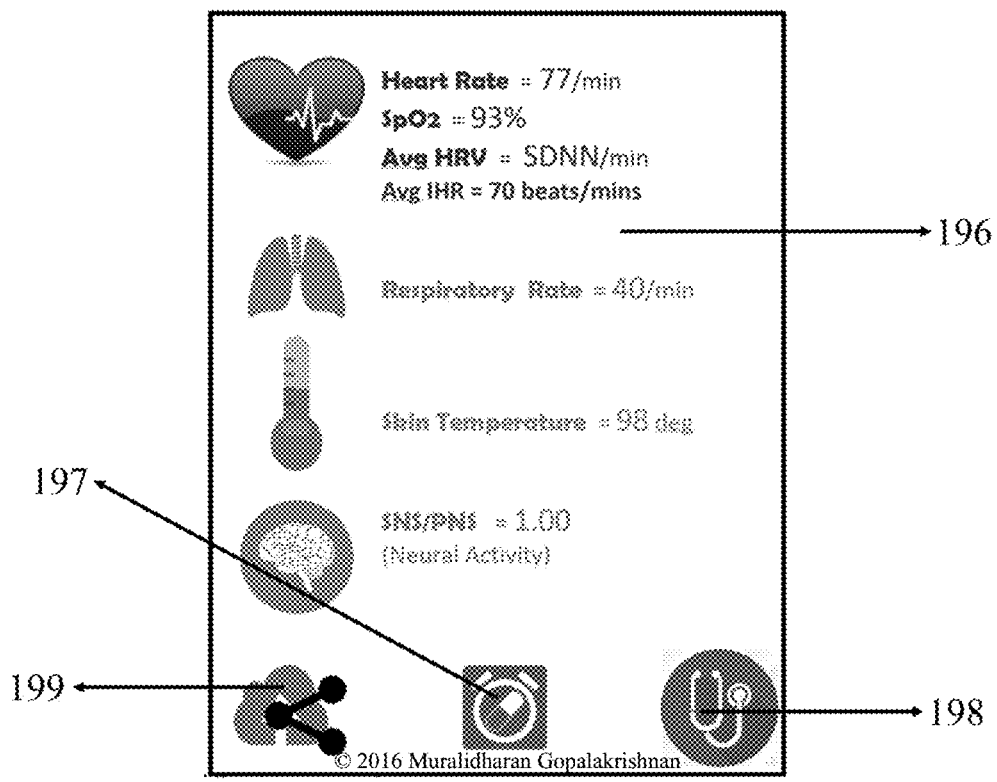
Figure 27E:
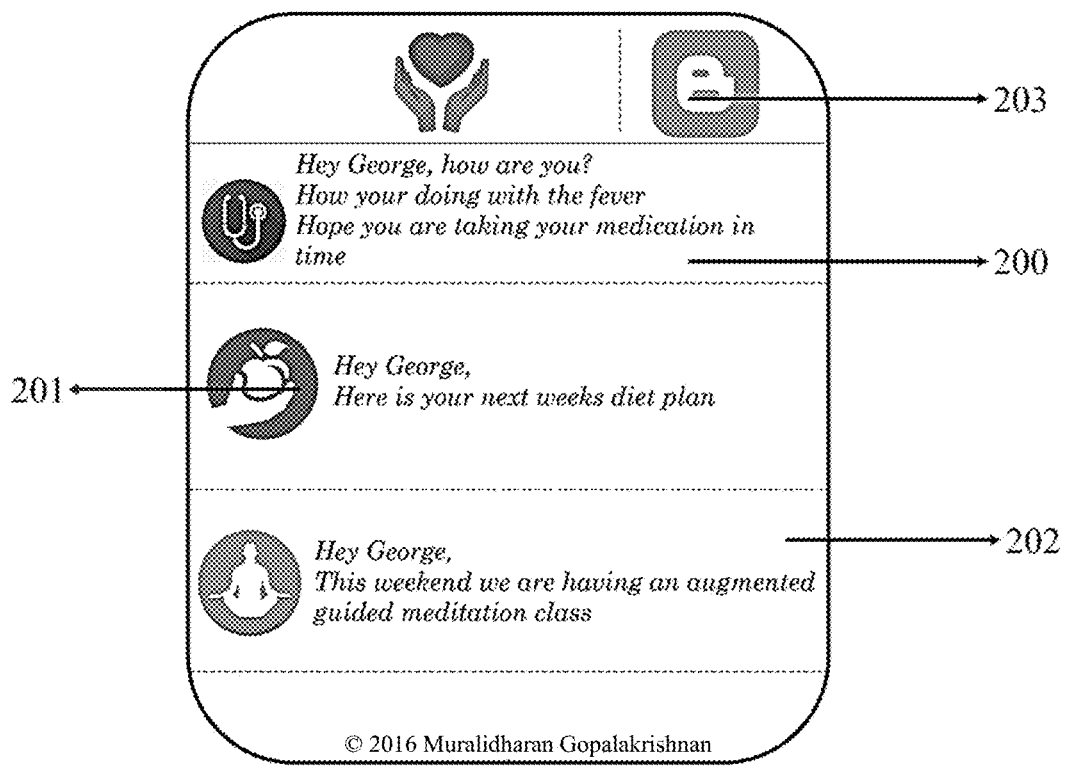
Figure 27F:
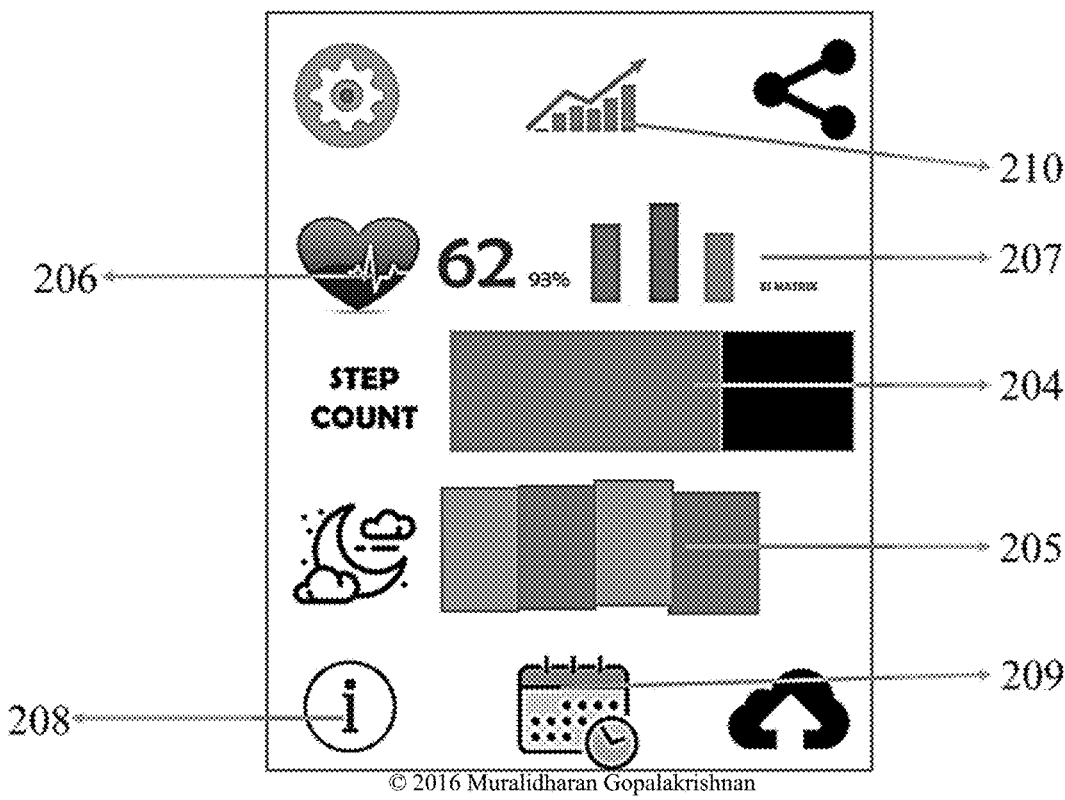
Figure 27G:

FIG. 16A address the processing method and flow chart to remove the motion disruptions from Input bio-signal using accelerometer signals as real-time feedback;

FIG. 16B describes accelerometer signal computation method to record the movement data set;

FIG. 17 is the flow diagram of a low powered computational method to process the first order motion artefact free bio-signal for further removing noise and for calculating Avg. Heart Rate, Instantaneous Heart Rate and Neural Activity balance;

FIG. 18 describes the flow-chart of a low powered real-time bio-sensor processing method to compute the Continuous Heart Rate and Oxygen Saturation Ratio;

FIG. 19 shows signal analysis methods to extract the parameters related to Neural Activity, respiratory activity and Meyer wave activity;

FIG. 20 shows the real-time computational method to compute breathing signals and meyer wave signals;

FIG. 21 shows the computational flowchart to measure blood pressure signals from optical signals and calibrated data;

FIG. 22 illustrates the automated method to calibrate anatomical measurements necessary for micro cuff-based blood pressure measurement;

FIG. 23 describes the Near-infrared optical biosensor-based method to extract blood glucose levels, and blood glucose thresholds;

FIG. 24 is the flow diagram of the computational method to recognize sleep cycles and the risk of Obstructive Sleep Apnea Disorder;

FIG. 25 shows a basic flow diagram of multi-functional medical device that computes medical information using the previously described computational methods;

FIG. 26A, FIG. 26B and FIG. 26C describe an automated life-support system that automatically recognizes postures, user activity, acute clinical conditions and the state of well-being, and automatically alerts the user eco-system on detecting health risks;

FIG. 27A shows the accessorial software application that displays important logged and computed information on user's or patient's heath;

FIG. 27B shows the accessorial software interface for stress and work management;

FIG. 27C shows the accessorial software to monitor sleep patterns and sleep health;

FIG. 27D shows the accessorial software application to monitor vital bio-signals, and it also includes other functionalities to manage medical conditions;

FIG. 27E shows the accessorial health platform software interface for connecting with health network and professional practitioners;

FIG. 27F shows the user application interface for tracking daily health and for well-being management; and FIG. 27G shows the application interface to install and manage applications on the mobile apparatus.

DETAILED DESCRIPTION OF THE INVENTION

Comprehensively, the disclosure can be utilized and perceived in various applications that include clinical instrumentation, portable medical device, general wellness management technology and other forms of smart health tracking auxiliary devices. The principle of the described invention is not intended to limit to the specific device or instrumentation application. The disclosure can be chiefly classified into live clinical diagnostic instruments, telemetry medical apparatuses, mobile wellness management devices, software medical device and other forms of health management devices.

(Hardware Architecture)

Figure 1:
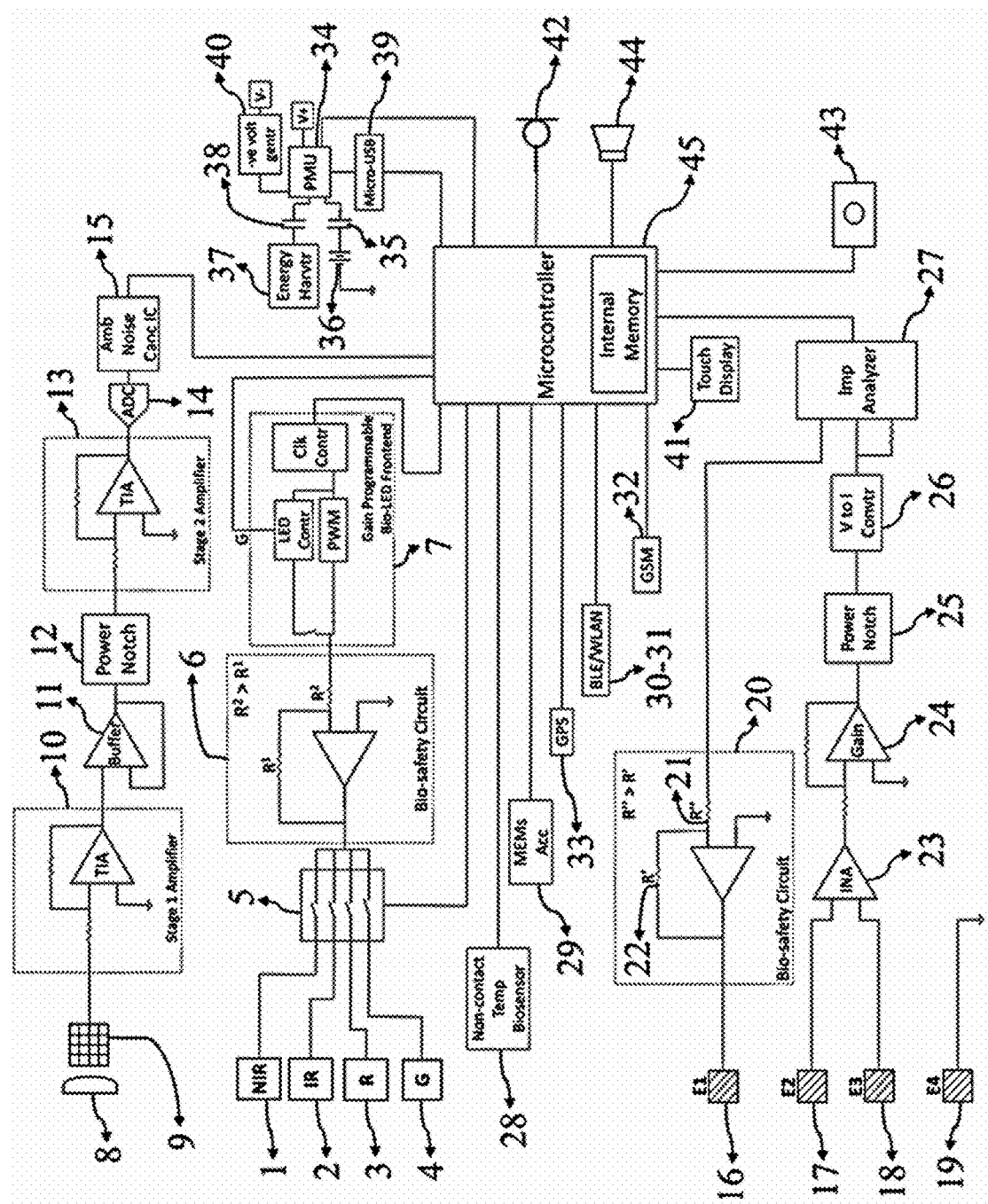
FIG. 1 is the block diagram and hardware architecture of the telemetry apparatus.

FIG. 1 is the hardware architecture of the telemetry apparatus. It comprises of optical elements, optical spectrometer, electrical spectrometer, biosensors, analogue circuitry, digital ICs, power supply unit, wireless antennae, computational device and other electronic components.

The hardware of the optical spectrometer has reduced input signal sent to LED signal probes, of Near-Infrared LED 1, Infrared LED 2, Red LED 3 and Green LED 4, through a biosafety frontend 6. A multiple switch set 5 is attached to the biosafety circuit and a gain programmable Bio-LED frontend 7, which is utilized as the means to reduce the power requirement and number of active components. The gain programmable LED frontend 7 triggers the input signal, where the gain can be adjusted based on the user input or programmed input. The set of multiple switches 5 automatically shifts the input signal to generate the multi-spectral signal as per the control commands.

An optical component 8 focuses and concentrates the optical response on the photodetector set 9. The photodetector set 9 records the optical response and the photoresponse excitation passes through a series of logic circuit of Stage 1 amplifier 10, Buffer 11, power notch 12, Stage 2 amplifier 13, ADC 14 and Ambient noise cancellation IC 15. The series of logic circuit comprising of 10, 11, 12, 13, 14 and 15 filters noise, amplifies and processes the output response. The response, in turn, is communicated to the microprocessor 45.

The electrical spectrometer comprises of set of electrical sensors 16-17-18-19, bio-safety circuit 20, a series response processing circuit, and Impedance Analyzer IC 27. The input signal is generated by the impedance Analyzer chip 27 and passes through a biosafety circuit 20. The bio safety circuit is made of an input impedance 21 greater than the feedback impedance 22, which is used as the means to improve the operational safety. The regulated input signal is injected through an input electrical sensor E1 16 and drains through the electrical sensor E4 19.

The electrical sensor E2 17 and electrical sensor E3 18, are placed between the input electrical sensor E1 16 and draining electrode E4 19, for extracting the response signals. The response is analysed, amplified and filtered through a response circuit line of Instrumental amplifier 23, Gain amplifier circuit 24, power notch filter 25 and V to I converter IC 26. The analysed and processed response passes through the Impedance Analyzer chip 27, which assess and resolves the output electrical response, and communicates the analyzed response to the microprocessor.

The sensor set of MEMs/NEMs non-contact temperature biosensor 28 and MEMs/NEMs 9/6-axis accelerometer 29 are attached to the microprocessor 45, which are utilized to record real-time feedback, body temperature and motion signals. A set of wireless antennae of the WLAN 30, BLE 31, GSM 32 and GPS 33 are either externally attached to the microprocessor or integrated inside the microprocessor 45. The set of wireless antennae 30-31-32-33 communicates the data between the telemetry apparatus, and the set of external storage and computing devices like accessorial mobile devices, server, etc. The set of wireless antennae 30-31-32-33, along with the accelerometer 29, is used for tracking the real-time location and movement signals like phase, speed, steps taken, etc. The wireless microprocessor 45 with inbuilt memory, is used for communicating commands and feedbacks with the internal electronic components of LED frontend, photodetector frontend, Impedance analyser IC 27, Accelerometer 29, temperature biosensor 28, other sensors, wireless antennas 30-31-32-33, USB module 39 and other electronics modules. The microprocessor 45 also computes and stores the required information.

The hardware of the telemetry apparatus is powered by a power supply unit, containing power management IC 34, supercapacitor 35-battery set 36, supercapacitor 38-renewable energy harvester 37, USB module 39 and negative voltage converter 40. The power management unit 34 is attached to the power supply unit, and microprocessor 45. The power management IC 34 regulates the current flow and power supply. The USB module 39 and supercapacitor 35-battery set 36 powers the electronic circuit. The micro-USB module 39 is also used to communicate the data with the external devices and charging the battery 36 of the internal circuit. The negative signal reference is generated by the negative voltage converter 40. The power supply unit has an alternative powering unit containing renewable energy harvester 37 and supercapacitor 38.

A touch display 41 is attached to the hardware for viewing and accessing the real-time medical information, health data and on-device applications. The touch display 41 is used to operate the instrumentation and embodiment forms of the telemetry apparatus. Apart from the display unit 41, the hardware of the telemetry device is internally or externally attached to an additional user interaction system of mic 42, video camera 43 and speaker 44. The set of user interaction hardware components is utilized for interacting with the professional medical and health practitioners for clinical and health analysis. The professionals can send and receive the information, as well supervise the user. The user interaction unit 42-43-44 is also used as the means to perceive the recorded and computed information, and to operate the telemetry device and its in-built applications.

(Reflective Optical Spectrometer)

Figure 2:
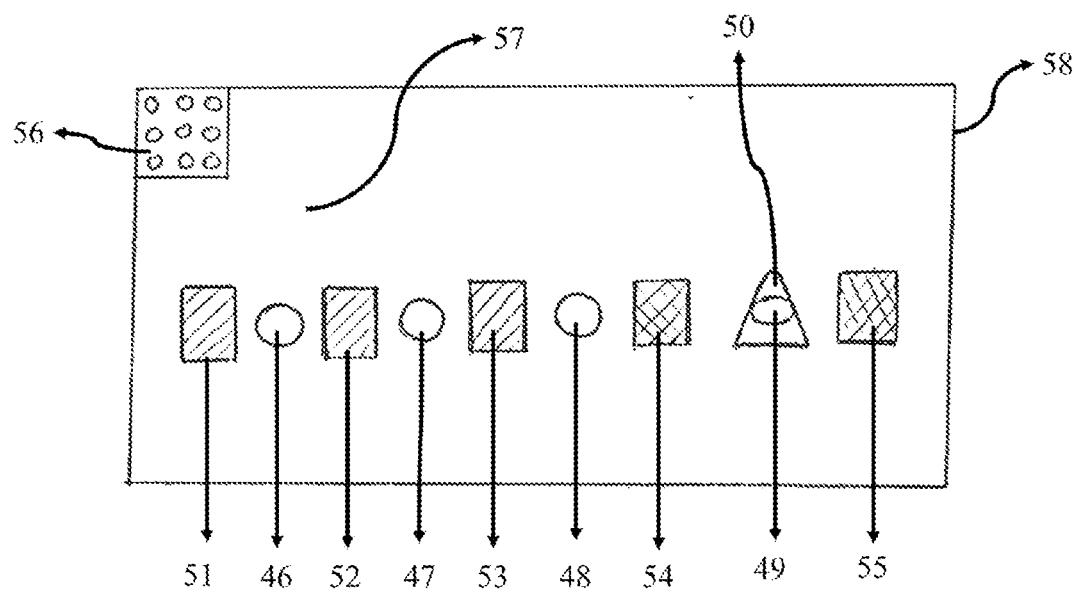
FIG. 2 shows the design of a reflective optical spectrometer with adjacent LED-photodiode configuration.

FIG. 2 is the reflective optical spectrometer with adjacent LED-photodiode arrangement, where each signal probe and respective response detectors are placed next to each other. The signal probes of Green LED 46, Red LED 47, IR LED 48 and Near-Infrared LED 49 are assembled at optimal distance between their corresponding photodetector set of visible, IR photodetector and Near-Infrared photodetector of 51-52-53-54-55. The Infrared LED's 49 radiation is tuned and focused through an optical system/micro-prism 50. The set of LED signal probes 46-47-48-49 inject the optical signals and the reflected the signal response is recorded by the set of adjacent Photodetector probes 51-52-53-54-55. The Non-contact NEMs/MEMs temperature bio-sensor 56 is placed at an optimal distance and away from the heat dissipation surface, and with its thermopile probes facing the contact surface. The temperature bio-sensor 56 is utilized for recording the error-free body temperature and thermal noise feedback. A disposable foam base 57 is placed on the contact surface of the optical spectrometer 58, around the sensors, signal probes and receiver area, which is used as a mechanical means for reducing the motion errors. The adjacent LED-photodetector configuration is utilized to quickly and simultaneously extract the optical response.

(Hardware Packaging of the Telemetry Apparatus with Reflective Spectrometer)

Figure 3:
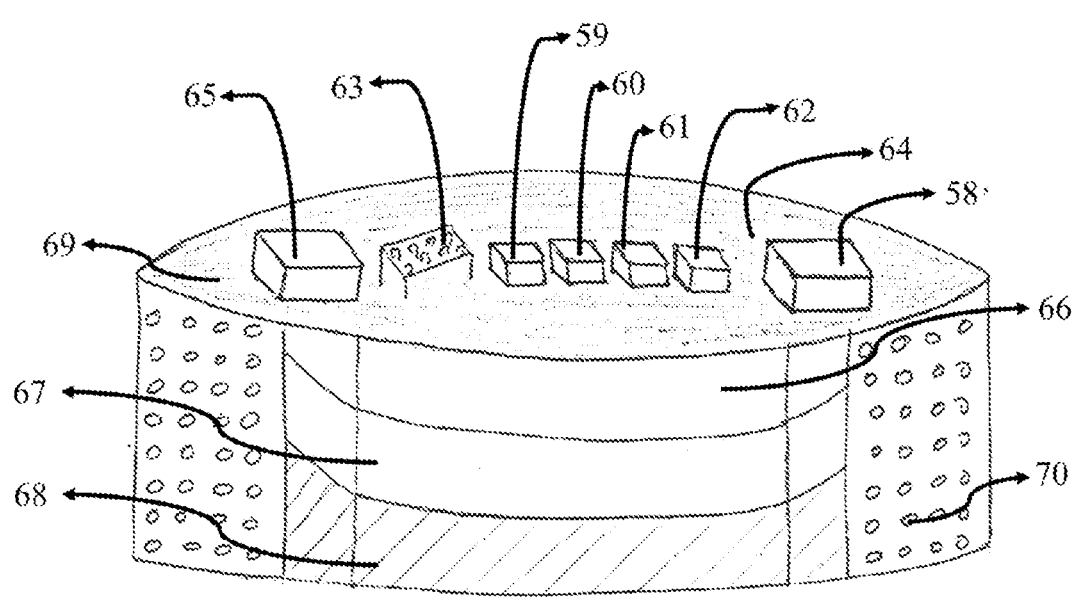
FIG. 3 is the isometric view of the hardware packaging of the reflective sensing apparatus.

FIG. 3 is the isometric view of the spectrometer packing. The biosensors set of optical spectrometer apparatus 58, non-contact MEMs/NEMs temperature sensor 63 and the set of electrical sensors 59-60-61-62 are assembled on the contact surface 64, for extracting the bio-signal response. The optical apparatus 58 is aligned in the blood flow direction for extracting optical response. The 9/6-axis MEMs/NEMs accelerometer 65 is arranged in a corresponding reference direction to the biosensor set, which is utilized as an efficient method to extract the feedback signals and motion signals. The electrical sensor of 59, 60, 61 and 62 are arranged in a straight line, and in a specific direction with reference to the accelerometer sensor 65. The electrical sensor 60 and electrical sensor 61 are placed in between the input electrical sensor 59 and drain electrical sensor 62, which is used for extracting the electrical response. The Analog and Digital frontend plane 66, containing the sensor's digital and analog frontend, is placed in a successive vertical plane to the biosensor plane. The third sequential electronic plane 67 containing microprocessor, power supply unit, computing unit, wireless antennas and other ICs embedded plane. The last layer 68 of the packaging accommodates the set of battery, energy generation unit and other power unit components. The last power plane 68 is packaged such that the battery and metal components does not obstruct the wireless antennas, which is used as method to curtail noise interruption. The casing of the package is perforated with ventilation pores 70 for regulating the heat of the device. The described packaging method is used as the means to reduce tracing efforts, curtail electrical noise and increase packaging efficiency. The foam base/disposable sponge 69 is placed on the contact surface 64 around the bio sensors, which is utilized for reducing the motion errors and increasing the multi-use utility.

(Spiral Ring Embodiment Form with Transmittive Optical Configuration)

Figure 4:
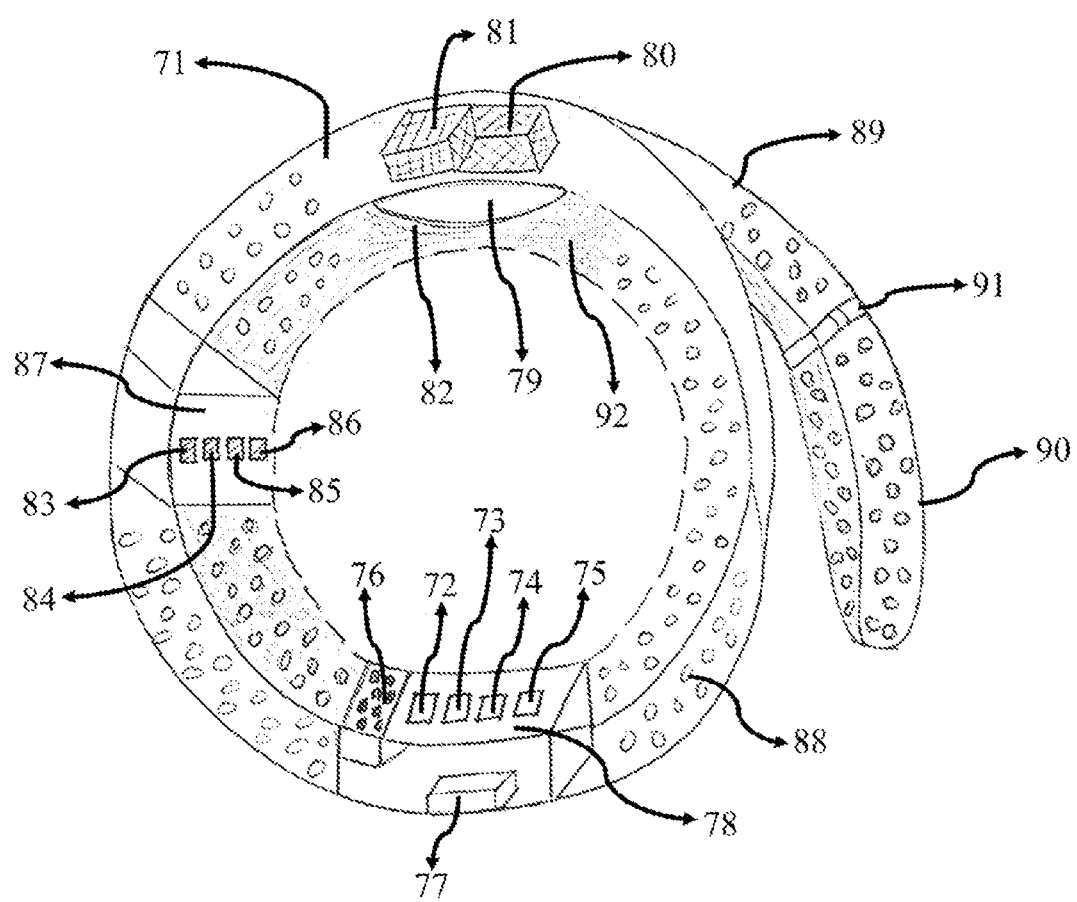
FIG. 4 is the transmittive optical configuration based spiral ring embodiment form of the telemetry apparatus.

FIG. 4 is the isometric view of the transmittive optical configuration based ring embodiment preferred in the clinical monitoring and general wellness management. The ring embodiment form is fabricated in a spiral ring structure with a main heat dissipating expandable ring body 71 and a spirally extending element 89. The ring 71-89 is made up of heat dissipating and expandable material. The main ring frame 71 contains sensors, wireless antennas, power supply unit, battery, digital chips, Analog ICs, microprocessor, integrated circuits and other essential electronic components. The optical signal probes of Near-Infrared LED 72, Infrared LED 73, Red LED 74 and Green LED 75 are placed in an inverted configuration with LED probes facing the underside of the contact surface 78. The NEMs/MEMs non-contact temperature biosensor 76 is assembled at edge of the ring frame and away from the heat dissipation surface, which is utilized for measuring body temperature values and thermal feedback. A 9/6-axis NEMs/MEMs accelerometer 77 is positioned in a specific reference direction to the biosensors for precisely recording the movement feedback and movement signals. The photodetector set of visible/IR 80 and Near-IR photodetectors 81 are aligned with the corresponding signal probes and placed on the top response receiving surface 82. An optical lens 79 is placed before the photodetector set 80-81 for efficiently capturing and focusing low powered optical response on photodetector set 80-81. The inverted configuration of LED signal probes 72-73-74-75 and photodetector set 80-81, minimizes the background optical noise in the recorded response. The set of electrical biosensors 83-84-85-86 are assembled in a straight line on the perpendicular contact surface 87, or in an aligned straight line on the contact surface, which is utilized for extracting electrical bio-signals. The regulated input signal is injected through the input electrical sensor 83 and drains through the electrical sensor 86. The electrical sensor 84 and electrical sensor 85, placed between the input electrical sensor 83 and draining electrode 86, are used for extracting the response signals.

The spirally protruding structure 89 contains an adjustable clipper 90 and hinge 91, that holds the instrument on the sensing spot in a size adaptable manner. The expandable material is additionally utilized to hold the device securely on the sensing spot. The ventilation pores 88 are embedded on the device casing. The heat dissipating casing material along with the ventilation pores 88 are used as the means to regulate the device heating. A foam base 92, implanted on the contact surface surrounding the biosensors, enhances the mechanical gripping of the device.

(Open Ring Embodiment Form of the Telemetry Apparatus)

Figure 5A:
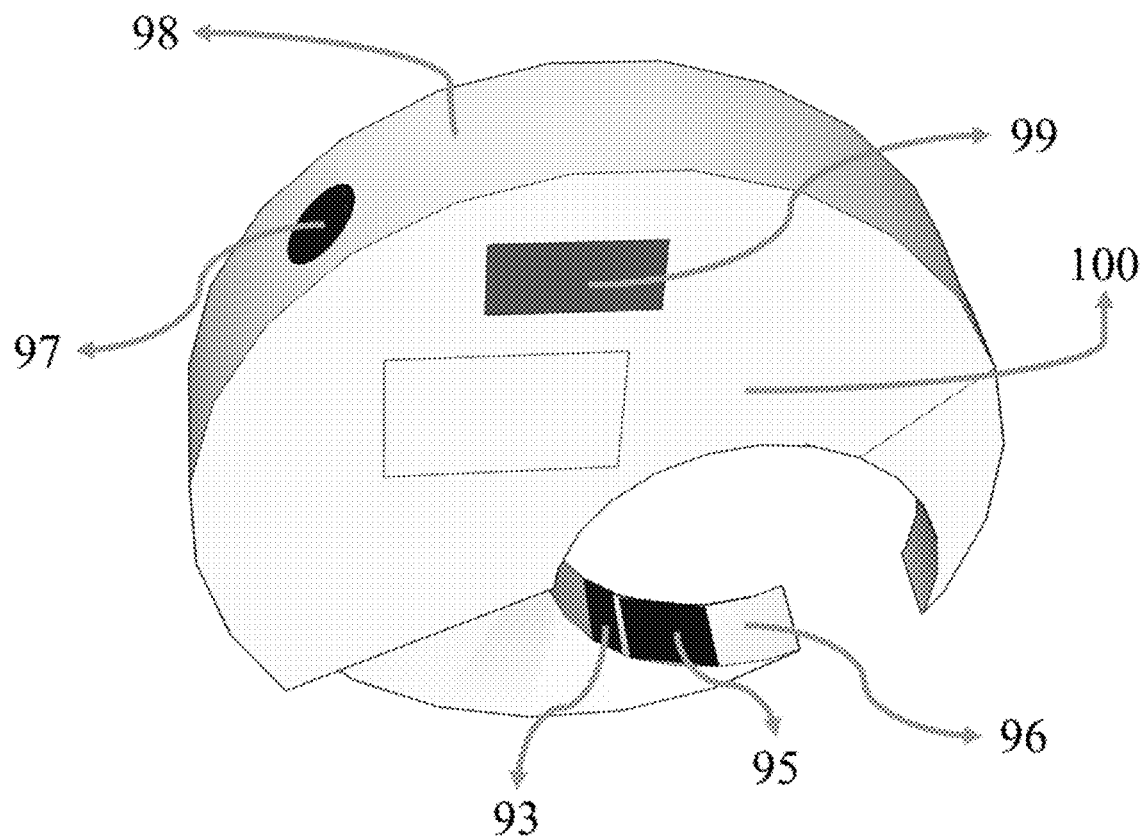
FIG. 5A and FIG. 5B show isometric view of a ring based wearable embodiment form for remote clinical monitoring and daily wellness management.
Figure 5B:
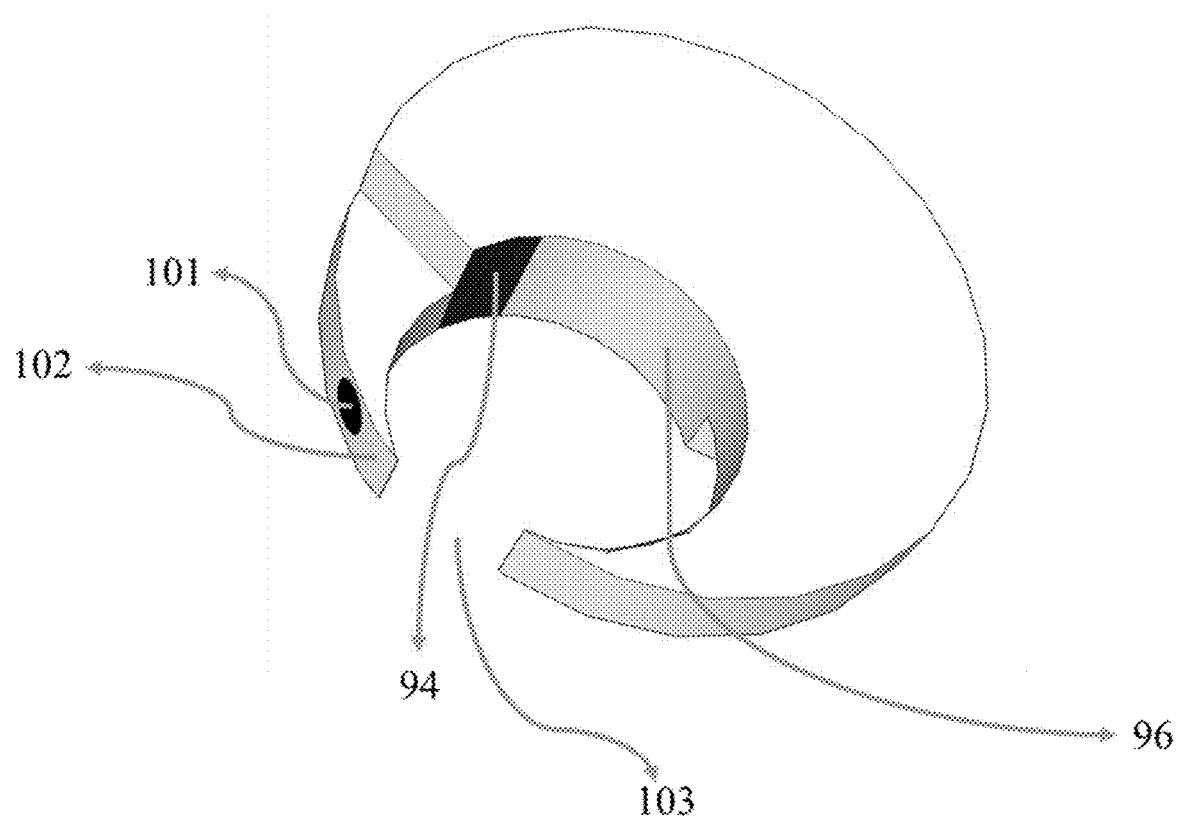

FIG. 5A and FIG. 5B show the telemetry embodiment form for general wellness management and telemetry monitoring. The sensors, detectors and signal probes are assembled at an optimal sensing point 93 and an optimal response spot 94 of the contact surface 96. A micro vibrator 95 is assembled on the contact surface 96 of the ring, which is utilized to guide the user during mental stress/anxiety and to prompt the scheduled alarms calls. The device has a vibrator 95 based persona-oriented stress management application, which automatically activates and guides the user during the instances of stress or anxiety. Once the state of stress or anxiety is recognized, the micro-vibrator module 95 on the contact surface oscillates in a definite remedial pattern to calm the user. During the real-time guided stress management application, the vibrator 95 oscillates with 7.5%-25% higher ON time to indicate breath-out demonstration and 7.5%-25% lower OFF time to indicate breath-in demonstration. The button 101 on lower edge surface 102 is used to switch the device mode to meeting mode, work mode, fitness mode and sleep mode. The button 97 on the top surface 98 is used for accessing the telephonic calls, wireless synchronization facilities and other functionalities. A gesture sensor 99 is embedded on the front surface 100 (user facing surface). The gesture sensor 99 is used for accessing and navigating through the presentations and applications. The button inputs 97-101 are also used to access presentations and applications. The open ring structure 103 of the ring apparatus holds the device on the sensing spot in a size adjustable manner.

(Telemetry Embodiment Form for Forehead or Limb Monitoring)

Figure 6:
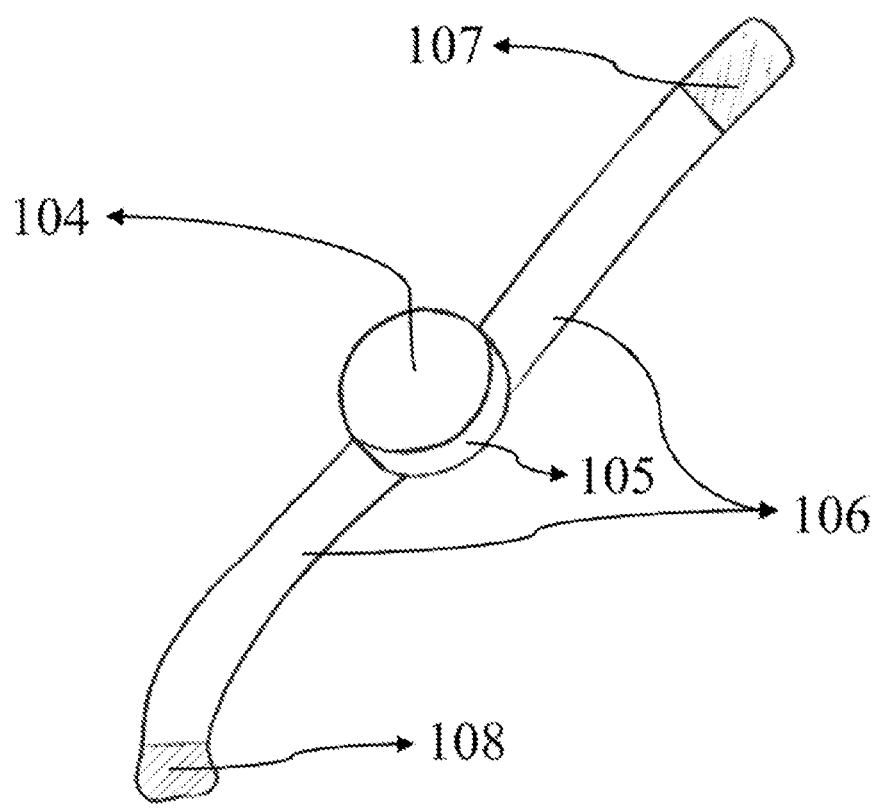
FIG. 6 illustrates the 3-D view of the clinical embodiment form for forehead and limb telemetry monitoring.

FIG. 6 is the 3D view of the embodiment form for clinical forehead monitoring or ambulatory limb telemetry monitoring. The Reflective bio-sensing apparatus with foam base 104 is embedded on the contact surface of the main casing 105, which is used for sensing the bio-signals. The main casing 105 is made of heat regulating material. The digital IC, analog chips, microprocessor, wireless antennae, sensors, power supply unit and rest of electronics items are packaged inside the heat regulating casing 105. A soft stretchable cloth 106 is attached to the main packaging case 105, which contains adhesive surface 107 and stickable surface 108 end tail pads. The adhesion action between the adhesive pad 107 and stickable pad 108 is used to fasten the device, and as well hold the sensing apparatus on the sensing spot. Additionally, the stretchable cloth belt 106 holds the apparatus steadily on the sensing spot. The foam base on the contact surface and surrounding the biosensors is utilized as a mechanical means to reduce movement noise in the bio-signal recording. The other use of the disposable foam includes improvement of the clinical hygiene and reusability efficiency.

(Auxiliary Training Machine Attachment Embodiment Form)

Figure 7:
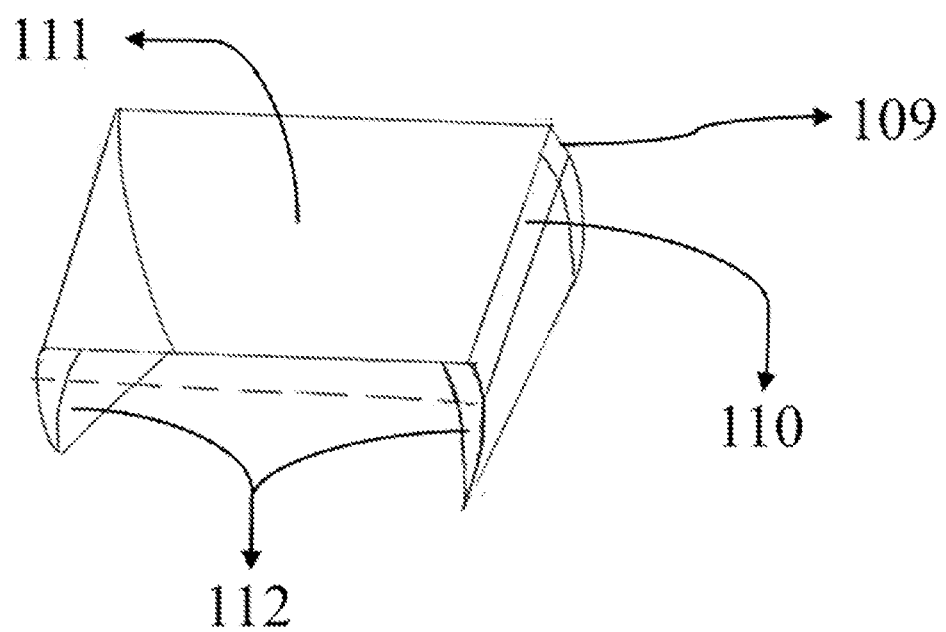
FIG. 7 is the auxiliary embodiment form utilized for monitoring health and clinical information during exercise on training machines.

FIG. 7 shows the embodiment form utilized as an auxiliary attachment to the wellness instrument. The auxiliary device 109 is utilized while training on exercise machines like cycle, treadmill or bike to record and monitor clinical/health signals. The instrument 109 with the heat regulating casing 110 is attached to the wellness exercising instrument through an expandable machine gripping holder 112. During the health management activity and medical monitoring, the expandable machine gripping holder 112 is used for fastening the instrument 109 on the auxiliary machine handles. The reflective sensing hardware and the set of biosensors with foam base 111 is placed on the contact surface of the main packaging frame 110, which is used for recording the relevant real-time clinical and health information. The digital chips, analog ICs, microprocessor, wireless antennae, sensors, microprocessor and essential electronics components of the apparatus 109 are packaged in the heat regulating case 110. The foam base on the contact surface around the bio sensors, is utilized to reduce movement noise in the bio-signal recording, and as well to improve the clinical hygiene and reusability efficiency.

(Multifunctional Clinical Instrument for Live and Telemetry Monitoring)

Figure 8:
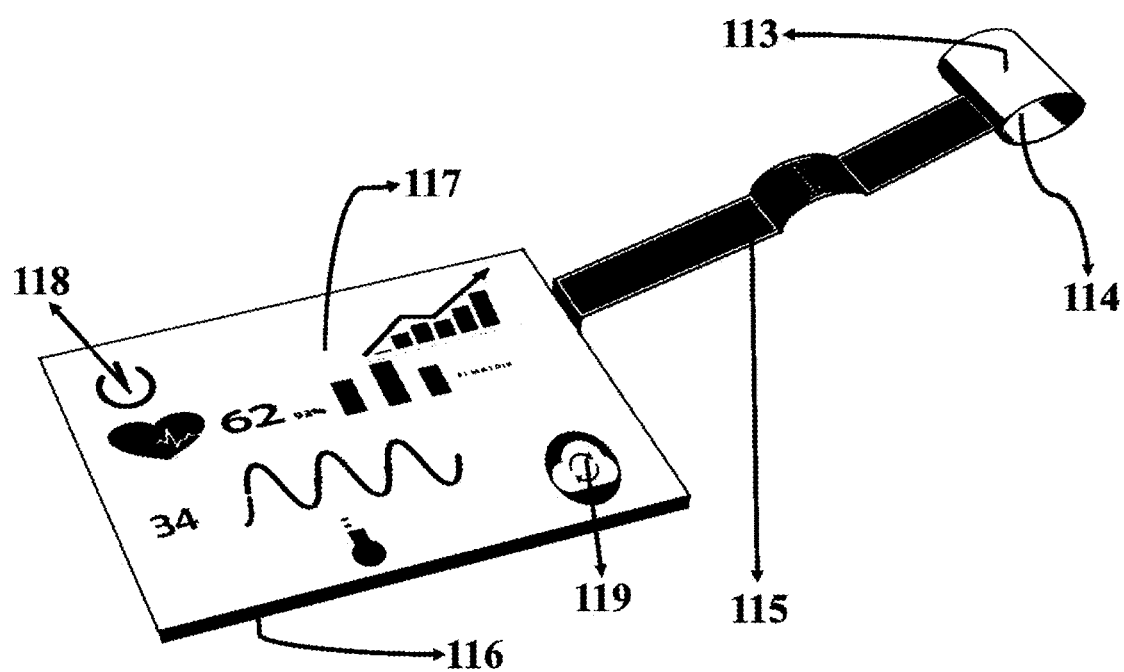
FIG. 8 is the 3D-view of the live clinical and telemetry monitoring instrumentation.

FIG. 8 is the live and telemetry clinical monitor, that can display real-time medical signals as well as personalized results. The live clinical monitor has a central wireless base station 116 and an inflatable mini-cuff 113 packaged with set of biosensors 114 (electrical spectrometer, optical spectrometer, non-contact MEMs/NEMs temperature sensor, accelerometer, etc). The digital ICs, analog chips, power supply unit, sensors, microprocessor, wireless antennae and other electronics are packaged inside the wireless base station 116. At the contact of the user, the mini-cuff 113 automatically inflates to detect the resonant point for blood pressure calibration. The bio-signals are extracted through the set of biosensors 114. A slate sized touch display 117 is assembled on the wireless base station 116, which is utilized for accessing and viewing important clinical information, patient history, patient's physical activities, health data and live medical signals (like breathing rate, heart rate, oxygen saturation, bio-temperature, blood pressure, blood sugar levels, neural activity balance, etc). The slate sized touch display 117 is also used at the means to operate the medical instrument and to access the in-built applications. The base station 116 along with the slate sized monitor 117 and buttons 118-119, is attached to the mini-cuff 113 both wirelessly or through an electrical cord 115. The button 118 on the base station 116 resets the medical analysis, powers on/off the device and executes other important functionalities. The patient history, medical information and other important information are synchronized, between mobile telemetry apparatus and computer server/accessorial mobile apparatus, through the button 119 on the base station 116.

(Smart Band Embodiment Form of the Telemetry Apparatus)

Figure 9A:
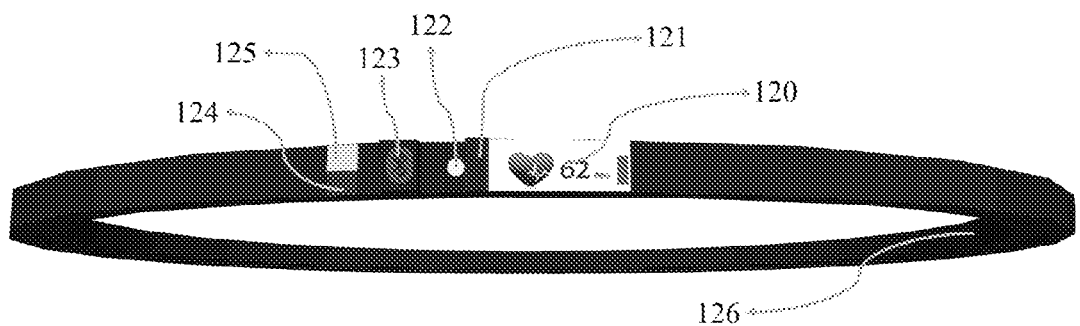
FIG. 9A and FIG. 9B show isometric view of wearable tracker embodiment form for real-time medical monitoring and general wellness management.
Figure 9B:
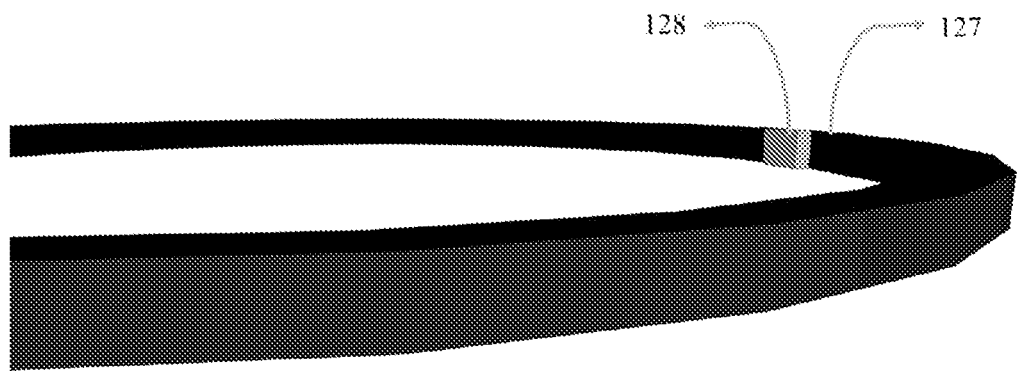

FIG. 9 is the preferred wearable embodiment form for remote clinical monitoring and daily well-being management. FIG. 9A shows the isometric front view of the smart band embodiment form. FIG. 9B shows the isometric back view of the smart band embodiment form with reflective hardware apparatus. The device comprises of mini touch display 120, trigger button 121, mode-indicator 122, wireless synchronization button 123, micro/mini-inflatable strap 126 and Stress Management blinking LED set 124-125. The mini-touch display 120, placed on the top surface of the apparatus, is utilized for operating the apparatus, accessing in-built application and viewing the essential information (such as medical information, health data, bio-signals, general wellness data, etc). A set of Red indicator LED 124 and Green indicator LED 125, attached on the top surface, are used as an apparatus guided method for stress management. The indicator LEDs of 124-125 automatically blinks to guide the user during the instances of psychological stress or anxiety. During the state of mental stress, the red indicator light 124 automatically flashes at the detected neural activity and the green indicator light 125 automatically flashes in a definite assisting pattern. For guiding the user through stress management, the green indicator light 125 blinks with a 7.5%-25% higher ON time to indicate breath-out demonstration, and 7.5%-25% lower OFF time to indicate breath-in demonstration. The strap-based micro/mini-inflatable cuff 126 automatically inflates to detect the resonant compression point for blood pressure calibration. The mode indicator light 122 shows different operating modes and other functional status of the apparatus. The trigger button 121 is utilized for operating the device, accessing in-built applications and utilizing other functionalities. The apparatus has a wireless button 123 for synchronizing the data and telemetry device with the accessorial devices. The biosensor set and reflective sensing apparatus 128 (of optical apparatus, electrical, non-contact temperature sensor and accelerometer) is assembled on the contact surface of the device. The digital ICs, analog chips, power supply unit, sensors, microprocessor, wireless antennae and other electronics are packaged in the casing 127.

(Smart Wearable Embodiment Form of the Telemetry Apparatus)

Figure 10A:
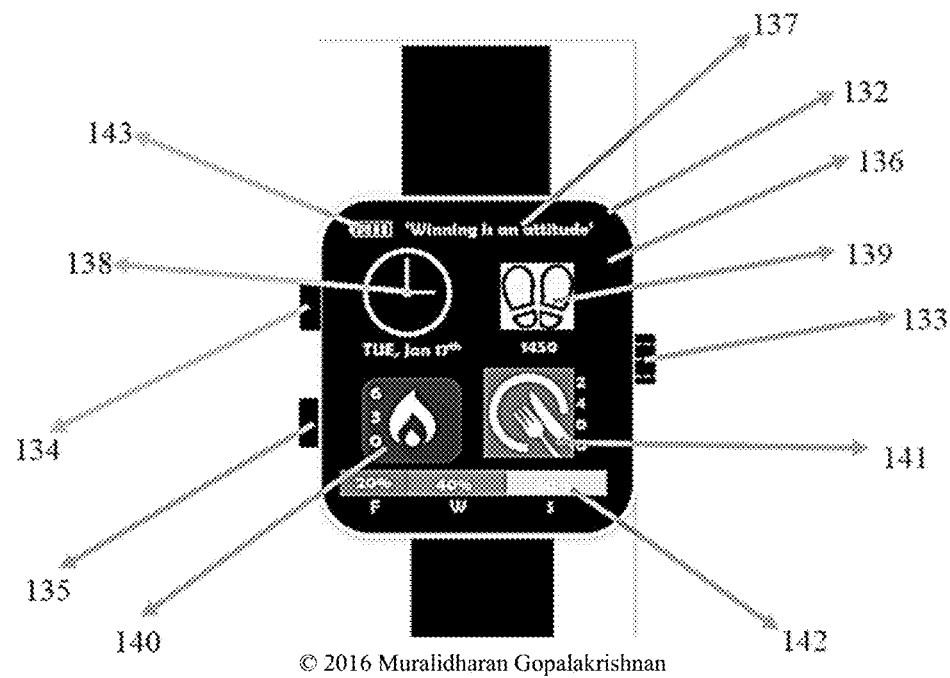
FIG. 10A and FIG. 10B show the smart wearable embodiment form of the telemetry apparatus with rounded corners.

FIG. 10A shows the start-up application and rounded corner smart mobile apparatus design for general wellness management and telemetry medical monitoring. The mobile apparatus 132 has a potentiometer integrated crown 133 and push buttons 134-135, which are utilized as the means to operate the apparatus 132 and access in-built applications. The real-time diagnostic signals, health management data, medical data and other important information are viewed on the mini-touch screen 136. The mini touch display 136 is also used as the means to operate the device 132, and device applications. A background application containing motivational quote 137 is displayed on the top of the apparatus 132, which is intended to improve the spirit of the user. The diagram also shows a start-up application comprising information on Time & Date 138, Step Count 139, Calorie burnt 140, Calorie consumed 141, weekly health history 142, battery strength 143, climate information 144, wireless connectivity 145 and other trends.

Figure 10B:
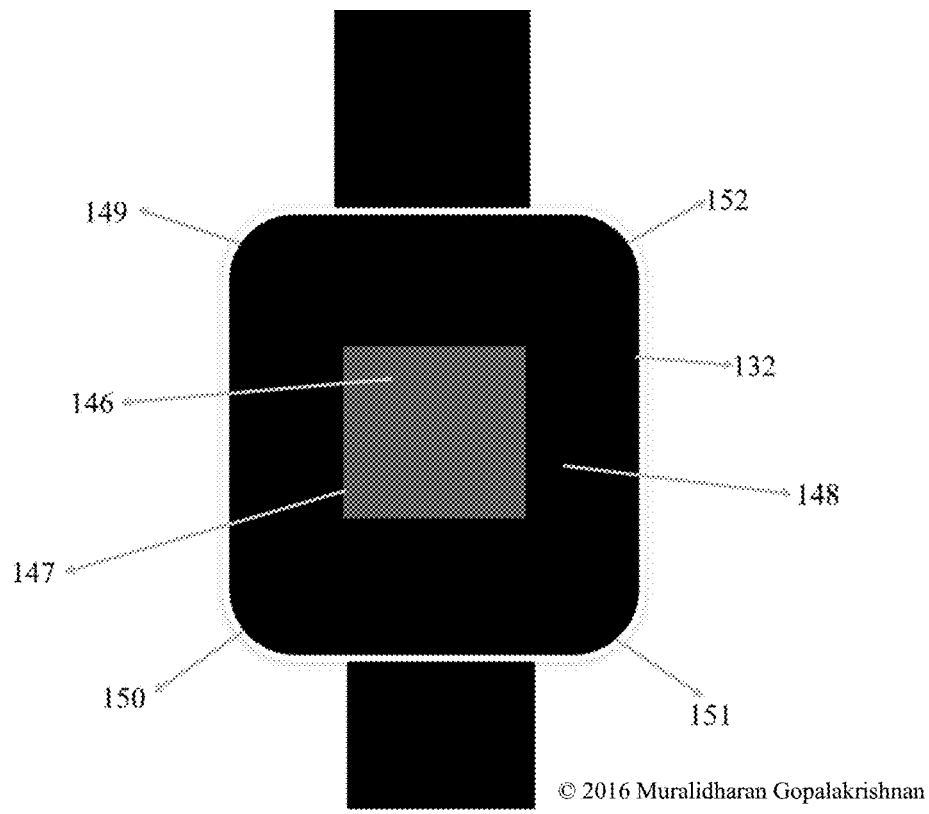

FIG. 10B shows the placement of the reflective sensing apparatus on the mobile apparatus with rounded corner design. The reflective sensing apparatus 146 is assembled in an optimal sensing spot 147 on the contact surface 148 of the apparatus 132. The rounded corners 149-150-151-152 of the apparatus 132 are chosen as a means to evade cuts and injuries, that may occur due to the otherwise sharp corners.

Figure 11A:
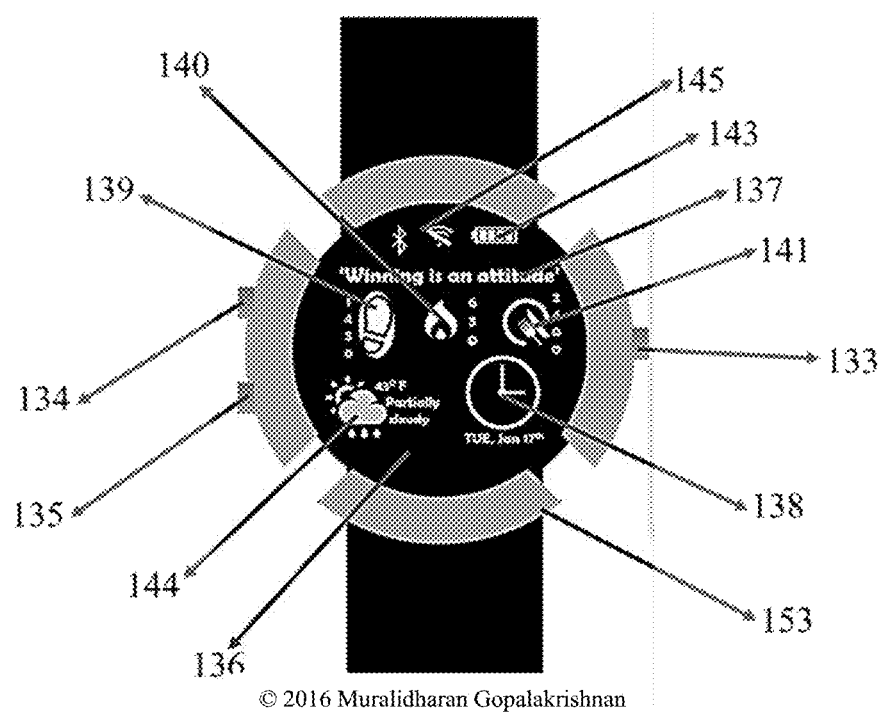
FIG. 11A and FIG. 11B show the round face smart wearable embodiment form of the telemetry apparatus.

FIG. 11A shows the start-up application and round face smart mobile apparatus design for general wellness management and telemetry medical monitoring. The mobile apparatus 153 has a potentiometer integrated crown 133 and push buttons 134-135, which are utilized as the means to operate the apparatus 153 and access in-built applications. The real-time diagnostic signals, health management data, medical data and other important information are viewed on the mini-touch screen 136. The mini touch display 136 is also used as the means to operate the device 153, and device applications. A background application containing motivational quote 137 is displayed on the top of the apparatus 153, which is intended to improve the spirit of the user. The diagram also shows a start-up application comprising information on Time & Date 138, Step Count 139, Calorie burnt 140, Calorie consumed 141, weekly health history 142, battery strength 143, climate information 144, wireless connectivity 145 and other trends.

Figure 11B:
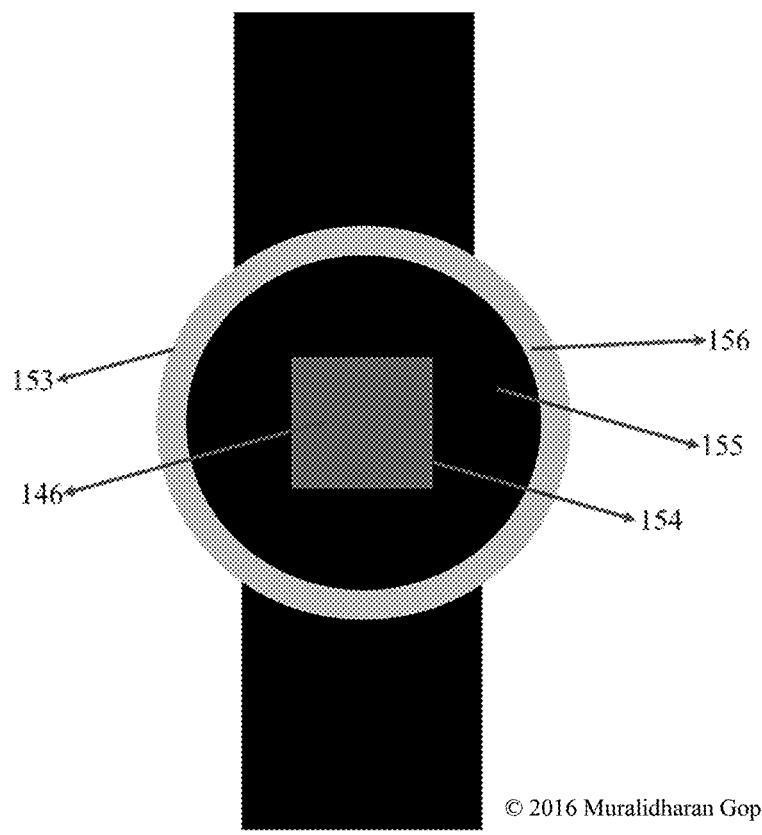

FIG. 11B shows the placement of the reflective sensing apparatus on the mobile apparatus with round face design. The reflective sensing apparatus 146 is assembled in an optimal sensing spot 154 on the contact surface 155 of the apparatus 153. A round face and bezel 156 of the apparatus is chosen as a means to evade cuts and injuries, that may occur due to the otherwise sharp corners.

Series of FIG. 12 shows the embedded health management and clinical monitoring applications of the smart wearable embodiment.

Figure 12A:
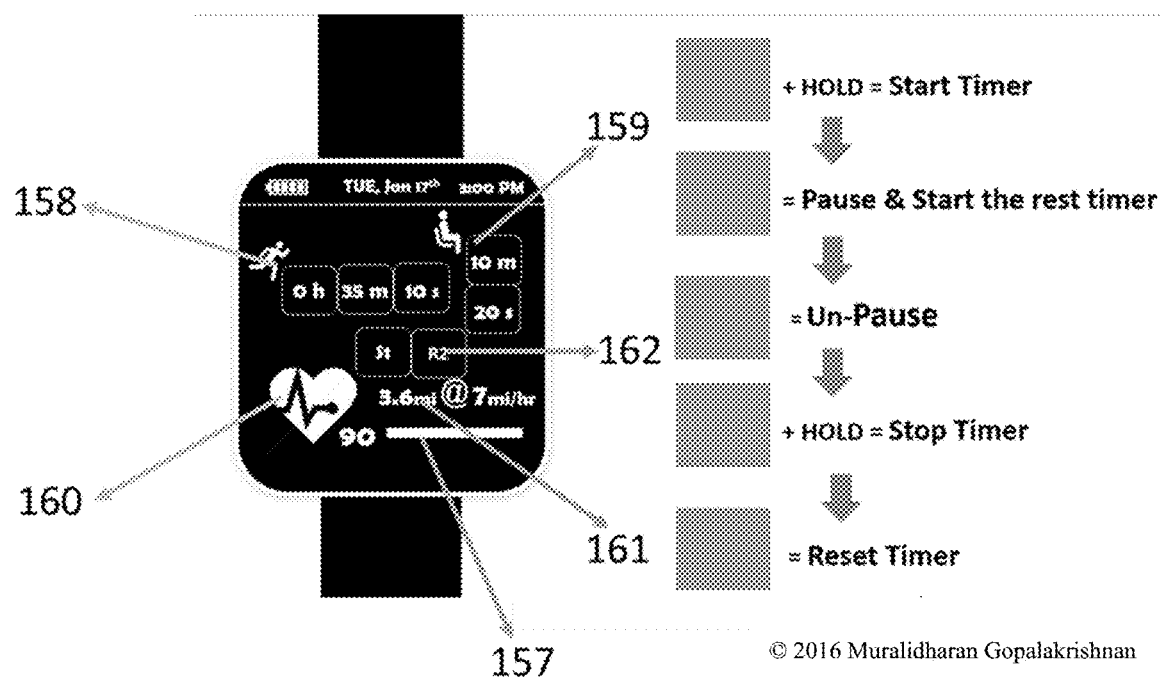
FIG. 12A illustrates an automated cardiac training software application of the wearable embodiment form.

FIG. 12A is the cardiac training software application of the smart wearable apparatus. During physical training, the cardiac training application automatically tracks both quantitative and qualitative data such as training intensity 157, training period 158, rest period 159, cardiac rate 160, training phase 161 (such as distance travelled, average speed count), sets and reps counts 162 and other important health data.

The training session begins on the long hold of the trigger push buttons 134-135, and the real-time training data is recorded. The tracked data is displayed on the mini screen 136. On a subsequent short press of 134-135, the tracking switches between rest and intensity period, and a long hold of the push button 134-135, the tracking period halts. The apparatus either ends the activity tracking on a successive small hold of the push button 134-135 or resumes the tracking on a successive long hold of the push button 134-135. The mini-touch display 136 is used as an alternative means to operate the commands of the application.

Figure 12B:
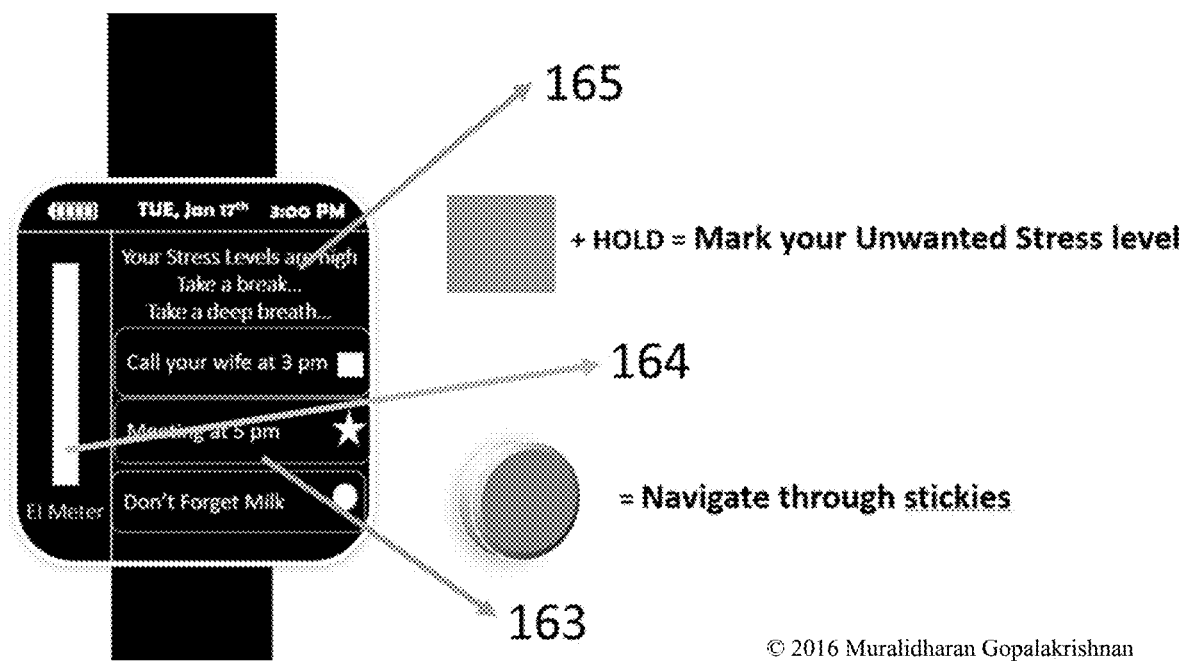
FIG. 12B is a persona oriented psychological stress management application of the wearable embodiment form.

FIG. 12B shows a persona oriented psychological stress management application. The mobile apparatus's mini screen 136 displays queued work schedule with priority rating 163, real-time stress levels (Emotional Index meter) 164, and information on stress levels and stress management 165. The user initially marks several reference data points to train the smart apparatus for learning the persona-oriented stress levels. The real-time stress levels are generated through previously marked subjective data points. The reference data points are generated based on the analysis of biosensor and other vital information. Based on the reference points and real-time signals, the apparatus generates subjective psychological stress data 164. On recognizing the state of stress or anxiety, the application automatically guides the user to a stress management method. The push buttons 134-135, crown 133 and mini-touch display 136 are utilized as the means to mark the stress data points, to navigate through the work schedule and to operate the functionalities of the application.

Figure 12C:
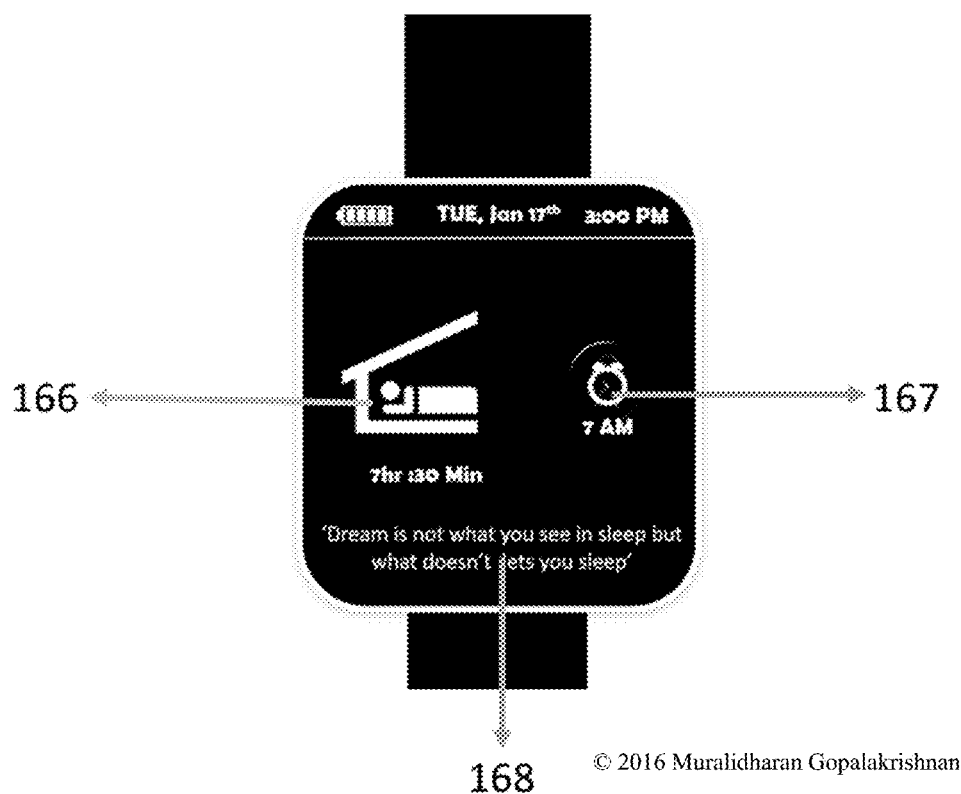
FIG. 12C is the sleep management software application of the smart wearable embodiment form.

FIG. 12C shows the sleep management application of the smart wearable apparatus. The real-time sleep information 166 is automatically recorded and displayed on the screen 136, along with an accessorial user configured alarm control 167. A morning motivational quote 168 is displayed on the screen 136 to keep the user inspired. The push buttons 134-135, crown 133 and mini-touch display 136 are used as the means to set the alarm, access the logged data, view the recorded data and as well to operate the functionalities of the sleep management application.

Figure 12D:
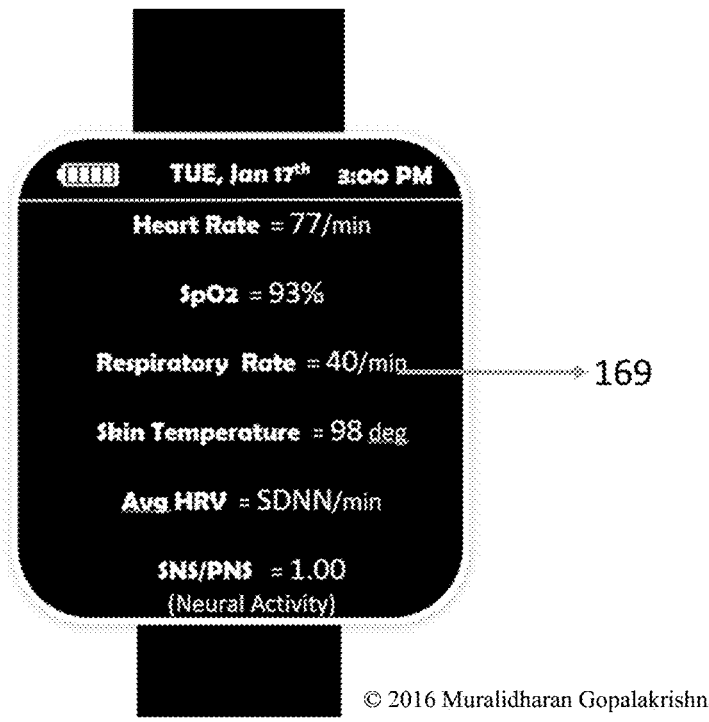
FIG. 12D shows the application design to view live and stored medical information.

FIG. 12D shows the mobile application of the smart wearable apparatus to view live medical information and access logged data. The recorded and real-time vital information 169 of pulse rate, oxygen saturation ratio, breathing rate, body temperature, heart rate variably, blood sugar data, blood pressure data and Neural Activity are displayed on the mini-screen 136. The push buttons 134-135, crown 133 and mini-touch display 136 are utilized as the means to access the logged data and operate the functionalities of the live monitoring application.

(Network of Computational and Storage Devices)

Figure 13:
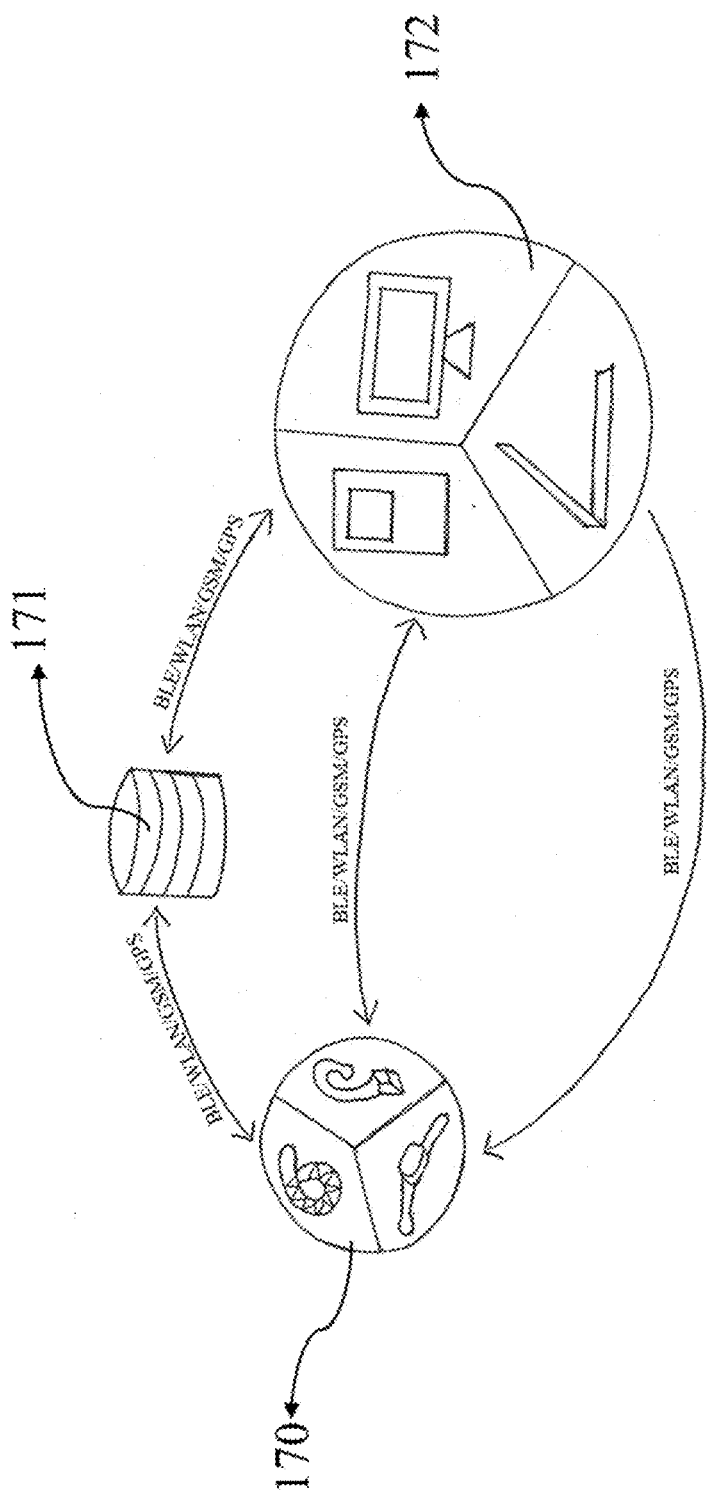
FIG. 13 illustrates the network of devices technology to compute and extract information more speedily and efficiently.

FIG. 13 shows wireless devices network based parallel computation method to compute and extract information more quickly. The Telemetry device 170 sends and receives data to/from the server computer 171 and the other accessorial devices 172 via BLE/WLAN, GSM and other techniques. The accessorial mobile apparatus 172, server computer 171 and other network of devices are utilized for computing and storing the information. The network of devices based computational and storage method is used as a faster and efficient means to compute and store information. The communication channel between the 170 and 172 is established via central server 171 or directly through the wireless pathways.

(Application of the Telemetry Apparatus)

Figure 14:
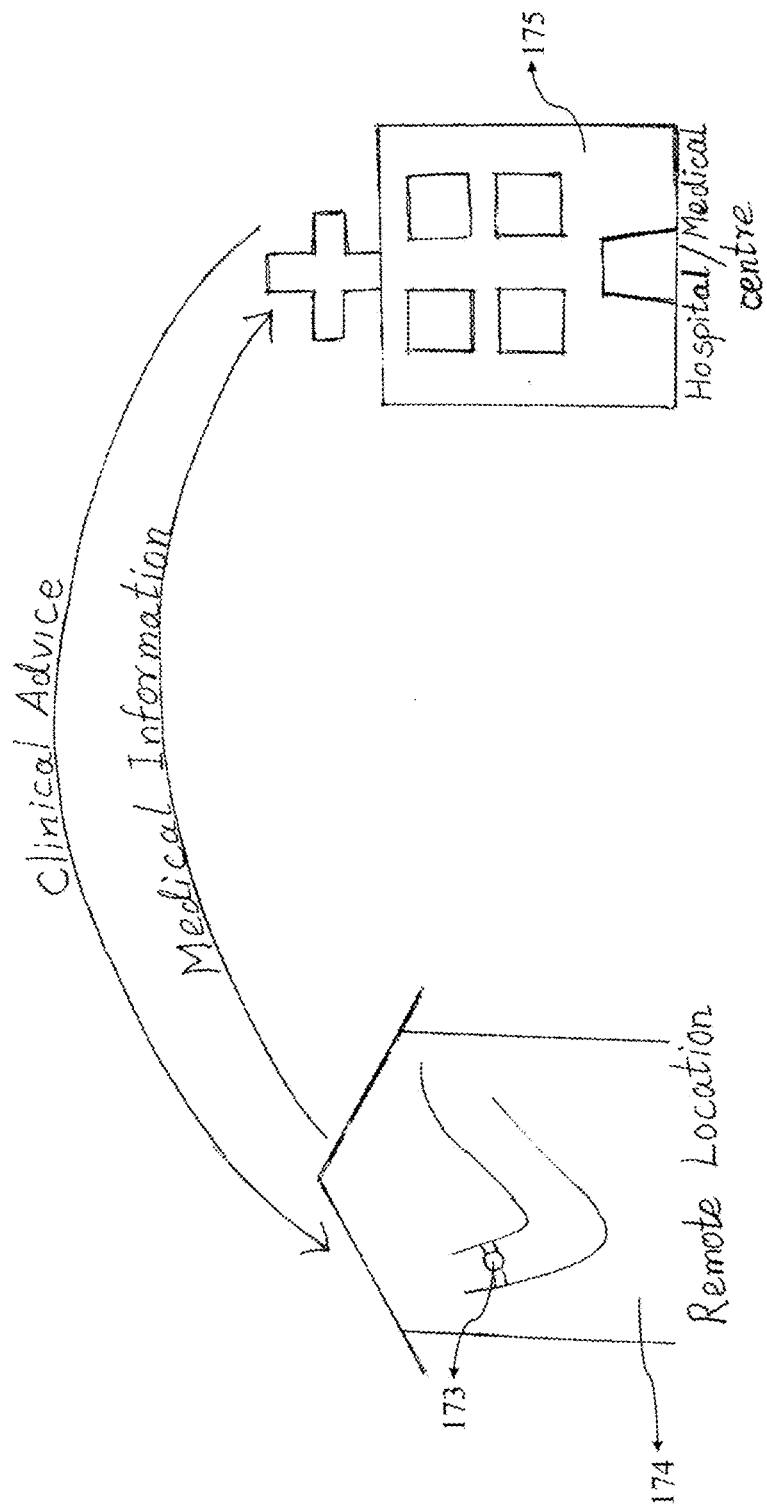
FIG. 14 illustrates the application of this telemetry device for remote clinical monitoring purposes.

FIG. 14 shows the application of the telemetry device for remote clinical monitoring purposes. The recorded real-time information, clinical information, health-data and user input information are wirelessly sent to the hospitals 175 from the wireless medical device 173 in a remote location 174. The clinical advice, medical instruction and other information are sent wirelessly from the Medical Centre/Hospitals 175 to the Telemetry device 173 located in Remote Location 174.

Figure 15:
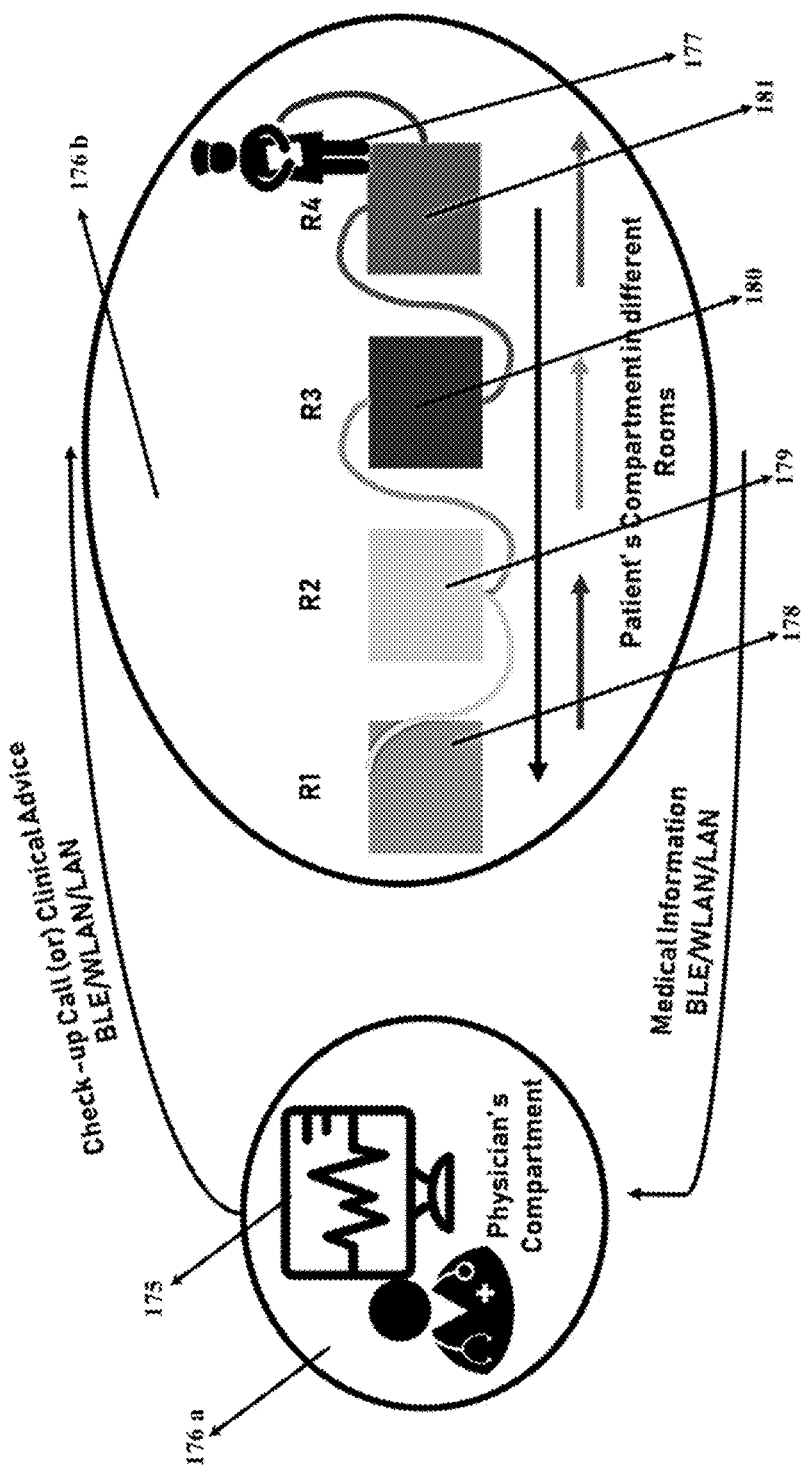
FIG. 15 shows the application of this telemetry device for live clinical monitoring in a crowded hospital scenario.

FIG. 15 shows the application of the telemetry devices in a crowded hospital scenario. The medical practitioners 177 can attach medical devices of 173 to the patients in the rooms R1 178, R2 179, R3 180, R4 181 and in many such rooms in the patient's clinical compartment 176b. The recorded real-time information, clinical information, health-data and user input information are wirelessly sent from the wireless medical devices of 173 in rooms of 178, 179, 180, 181 and in many such rooms to the physician's room 176a with telemetry monitor and base station 175. The real-time medical information, patient's history, patient's information, diagnosed clinical condition and recorded medical analysis are viewed on the wireless telemetry monitor of the base station 175. The clinical advice, medical instruction, drug dosage recommendation and other important information are sent wirelessly from the Physician's compartment 176a or personally conveyed to the patient. The information can be communicated wirelessly between the medical practitioners 177, patients in 178, 179, 180, 181 and many such rooms and physician's room 176a in lesser time and more efficiently compared to the typical clinical and hospital set-up. This scenario shows that clinical analysis of patients in multiple rooms of 178, 179, 180, 181 and many such rooms in the patient's compartment 176b can be conducted and analyzed in lesser time with lesser efforts and with more efficacy.

(Real-Time System)

FIG. 16A is the signal processing flow diagram which describes the utilization of accelerometer signals as a real time feedback to remove the motion errors from the bio-signal. Accelerometer signals are recorded along with other bio-sensor data with their respective sampling rate. The sampled bio-signal is initially passed through a 50/60 Hz Notch filter to remove the power line noise disruption. The bio-sensor data and angle calibrated accelerometer data is processed with a normalized parameter based repetitive adaptive filter and other computational method to remove low frequency motion noise from the bio-signal.

A first order noise free bio-signals are obtained after the correlation of the angle calibrated accelerometer data with bio-sensor data with a delay through a normalized parameter based least mean squaring based adaptive filtering. The first order noise free bio-signals obtained, after removal of the movement error (A"(n)) i.e. the motion noise, is processed through later mentioned flow diagrams to further remove motion noise or movement errors associated with the bio-sensor data.

FIG. 16B is the flow diagram to process accelerometer values to compute the movement activity of the user or patient. Normalized magnitude for amplitude of the recorded accelerometer signals is computed and then the base line errors are removed. Then, a data based computational method and peak detection algorithm is applied to the processed data to calculate the active movement data.

As described in FIG. 16B, the data based computation method, of a deviation from a mean of the normalized magnitude dataset (i.e. processed data of the 9/6-axis accelerometer), is applied and a peaks, from within the deviation dataset of the normalized magnitude dataset, are detected to obtain the active movement data (i.e. step movements and also number of steps).

FIG. 17 is the flow diagram to process the first order motion artefact free bio-signal to precisely compute avg. pulse rate, instantaneous heart rate, pulse rate variability and neural activity coefficients. The first order signal is passed through a series of banked and low pass filter to remove the rest of the noise in the bio-signals. Then, a data correlation method is applied between the processed bio-sensor data and accelerometer data to further remove the motion artefact noise from the original signal. A peak detection algorithm is applied to the $3^{rd}$ Order processed motion artefact free signal to compute average. pulse rate and instantaneous heart rate. The recorded heart rate time intervals are plotted to display the pulse rate variability and HR Tachogram. A variance-based data method is applied to the derived pulse rate and variability data for computing the autonomous neural activity coefficients of $\sigma 1$, $\sigma 2$, $\sigma 3$, $\sigma 3/\sigma 1$, $\sigma 3/\sigma 2$, $\sigma 2/\sigma 1$.

As described in the flow diagram of FIG. 17, after sending the first order signals (or first order noise free bio-signals) through a series of banked filters with dynamic parameter (M), a second order noise free bio-signals are obtained. A correlation factor (Corr) is extracted by correlating the second order noise free bio-signals with a delay and the angle calibrated accelerometer signals, which is analyzed to obtain a movement error free bio-signal responses. Then, a data correlation method of, the accelerometer data operation on the second order noise free bio-signals is applied to obtain noise data (M'(n)) and the noise data is removed to extract energy undistorted values of a third order noise free bio-signals. The autonomous neural activity coefficients of $\sigma 1$ is extracted by computing a root of a mean of a differences between an adjacent values of the time intervals of the time intervals dataset. The autonomous neural activity coefficients of $\sigma 2$ is extracted by computing a mean of the time intervals of the time intervals dataset. The autonomous neural activity coefficients of $\sigma 3$ is extracted by computing a root of a mean of a deviation of the time intervals of the time intervals dataset from the $\sigma 2$.

FIG. 18 shows the low powered computational method to extract continuous heart Rate, avg. pulse rate and oxygen saturation levels. The $3^{rd}$ Order signal is sampled at chosen sampling rate and recorded in 32/64/128 . . . data points. A discrete wave transformation is applied to the processed signal and a selection matrix is operated on the resulting frequency domain signal. The operation of selection matrix significantly decreases computational effort needed to analyse the entire waveform, and an iterative peak detection algorithm is applied to the processed signal to determine maxima's frequency and thereof continuous heart rate and average heart rate are extracted. The signal ratio between the oscillating peak and stationary peak of red and Infrared biosensor is taken to determine the oxygen saturation ratio.

The mean of the determined oxygen saturation ratio (i.e. continuous oxygen saturation) from the third order noise free bio-signals is extracted to obtain an average oxygen saturation (Avg. SpO2).

FIG. 19 shows band-pass digital filters and power spectrum analysis methods to process Inverted tachogram data (i.e. frequency domain signal of Instantaneous heart rate). The reconstructed frequency domain signal is divided into High-Frequency, Low-Frequency, Very Low Frequency, Meyer band and Ultra-low frequency signals using the high pass, bandpass and low pass digital filters of corresponding bandwidths. Then, the relative power under each frequency spectrum is calculated to assess neural activity. The derived coefficient of $P_1$, $P_2$, $P_3$, $P_4$, etc are evaluated through a set of computational steps to determine the overall health of Autonomous Neural System and cardiac system.

The autonomous neural activity parameters of P1, P2, P4 and P5 are respectively obtained by extracting the power spectrum under the low frequency, the high frequency, the very low frequency and the ultra low frequency band signals. A ratio of P1 to P2 is taken to obtain P3.

FIG. 20 shows the flow diagram and analysis method to compute and display respiratory signal, continuous respiratory rate, meyer wave signal and average breathing rate. The noise-free pulse bio-signals are analyzed for extremum to decouple the noise artefact free signals into different wave signals. An iterative wave decoupling algorithm is applied to the pulse signal to obtain the low frequency breathing signal. The derived signal is processed for peaks and experimental parameter to determine the respiratory rate. The analysed signal is mathematically operated for computing average breathing rate, continuous respiratory rate and breathing rate. A similar analysis is applied to decompose the meyer wave signal and its related neural parameters. This method of computational wave decoupling is low powered, and the accessorial mobile/server computational devices are utilized to improve the response time of the medical apparatus.

As described in FIG. 20, the decoupled waves obtained after the iterative analysis with the extremum (of interpolated maxima and minima of the local maxima and the local minima), is evaluated for a breathing signals frequency range to obtain the breathing signals (I'RR(t)).

FIG. 21 is the flow diagram and computational technique to measure blood pressure data from previously calibrated user data. The user calibration input, optical data and extremum of the samples with respect to time are recorded. The user input and recorded optical data are employed to calibrate the biosensor reading. In all device configurations, the method of optical intensity ratio between the extremum is utilized to calibrate the blood pressure values of continuous blood pressure and diastolic pressure. The dual sensor configuration is utilized to estimate momentum loss in the blood vessel, mean pressure and the systolic pressure. The recorded heart to device reference length is used in the cuff-based apparatus to accurately measure the mean arterial pressure.

As described in the flow diagram of FIG. 21, a mean of a corresponding ratios of the minima dataset to the maxima dataset of the extremum dataset (recorded with respect to time) is correlated with measured diastolic blood pressure values in real-time and a measurement coefficient (Z) to extract the real-time diastolic blood pressure (i.e. the utilized method of optical intensity ratio between the extremum). In the dual sensor configuration (i.e. optical spectrometer A and optical spectrometer B) to estimate momentum loss in the blood vessel, mean pressure and the systolic pressure, a time intervals datasets for a corresponding bio-signal response between the extremum datasets of optical spectrometer A and optical spectrometer B is recorded. Then, a ratio of a mean of the time intervals to the distance (d) between the dual sensor (i.e. optical spectrometer A and optical spectrometer B) is taken to obtain a Mean Longitudinal Pulse Velocity (Long. $V_{pulse}$). The mean longitudinal pulse velocity and the real-time diastolic blood pressure are correlated to extract the real-time mean arterial blood pressure and the real-time systolic blood pressure. A ratio ($\kappa$) between the measured and calibrated values is used to improve the accuracy of the real-time blood pressure values. Alternatively, recorded heart to device reference length is used in the cuff-based apparatus to accurately measure the mean arterial pressure that is obtained by correlating the cuff pressure and the blood density at the resonant point i.e. Pcuff+$\mu g h_r$. In this case, a standard value of blood density ($\rho$) or user input on the same is taken for computations in cuff based apparatus. The heart to device reference length (hr) can also be obtained automatically by analysing the real-time signals from the 9/6-axis accelerometer in different arm positions of user (which is described in the next flow diagram and their relevant description).

FIG. 22 shows the flow diagram to automatically calibrate the heart to device reference length, that is employed to compute blood pressure. The value of 9-axis accelerometer sensor signals are recorded at different arm positions of bent arm position, fully stretched arm position, lifted arm position and straight down arm position. Using the recorded sensor data, the forearm and arm length are calculated, through which average heart to device reference length is generated.

FIG. 23 shows the flow diagram and method to process the near-infrared bio-sensor signals and other optical signals to compute blood sugar levels. Initially the input on the present blood sugar level is taken for sensor calibration. The Green LED, IR LED and Red LED response signals are used to compensate the intensity losses due to the blood flow fluctuations, tissue absorption and other coherent errors. The Processed Near-Infrared data is correlated and fitted over various patient's/user's/physician's inputs to calibrate the biosensors for approximate real time Blood Sugar values. Physiological threshold values of hyperglycemia and hypoglycemia are analyzed from the calibrated data. The system automatically reminds the patient for medication and alerts the user/user network or the physician about the diagnosed health condition.

FIG. 24 shows the flowchart and computational process to record various stages of the sleep cycle and to recognize obstructive sleep apnea Conditions. The accelerometer values are initially verified to make sure that user is in sleeping or dormant position. Then the real time physiological signals of (oxygen saturation ratio, body temperature, blood glucose levels, blood pressure, etc) are compared to state of wake, sleep and activity data to verify the state of sleep and rest. After the verification process, the real time physiological signals of avg. breathing rate, avg. systolic blood pressure and instantaneous heart rate signals are processed to track the time periods of non-rapid eye movement and rapid eye movement sleep cycles. Then a series of methodical computational steps are applied on the instantaneous heart rate, sleep cycle and respiratory rate data to recognize sleep apnea conditions and to calculate the time-period of sleep apnea. The pulse rate data in a time interval of 30-60 s and for 5-7 BPM difference is analyzed to recognize sleep apnea conditions. The respiratory signals are validated for sleep apnea conditions after pulse rate and instantaneous pulse rate data analysis. The recognized sleep health conditions and time period are recorded. Once the mild to severe symptoms of OSA are recognized by the apparatus, a warning message is sent to the patient and her/his physician network.

In the series of methodical computational steps applied on the instantaneous heart rate, sleep cycle and respiratory rate data to recognize sleep apnoea conditions and to calculate the time-period of sleep apnoea, the instantaneous heart rate dataset is analyzed in one or more time frames, for a specified range of beats per minute difference between their extremum, and for a falling edge and a raising edge in a cycle time. As mentioned before, the specified range of beats per minute (BPM) is in range of the 5-7 BPM, the cycle time is at 9.5 seconds and the time frames (i.e. time intervals) are kept at 30-60 seconds followed by time frames of 20-120 seconds. The time periods of sleep apnoea are recorded on recognition of the sleep apnoea conditions ($T_{Apnea}=t_0-t_n$). As mentioned before, a pattern of an average respiratory rate dataset (i.e. respiratory signals) to further verify or validate the sleep apnoea conditions. A low and irregular pattern of the average respiratory rate dataset is used for verifying the sleep apnea conditions. Also initially during the sleep recognition processing, the vital information of average heart rate, average respiratory rate, blood pressure levels, oxygen saturation, blood sugar levels and body temperature are analyzed for a realistic range while analysing the real-time signals of the 9/6-axis accelerometer to verify that the Sleep Tracker is ON and the user is a sleeping and dormant state. The median values of $\Delta x$, $\Delta y$, $\Delta z$ obtained from accelerometer values over a period of time are evaluated against the heart to device reference length ($h_r$) or null values to verify the sleeping and dormant state.

FIG. 25 illustrates the basic low powered flow diagram that is utilized in multifunctional medical device, telemetry apparatus and general wellness management applications. Initially, the values of the vital signals like pulse rate, continuous heart rate, pulse rate, avg. heart rate, oxygen saturation ratio, neural activity, breathing rate, blood pressure data and blood sugar levels are extracted using the previously described computational methods. The realistic value of biological signals are verified to check if the worn by the user. The device automatically restarts on recognizing realistic value, else it remains in or goes to the sleep and shut-down mode. The device also automatically alerts user's life-support network and social on detecting clinical emergency risks.

FIG. 26A, FIG. 26B and FIG. 26C shows an automated life-support method for recognizing user activity, pre-clinical emergency conditions and for recording one's state of well-being. Initially, the sensor values are processed and calibrated. The sensor data, accelerometer values, GPS antenna, wireless antenna and bio-signals are evaluated for recognizing various postures and movement data (of sitting, standing, number of steps, number of strides, lap count, speed, training phase, resistance training, cycling, driving, etc). The recorded physiological information and motion sensor data are further processed and learnt by the device for precisely evaluating the postures, fatigue condition, rest period and activity period of the user. The postures, activity state, training data and other computed information are learnt and recorded. The circadian errors are removed from the derived data and the health of circadian cycle is evaluated using a learning method. The electrical signals and optical signals are correlated and corrected to rectify the errors in the bio-signal data. Then, the system computes BMR data and calorie expenditure from the computed vital signals and physical activity. A learning method of the system automatically derives the low-powered bio-signal processing methods and life-support process. The system detects the state of mental stress or anxiety utilizing the EEG patterns, recognized cortisol level, respiratory patterns and HRV patterns. If the user triggers for new stress threshold, the device records new stress mark-ups. Based on the bio-signal data and stress mark-ups, the system derives subjective stress levels. On recognizing the state of mental stress, a guided breathing stress management technique is presented to the user that functions on the individual's real time vital signals or the user is diverted to a stress management support network and social media. The clinical life-support component of the system automatically recognizes the risk of CHF attacks, hypoxia, hypothermia, hypoxemia, blood poising, blood loss, hyperthermia, unusual ventricular activity, heat stroke, nervous breakdown and other chronic conditions from oxygen saturation data, pulse rate, breathing data, neural parameters and HRV data pattern. If a life threating or chronic clinical condition is recognized, the apparatus automatically alerts the user's network and life support network.

Elaboration of the description of the processing as written in flow diagrams of FIG. 26A, FIG. 26B and FIG. 26C is provided in this paragraph. The device i.e. apparatus is sent to start or wake up mode after detecting a realistic range of bio-signals from the biosensor set. For first few times, a plurality of inputs from the user on clinical and health data for biosensor calibration and learning parameters calibration are recorded. If already sufficient inputs on inputs from the user on clinical and health data is recorded, the recordings of inputs is skipped. The vital data (i.e. plurality of vital signal data) of the heart rate, the respiratory rate, the blood pressure levels, the blood sugar levels, the oxygen saturation, the neural activity parameters and the body temperature are computed and stored. The vital signal data and the real-time signals of the 9/6-axis accelerometer are calibrated to detect a plurality of user positions and movement data comprising a sleeping state, a sitting position, a standing position, a running state, a sprinting state and a resistance training state. If already calibration is accomplished, a plurality of user positions and movement data is recognized. The step movements are analyzed to infer user positions, user postures, user state and user activity. At null step movement (i.e. step=0); a pattern of the heart rate, the respiratory rate and the blood pressure levels (i.e. vital signal data) is analyzed to detect whether user is in the sleeping state, the sitting position or the standing position. At null step movement (i.e. step=0); Avg. speed (average speed) is evaluated with a human physical limit to detect a cycling or a driving mode. The vital signal data is further analyzed to infer the cycling mode or the driving mode. At step movements (step >0), the average speed and the vital signal data are analyzed to detect a walking, a running or sprinting state. The plurality of user activity, posture and the movement data is verified by applying an unsupervised learning on the heart rate pattern. The stored values of the GPS and the real-time signals of the accelerometer is analyzed to detect a number of laps, the value of laps, a number of strides or steps per minute and a minutes per laps count (minute/lap count). The state of fatigue is detected based on vital signal pattern and real part of the impedance response. The vital signal pattern of the heart rate, the respiratory rate and the real part of the impedance response is analyzed to record and display a threshold index on the EI meter. On recognizing a stress state, the apparatus automatically guides the user to a guided breathing technique with an increased breath-out and decreased breath-in pattern, a meditation video and a social chat or call. If mark-up is triggered, a new threshold index is stored. The real-time blood sugar levels are analyzed to detect a hypoglycaemia state and a hyperglycaemia state. A pattern of the heart rate, the respiratory rate, the SNS/PNS, the neural parameters and the impedance response are analyzed to detect a Congestive Heart Failure condition. A decreasing pattern of the oxygen saturation, an increasing pattern of the heart rate and the respiratory rate (i.e. fast breathing) is analyzed to detect a CO poising condition. A low levels of the oxygen saturation, a fast unsteady pattern of the respiratory rate and an increasing pattern of the heart rate is analyzed for detecting a hypoxia condition, a hypoxemia condition or a blood disease condition. A reducing pattern of the body temperature and the heart rate is analyzed for detecting a hypothermia condition. An increasing pattern of the body temperature, the heart rate and the respiratory rate (i.e. increasing unsteady breathing) is analyzed to detect a hyperthermia condition. A threshold of the SNS/PNS and the real part of the impedance response is analyzed to detect an anxiety and a seizure state. A basal metabolic rate (BMR) value is derived and stored from heart rate data. Calories burnt is computed/obtained based on BMR value, distance commuted and intensity of physical exercise. The BMR generated from the most accurate heart rate result is used for analysis. The imaginary impedance from the electrical spectrometer is used as a feedback for the optical spectrometer to compute/obtain more accurate vital signal data. A data correlation is applied between the processing steps and computations of the optical spectrometer and the electrical spectrometer to detect low powered methods for computations and processing. An unsupervised learning is applied to remove errors due to circadian cycle and to analyse the health of circadian cycle health. The apparatus automatically sends a warning message to the user eco-system, the emergency contacts of the user and the user on recognizing health and emergency conditions.

(Accessorial Mobile Device and Software Application)

Series of FIG. 27 are the software applications of the accessorial mobile apparatus attached to the telemetry apparatus.

FIG. 27A shows the accessorial software, which displays important logged and processed information on user's or patient's heath. The user can log and track their personal information 182, routine health check-up data 183 (like weight, height, Basal Metabolic Index, Basal Metabolic Rate, workout target), physical exercise activities 184, and nutrition intake 185. The mobile apparatus shows real time and recorded health data 186 of the user or patient that includes base heart rate, distance commuted and calories expenditure. This information can help the user, patient or health advisor to measure the intensity of the physical exercise and progress of the therapy or fitness program. The cloud synchronization button 187 is utilized to synchronize the data with the cloud services and to share the data with professionals.

FIG. 27B shows the software application interface for the stress management in professional environment. It can be also employed by patients suffering from hypertension. The emotional index meter 189 is shown on the left, which shows persona-oriented measurement. The emotional index meter 189 oscillates according to the neural balance and other calibrated bio-signal. As the stress meter 189 reaches the threshold, the device directs the user to real time bio-signal based guided breathing/meditation method 188 or to a social communication interface. The progress on the stress management program is reported in tracking meter 190 shown at the center bottom of the diagram. The daily work management feature 191 is displayed on the right half, which shows the scheduled activity and their priority recorded by the user. The work management functionality is included, since procrastination is considered as an indirect counterpart cause of mental stress.

FIG. 27C shows the accessorial software to track and monitor sleep. As described earlier in the computational flow diagram section, the sleep cycle and other related data are computed using the biosensor signals. The recorded sleep cycle trend 192 and NREM-REM cycle length 193 are displayed, with access to sleep data log 194. In case of sleep disorder related clinical conditions, a warning message regarding the disorder symptom appears on the user screen. The user can connect with physicians and health professionals by clicking on the 195.

FIG. 27D shows the accessorial mobile device interface to monitor vital signals 196 of pulse rate, oxygen saturation, pulse rate variability, neutral activity, breathing rate, body temperature, blood glucose levels and blood pressure levels. The biosensor data is either processed by the mobile apparatus, central server or other accessorial wireless computational device. The computed real-time and recorded results 196 are displayed on the screen along with navigation access to view the individual physiological signal wave form. The medication tracker/remainder 197 (on centre bottom of the screen) and physician's network 198 (right bottom of the screen) are included to enhance the clinical management experience of the patient. The user can connect with medical and health professional by clicking on the button 198. The medication tracker and reminder 197 records the medication pattern and medication reminder. The device automatically alerts the user at the correct time to take medication. The data can be shared on online platforms and with medical and health professionals by clicking on 199.

FIG. 27E shows the accessorial software interface to connect with health advisor network. This application interface enables professional medical practitioners 200, dieticians 201, fitness instructors 202 and other health advisors to interact with the user, and to guide them with health practices/therapies. The health blogs, articles and classes can be accessed by the user through clicking on the icon 203.

FIG. 27F shows the user application interface for daily health management. It displays information on the number of active steps taken 204, sleep health 205, heart rate with oxygen saturation ratio 206, and emotional index matrix 207. The EI matrix 207 is the real-time information and recorded patterns of the emotional status and stress condition of the user. The background information on daily well-being can be accessed by the user by clicking on the left bottom button 208 (which can be evaluated to improve one's state of general health). The progress and history of the user can be accessed by clicking on the history trend button 210. The work schedule is organized by clicking on the center bottom work schedule button 209.

FIG. 27G shows the ease of lifestyle organization application interface, which displays the functionalities to synchronize, install and manage $3^{rd}$ party and native applications on the telemetry mobile apparatus.

The above described invention disclosure is intended for illustration purposes, and for those skilled in the art may instantly perceive numerous modifications, variations and equivalents. Therefore, the disclosure is not exhaustive in broader aspects and the invention is not intended to limit to specific details, illustrated hardware designs, described computational methods and embodiment forms. All equivalents and modifications are intended to be included within the scope of disclosure and attached claims. Accordingly, additional changes and modifications may be made without departing from the scope or spirit of the invention disclosure appended in the document, claims and their equivalents.

INDUSTRIAL APPLICABILITY

The described technological invention can be utilized as telemetry clinical instrumentations, general wellness management devices, real-time diagnostic technology, portable medical apparatuses, well-being management gadgets, smart wearable devices, server based real-time clinical diagnosis and health tracking system, life-support devices, health tracking software device and software medical device.

PRIOR ART AND CITATION LIST

CN 204467155 U (Kiwi Field (Hong Kong) Co. Ltd) 19 Jan. 2011

US 006122536 A (Animas Corporation) 19 Sep. 2000

US 006819950 B2 (Alexander K. Mills) 16 Nov. 2004

US 20120041276 A1 (Delcina Doreus and Evon Doreus) 16 Feb. 2012

WO 2015167251 A1 (HUINO CORPORATION) 5 Nov. 2015

Shubhangi Shripati Kadam and Sameer S. Nagtilak. "Non-Invasive Blood Glucose, Blood Pressure, Heart Rate and Body Temperature Monitoring Device", INDIA, IJRITCC, April 2017, Vol 5, Issue 4, ISSN 2321-8169, Pg. 69-72

Hereto the following are claimed:

1. A medical and health monitoring apparatus comprising:
    a microprocessor with internal memory;
    an optical spectrometer comprising:
        at least one or more of a green LED, a red LED, an infrared LED or a near infrared LED configured to inject a plurality of optical bio-signals;
        a photodetector set configured to record a plurality of optical bio-signal responses of the green LED, the red LED, the infrared LED and the near infrared LED;
        an optical component configured to concentrate and focus the plurality of optical bio-signal responses on the photodetector set;

a gain programmable bio-LED frontend configured to generate a plurality of gain adjustable input signals to the green LED, the red LED, the infrared and the near infrared LED based on a user input or a programmed input;

a switch set configured to shift input signals from the gain programmable bio-LED frontend to the green LED, the red LED, the infrared and the near infrared LED as per a control command;

a biosafety circuit configured to control input signals to the green LED, the red LED, the infrared LED and near infrared LED within operational safety levels to inject low powered optical bio-signals;

a series of processing circuits comprising a stage 1 amplifier, a buffer, a power notch, a stage 2 amplifier, an ADC and an ambient noise cancellation IC configured to filter noises in, amplify, stabilize and process the plurality of optical bio-signal responses from the photodetector set;

an electrical spectrometer comprising:
at least a first electrical sensor and a fourth electrical sensor configured to inject and drain an electrical bio-signal;
at least a second and a third electrical sensor, placed between the first electrical sensor and the fourth electrical sensor, configured to extract an electrical bio-signal response;
a biosafety circuit configured to control input of the electrical bio-signals within operational safety levels;
a response circuit line comprising an instrumental amplifier, a gain amplifier circuit, a power notch and a V to I converter configured to process, amplify, convert and filter the electrical bio-signal responses extracted from the second electrical sensor and the third electrical sensor;
an impedance analyzer IC configured to:
generate an input signal to inject the electrical bio-signal;
assess and resolve the electrical bio-signal response from the response circuit line;

a temperature biosensor, placed at a distance away from a heat dissipation surface, configured to record an error-free body temperature and a thermal feedback;

a 9/6-axis accelerometer, aligned in a reference direction, configured to provide a real-time feedback signals to remove movement errors from the plurality of optical bio-signal responses and the electrical bio-signal responses;

a wireless antennae set comprising a bluetooth connection, a wireless local area network connection (WLAN) and a global position system (GPS) configured to wirelessly communicate the plurality of optical bio-signal responses, the electrical bio-signal responses, the body temperature and a real-time signals from the 9/6-axis accelerometer to a network of computational and storage devices; and a power supply unit comprising a power management unit, a supercapacitor and a renewable energy harvester and a battery configured to regulate, store and supply power.

2. The medical and health monitoring apparatus in claim 1, wherein the biosafety circuit configured to control input signals in the optical spectrometer and the electrical spectrometer is an operational amplifier with an input impedance greater than a feedback impedance.

3. The medical and health monitoring apparatus of claim 1, wherein:
the green LED, the red LED, the infrared LED or the near infrared LED and the photodetector set are arranged in a blood flow direction; and
the first electrical sensor, the second electrical sensor, the third electrical sensor and the fourth electrical sensor electrical sensor are placed in a straight line and at equidistant positions along the blood flow direction.

4. The medical and health monitoring apparatus in claim 1, wherein the power supply unit of the medical and health monitoring apparatus further comprises:
a negative voltage converter configured to generate a negative reference voltage; and
an additional supercapacitor attached to the battery configured to store and supply power.

5. The medical and health monitoring apparatus in claim 1 further comprises a mobile communication module configured to wirelessly communicate the plurality of optical bio-signal responses, the electrical bio-signal responses, the body temperature and the real-time signals from the 9/6-axis accelerometer to the network of computational and storage devices.

6. The medical and health monitoring apparatus in claim 1, further comprising a plurality of user interaction components, comprising:
a touch display, a mic, a video camera and a speaker configured:
to provide an access to a plurality of health and medical information;
to provide an access for interaction with a health advisors network for a clinical and health analysis; and
to operate the medical and health monitoring apparatus.

7. The medical and health monitoring apparatus of claim 1, wherein the medical and health monitoring apparatus is configured to obtain:
a first order noise free bio-signals:
by applying a delay in real-time to the plurality of optical bio-signal responses and the electrical bio-signal responses, and by storing a real-time stable bio-sensing samples of the plurality of optical bio-signal responses and the electrical bio-signal responses;
by additionally passing the real-time stable bio-sensing samples through a digital notch filter to remove power line noise;
by parallelly calibrating the real-time signals of the 9/6-axis accelerometer to obtain an angle calibrated accelerometer signals while storing the real-time stable bio-sensing samples;
by a correlation of the angle calibrated accelerometer signals with the real-time stable bio-sensing samples to remove movement errors from the plurality of optical bio-signal responses and the electrical bio-signal responses;
a second order noise free bio-signals:
by analysing the first order noise free bio-signals, or the plurality of optical bio-signal responses and the electrical bio-signal responses, through a series of banked filters with a dynamic parameter;
a correlation factor:
by correlating the second order noise free bio-signals, or the plurality of optical bio-signal responses and the electrical bio-signal responses, with a delay and the angle calibrated accelerometer signals or the real-time signals of the 9/6-axis accelerometer;

a third order noise free bio-signals:
   by deducing an undistorted energy values of the plurality of optical bio-signal responses and the electrical bio-signal responses through correlation of a matrices of the second order noise free bio-signals and the real-time signals of the 9/6-axis accelerometer;
a time intervals dataset:
   by analysing an amplitude dataset of the first, the second or the third order noise free bio-signals for peaks and by storing a time interval between the peaks of the amplitude dataset;
an instantaneous heart rate dataset:
   by extracting an instantaneous heart rate through an analysis of each of the time intervals of the time intervals dataset for a per minute value;
an average heart rate:
   by extracting a mean of the instantaneous heart rate dataset;
a HR tachogram:
   by extracting a plotting of the time intervals dataset;
an autonomous neural activity coefficient of a $\sigma1$:
   by extracting a root of a mean of differences between an adjacent values of the time intervals of the time intervals dataset;
an autonomous neural activity coefficient of a $\sigma2$:
   by extracting a mean of the time intervals of the time intervals dataset;
an autonomous neural activity coefficient of a $\sigma3$:
   by extracting a root of a mean of a deviation of the time intervals of the time intervals dataset from the $\sigma2$;
an autonomous neural activity coefficients of a $\sigma3/\sigma1$, a $\sigma3/\sigma2$ and a $\sigma2/\sigma1$:
   by deriving ratios of the $\sigma1$, the $\sigma2$ and the $\sigma3$;
an autonomous neural activity parameters of P1, P2, P3, P4 and P5:
   by dividing the third order noise free bio-signals or the plurality of optical bio-signal responses and the electrical bio-signal responses into a high frequency band signals, a low frequency band signals, a very low frequency band signals and an ultra low frequency band signals, and followed:
      by extracting a power spectrum under the low frequency band signals to obtain a P1 of the autonomous neural activity parameters;
      by extracting a power spectrum under the high frequency band signals to obtain a P2 of the autonomous neural activity parameters;
      by extracting a ratio of the P1 and the P2 to obtain a P3 of the autonomous neural activity parameters;
      by extracting a power spectrum under the very low frequency band signals to obtain a P4 of the autonomous neural activity parameters;
      by extracting a power spectrum under the ultra low frequency band signals to obtain a P5 of the autonomous neural activity parameters;
a continuous oxygen saturation:
   by extracting a ratio, of an AC to DC ratio, of the optical bio-signal responses of the red LED to that of the infrared LED, wherein the optical bio-signals are obtained after removal of noise as in the first or the second or the third order noise free bio-signals;
an average oxygen saturation:
   by extracting a mean of the continuous oxygen saturation;
a respiratory signals:
   by an iterative analysis of an extremum of a local maxima and a local minima of the amplitude dataset of the third order noise free bio-signals, or the plurality of optical bio-signal responses and the electrical bio-signal responses, to decouple into a plurality of decoupled waves and by analysing the plurality of decoupled waves for a frequency range within a breathing signals frequency range;
a continuous respiratory rate:
   by analysing the respiratory signals for peaks to store a respiratory rate time intervals dataset and by analysing the respiratory rate time intervals dataset for a per minute value; and
an average respiratory rate:
   by extracting an average of the continuous respiratory rate.

8. The medical and health monitoring apparatus of claim 7, wherein:
the correlation of the angle calibrated accelerometer signals with the real-time stable bio-sensing samples to obtain the first order noise free bio-signals is a normalized least mean squaring parameters based adaptive filter; and
the correlation factor is analyzed to obtain a movement error free bio-signal responses of the plurality of optical bio-signal responses and the electrical bio-signal responses.

9. The medical and health monitoring apparatus of claim 7, wherein the medical and health monitoring apparatus is configured to alternatively obtain the instantaneous heart rate dataset, through reduced computational efforts, by analysing a frequency dataset extracted by operating a selection matrix on the third order noise free bio-signals.

10. The medical and health monitoring apparatus of claim 1, wherein the medical and health monitoring apparatus is configured to obtain:
a real-time diastolic blood pressure, a real-time systolic blood pressure and a real-time mean arterial blood pressure:
   by extracting an extremum datasets of a maxima dataset and a minima dataset of the optical bio-signal responses;
   by correlating a mean of a corresponding ratios, of the minima dataset to the maxima dataset of the extremum dataset, with a measured diastolic blood pressure values in real-time and a measurement coefficient to extract the real-time diastolic blood pressure;
   by extracting a time intervals datasets for a corresponding bio-signal response between the extremum datasets of first optical spectrometer and second optical spectrometer;
   by extracting a mean of time intervals of the time intervals datasets;
   by extracting a ratio of a distance, between first optical spectrometer and second optical spectrometer, to that of the mean of time intervals to extract a mean longitudinal pulse velocity; and
   by correlating the mean longitudinal pulse velocity with the real-time diastolic blood pressure to extract the real-time mean arterial blood pressure and the real-time systolic blood pressure.

11. The medical and health monitoring apparatus of claim 1, wherein the medical and health monitoring apparatus is configured to obtain:
a heart to device length:
   by displaying a plurality of user instructions to place arm in different positions; and by recording and correlating the real-time signals from the 9/6-axis accelerometer.

12. The medical and health monitoring apparatus of claim 1, wherein the medical and health monitoring apparatus is configured to obtain:
a real-time blood sugar levels:
by correlating the optical bio-signals responses of the green LED, the red LED and the infrared LED with the optical bio-signals responses of the near infrared LED to eliminate baseline errors and beat to beat fluctuations of tissue absorption, blood flow fluctuations and coherent errors in the optical bio-signals responses of the near infrared LED to extract a processed near infrared bio-signal responses;
by correlating the processed near infrared bio-signal responses with a measured blood sugar values in real-time to extract the real-time blood sugar levels;
a hypoglycaemia and a hyperglycaemia condition:
by analysing the real-time blood sugar levels with a threshold values of hypoglycaemia and hyperglycaemia.

13. The medical and health monitoring apparatus of claim 1, wherein the medical and health monitoring apparatus is configured to obtain:
a rapid eye movement sleep cycles and a non-rapid eye movement sleep cycles:
by evaluating an average heart rate, an average respiratory rate, a blood pressure levels, an oxygen saturation, a blood sugar levels and the body temperature for a realistic range and by analysing the real-time signals of the 9/6-axis accelerometer to verify a sleeping and dormant state;
by analysing at least the average respiratory and the blood pressure levels with a sleep dataset, an activity dataset and a wake dataset to recognize a sleep state;
by analysing a pattern of the average respiratory rate, the blood pressure levels and an instantaneous heart rate to recognize the rapid eye movement sleep cycles and the non-rapid eye movement sleep cycles; and
by recording a time period of the rapid eye movement sleep cycles on recognition of the rapid eye movement sleep cycles and a time period of the non-rapid eye movement sleep cycles on recognition of the non-rapid eye movement sleep cycles.

14. The medical and health monitoring apparatus of claim 1, wherein the medical and health monitoring apparatus is configured to obtain:
a sleep apnoea conditions and a time periods of sleep apnoea:
by analysing an instantaneous heart rate dataset in one or more time frames for a specified range of beats per minute difference between their extremum and for a falling edge and a raising edge in a cycle time to recognize the sleep apnoea conditions;
by analysing a pattern of an average respiratory rate dataset to further verify the sleep apnoea conditions; and
by recording the time periods of sleep apnoea on recognition of the sleep apnoea conditions.

15. The medical and health monitoring apparatus of claim 1, wherein the medical and health monitoring apparatus is configured to obtain:
a step movements dataset:
by analysing the real-time signals of the 9/6-axis accelerometer to extract a normalized values dataset; and
by analysing the normalized values dataset for peaks within a deviation from a mean of the normalized values dataset to detect the step movements and a number of steps.

16. The medical and health monitoring apparatus of claim 1, wherein the medical and health monitoring apparatus is configured to:
start or wake the medical and health monitoring apparatus on detecting a realistic bio-signals;
record a plurality of inputs from the user for learning parameters calibration;
detect or calibrate a plurality of user positions and movement data comprising a sleeping state, a sitting position, a standing position, a running state, a sprinting state and a resistance training state:
by analysing the real-time signals of the 9/6-axis accelerometer and a plurality of vital signal data comprising a heart rate, a respiratory rate, a blood pressure levels, a blood sugar levels, an oxygen saturation, a neural activity parameters and the body temperature;
detect the sleeping state, the sitting position or the standing position:
by analysing a pattern of the heart rate, the respiratory rate and the blood pressure levels at a null step movements;
detect a cycling mode or a driving mode:
by evaluating an average speed with a human physical limit at the null step movement;
detect a walking state, the running state or the sprinting state:
by analysing the average speed and the plurality of vital signal data at a step movement;
detect a number of strides or steps per minute, a number of laps and a minutes per laps count:
by analysing the real-time signals of the 9/6-axis accelerometer and stored values of the GPS;
detect a fatigue condition:
by analysing a real part of an impedance response of the electrical bio-signal responses;
record and display a threshold index of EI (Emotional Index) meter:
by analysing a pattern of the heart rate, the respiratory rate and the real part of the impedance response;
guide the user to a guided breathing technique with an increased breath-out and decreased breath-in pattern, a meditation video and a social chat on recognition of a stress state;
record a new threshold index on trigger of a markup of the threshold index;
detect a hypoglycaemia state and a hyperglycaemia state:
by analysing the real-time blood sugar levels;
detect a congestive heart failure condition:
by analysing a pattern of the heart rate and the respiratory rate;
detect a CO poisoning condition:
by analysing for a decreasing pattern of the oxygen saturation and an increasing pattern of the heart rate and the respiratory rate;
detect a hypoxia condition or a hypoxemia condition or a blood disease condition:
by analysing for a low level of the oxygen saturation, a fast unsteady pattern of the respiratory rate and an increasing pattern of the heart rate;
detect a hypothermia condition:
by analysing for a reducing pattern of the body temperature and the heart rate;
detect a hyperthermia condition:

by analysing for an increasing pattern of the body temperature, the heart rate and the respiratory rate;

automatically send a warning message to an user eco-system, emergency contacts of the user and the user on recognizing health and emergency conditions comprising the hyperthermia, the hypothermia, the hypoxia condition, the CO poisoning condition, the congestive heart failure condition, the hypoglycaemia state and the hyperglycaemia state;

extract and record a basal metabolic rate by analysing data of the heart rate;

rectify errors in the plurality of optical bio-signal responses by applying a feedback of the electrical bio-signal responses; and to remove errors due to circadian cycle and to assess a health of circadian cycle by applying an unsupervised learning.

17. The medical and health monitoring apparatus of claim 1 is synchronized to an accessorial mobile device, wherein the accessorial mobile device is configured to:

log and track a plurality of routine health check-up data comprising a height, a weight, a basal metabolic index, a basal metabolic rate, a workout target, a nutrition intake data and a physical exercise activities;

display a recorded health data including a base heart rate data, a distance commuted and a calories expenditure;

display an emotional index meter that shows a persona oriented stress levels and a tracking meter that reports progress on stress management;

direct to a guided breathing based stress management technique, a mediation technique or a social media communication interface on detecting a threshold of the emotional index meter;

display a daily work management schedule that shows a plurality of scheduled activity with their priority recorded by the user;

display a recorded sleep cycle trend, a sleep period, a non-rapid eye movement sleep cycle length, a rapid eye movement sleep cycle length and a sleep log;

display a warning message regarding sleep disorder on recognizing a sleep disorder;

enable a health advisors network of medical practitioners, dieticians and fitness advisors to interact with the user and guide the user with health practices and therapies;

enable the user to access health blogs, articles and classes;

display a medication tracker and reminder that records a medication pattern and a medication reminders;

alert the user at a time to take medication;

display a real-time vital data of a heart rate, an oxygen saturation, a respiratory rate, a pulse rate variability, a neural activity, a body temperature, a blood sugar levels and a blood pressure levels along with a navigation access to an individual signal physiological waveform of the real-time vital data;

enable the user to share the real-time vital data, the medication pattern, the recorded health data, the sleep cycle trend, the sleep period, the non-rapid eye movement sleep cycle length, the rapid eye movement sleep cycle length, the sleep log, the tracking meter and the plurality of routine health check-up data with the health advisors network, and also to synchronize them on a cloud service; and display an interface to synchronize, install and manage a plurality of third party applications on the medical and health monitoring apparatus.

18. The medical and health monitoring apparatus of claim 1, wherein the microprocessor with internal memory, of the medical and health monitoring apparatus, along with the network of computational and storage devices, that includes at least a server and a plurality of accessorial devices, are configured to execute a parallel computing to increase speed and efficiency of computations.

19. The medical and health monitoring apparatus of claim 1, wherein the medical and health monitoring apparatus further comprises:

a transmittive arrangement of the optical spectrometer configured to capture the plurality of optical bio-signal responses in a transmittive configuration;

an alternative inverted arrangement, of the optical spectrometer in the transmittive configuration, configured to minimize a background optical noise in the plurality of optical bio-signal responses;

a heat dissipating expandable ring body configured to securely hold the medical and health monitoring apparatus on a sensing spot in a size adaptable manner;

a plurality of ventilation holes, on said heat dissipating expandable ring body, configured to regulate a heating; and a foam base on a contact surface configured to minimize motion errors and to enhance a mechanical gripping.

20. The medical and health monitoring apparatus of claim 19, wherein the medical and health monitoring apparatus further comprises:

a spirally extending element, comprising at least an adjustable clipper and a hinge, configured to securely hold the medical and health monitoring apparatus on the sensing spot in a size adaptable manner.

21. The medical and health monitoring apparatus of claim 19, wherein the medical and health monitoring apparatus further comprises:

an open ring structure configured to securely hold the medical and health monitoring apparatus on the sensing spot in a size adaptable manner.

22. The medical and health monitoring apparatus of claim 21, wherein the medical and health monitoring apparatus further comprises:

one or more buttons configured to:
  switch to a plurality of device modes comprising a meeting mode, a work mode, a fitness mode and a sleep mode;
  access and operate a telephonic call, a wireless synchronization facility and a presentation;

a gesture sensor configured to access and operate the presentations; and a vibrator module configured to automatically vibrate in a pattern to guide during an instance of a stress or an anxiety.

23. The medical and health monitoring apparatus of claim 22, wherein the vibrator module is configured to vibrate with an at least 7.5%-25% higher ON time to indicate a breath-out demonstration and with an at least 7.5%-25% lower OFF time to indicate a breath-in demonstration, to guide during the instance of the stress or the anxiety.

24. The medical and health monitoring apparatus of claim 22, wherein the vibrator module is further configured to prompt a plurality of alarms.

25. The medical and health monitoring apparatus of claim 1, wherein the medical and health monitoring apparatus further comprises:

a reflective arrangement of the optical spectrometer configured to capture the plurality of optical bio-signal responses in a reflective configuration;

an adjacent LED-photodetector arrangement, wherein the green LED, the red LED, the infrared LED or the near infrared LED are placed at a noise free recording distance between one or more corresponding photodetectors of the photodetector set; and a foam base on a contact surface configured to minimize motion errors and to enhance a mechanical gripping.

26. The medical and health monitoring apparatus of claim 1, wherein the medical and health monitoring apparatus is packaged, in a packaging form, through a segregation in one or more planes configured to curtail an electrical noise, reduce a tracing efforts and increase a packaging efficiency.

27. The medical and health monitoring apparatus of claim 26, wherein said packaging form has the wireless antennae set arranged in a way to reduce noise interruptions.

28. The medical and health monitoring apparatus of claim 26, wherein said segregation in one or more planes comprises a biosensor plane, an analog and digital frontend plane, an electronic plane and a power plane.

29. The medical and health monitoring apparatus of claim 26, wherein said packaging form further comprises:
a plurality of ventilation pores, on said packaging form or a casing of said packaging form, configured to regulate a heating; and
a foam base, on a contact surface of said packaging form, configured to minimize motion errors and to enhance a mechanical gripping.

30. The medical and health monitoring apparatus of claim 1, wherein the medical and health monitoring apparatus further comprises:
a heat regulating case comprising the optical spectrometer in a reflective configuration;
a soft stretchable cloth configured to hold the medical and health monitoring apparatus steadily on a sensing spot;
a stickable surface and an adhesive surface, on the soft stretchable cloth, configured to steadily hold and fasten the medical and health monitoring apparatus on the sensing spot; and
a foam base, on a contact surface, configured to minimize motion errors.

31. The medical and health monitoring apparatus of claim 1, wherein the medical and health monitoring apparatus further comprises:
a heat regulating case comprising the optical spectrometer in a reflective configuration;
an expandable machine gripper holder configured to attach the medical and health monitoring apparatus to an exercising machine and to steadily hold on a sensing spot; and
a foam base, on a contact surface, configured to minimize motion error.

32. The medical and health monitoring apparatus of claim 1, wherein the medical and health monitoring apparatus further comprises:
an inflatable mini cuff configured to automatically inflate at a contact to detect a resonant point of blood pressure; and
a wireless base station with a touch display configured to display and provide access to live vital signals and a patient information.

33. The medical and health monitoring apparatus of claim 32, wherein the medical and health monitoring apparatus further comprises:
a reflective configuration of the optical spectrometer placed in the inflatable mini cuff;
an electrical cord to alternatively attach the wireless base station to the inflatable mini cuff;
a button configured to reset a medical analysis and to power on or power off; and
a wireless synchronization button configured to wirelessly synchronize the medical and health monitoring apparatus with external devices.

34. The medical and health monitoring apparatus of claim 1 packaged in a wearable form, wherein the medical and health monitoring apparatus further comprises:
a mini inflatable strap configured to inflate to detect a resonant point of blood pressure;
a stress management LED set comprising:
a red light indicator LED that automatically flashes during an instance of a stress or an anxiety; and
a green light indicator LED that automatically flashes in a stress management assisting pattern to guide during the instance of the stress or the anxiety.

35. The medical and health monitoring apparatus of claim 34, wherein the green light indicator LED is configured to blink with an at least 7.5%-25% higher ON time to indicate a breath-out demonstration and with an at least 7.5%-25% lower OFF time to indicate a breath-in demonstration to guide during the instance of the stress or the anxiety.

36. The medical and health monitoring apparatus of claim 34, wherein the medical and health monitoring apparatus further comprises:
a wireless synchronization button configured to wirelessly synchronize the medical and health monitoring apparatus with the network of computational and storage devices;
a trigger button configured to operate applications and functionalities of the medical and health monitoring apparatus; and
a mode indicator light configured to show an operating mode or a functional status of the medical and health monitoring apparatus.

37. The medical and health monitoring apparatus of claim 1 packaged in a wearable form, wherein the medical and health monitoring apparatus further comprises:
a mini touch display configured to provide an access to:
a startup application that displays a time and date, a calorie burnt information, a calorie consumed information, a weekly health history, a battery strength, a climate information and a wireless connectivity information;
a background application, of the startup application, that displays a motivational quote intended to improve spirit of user;
a cardiac training application that tracks and displays a plurality of training data comprising a training intensity, a training period, a rest period, a cardiac rate, an average speed, a distance travelled, a sets count and a reps count;
a persona oriented stress management application that tracks and displays a real-time stress levels in an emotional index meter, a queued work schedule with a priority rating and a descriptive information on stress levels and stress management techniques;
a sleep management application that tracks and displays a real-time sleep information, a user configured alarm and a morning motivational quote;
a medical application that tracks and displays plurality of real-time and recorded vital information that at least includes a heart rate, an oxygen saturation, a respiratory rate, a body temperature, a pulse rate variability, a neural activity balance, a blood pressure levels and a blood sugar levels; and
at least a potentiometer integrated crown and a button configured to navigate through and operate the startup application, the cardiac training application, the persona oriented stress management application, the sleep management application and the medial application.

38. The medical and health monitoring apparatus of claim 37, wherein the medical and health monitoring apparatus is configured to:
   begin a tracking of a training session, with plurality of training data, on a long hold of the button in the cardiac training application;
   switch between the tracking of the training session between the rest period and the training period on a short press of the button in the cardiac training application;
   halt the tracking of the training session on the long hold of the button in the cardiac training application;
   end the tracking of the training session on the short hold of the button post a halt in the cardiac training application; and
   resume the tracking of the training session on the long hold of the button in the cardiac training application.

39. The medical and health monitoring apparatus of claim 37, wherein the medical and health monitoring apparatus is configured to:
   record a plurality of subjective reference data points marked through a press of the button in the persona oriented stress management application; and
   generate the real-time stress levels in the emotional index meter based on the plurality of subjective reference data points.

* * * * *